United States Patent
Sperduti et al.

(10) Patent No.: US 11,766,422 B2
(45) Date of Patent: Sep. 26, 2023

(54) GALLOYLATED PROCYANIDINS FOR TREATING ENDOVASCULAR DYSFUNCTION AND INCREASING BLOOD FLOW

(71) Applicants: UNIVERSITY OF SOUTH FLORIDA, Tampa, FL (US); ENCORE IP MANAGEMENT, LLC, Miami, FL (US)

(72) Inventors: Michael Louis Sperduti, Holbrook, NY (US); Matthew Cleary Nickerson, Placitas, NM (US); Jimmy Roy Huddleston, Tampa, FL (US); Leigh Anthony West, Lutz, FL (US)

(73) Assignees: University of South Florida, Tampa, FL (US); Encore IP Management, LLC, Miami, FL (US)

( * ) Notice: Subject to any disclaimer, the term of this patent is extended or adjusted under 35 U.S.C. 154(b) by 34 days.

(21) Appl. No.: 16/980,519

(22) PCT Filed: Mar. 14, 2019

(86) PCT No.: PCT/US2019/022303
§ 371 (c)(1),
(2) Date: Sep. 14, 2020

(87) PCT Pub. No.: WO2019/178378
PCT Pub. Date: Sep. 19, 2019

(65) Prior Publication Data
US 2021/0330640 A1    Oct. 28, 2021

Related U.S. Application Data

(60) Provisional application No. 62/642,846, filed on Mar. 14, 2018.

(51) Int. Cl.
*A61K 31/353* (2006.01)
*A61P 9/14* (2006.01)

(52) U.S. Cl.
CPC ............. *A61K 31/353* (2013.01); *A61P 9/14* (2018.01)

(58) Field of Classification Search
CPC ............. A61K 31/353; A61P 9/14; A61P 9/08
See application file for complete search history.

(56) References Cited

U.S. PATENT DOCUMENTS

| | | |
|---|---|---|
| 5,531,991 A | 7/1996 | Cheng et al. |
| 5,814,494 A | 9/1998 | Ariga et al. |
| 5,912,363 A | 6/1999 | Nafisi-Movaghar et al. |
| 6,506,419 B2 | 1/2003 | Takahashi et al. |
| 6,544,581 B1 | 4/2003 | Shrikhande |
| 6,670,390 B1 | 4/2003 | Shrikhande et al. |
| 6,706,756 B1 | 3/2004 | Fitzpatrick |
| 7,132,446 B1 | 11/2006 | Fitzpatrick et al. |
| 8,221,806 B2 | 7/2012 | Aviram et al. |
| 8,685,446 B2 | 4/2014 | Moser et al. |
| 2017/0106037 A1 | 4/2017 | Ianiro et al. |
| 2017/0216245 A1 | 8/2017 | Corder |

FOREIGN PATENT DOCUMENTS

| | | |
|---|---|---|
| EP | 1549300 A2 | 7/2005 |
| EP | 3179996 B1 | 6/2017 |
| WO | 99/24471 A1 | 5/1999 |
| WO | 2004037165 | 5/2004 |

OTHER PUBLICATIONS

International Search Report and Written Opinion in PCT/US2019/022303. dated Jun. 6, 2019. 7 pages.
Chemat et al. Review of green food processing techniques. Preservation, transformation, and extraction in Innovative Food Science and Emerging Technologies, (2017) vol. 41, pp. 357-377.
PubChem, "Procyanidin C1", Aug. 1, 2005, https://pubchem.ncbi.nlm.nih.gov/compound/Procyanidin-C1.
Agteresch, Hendrik J., et al. "Adenosine triphosphate." Drugs 58.2 (1999): 211-232.
Badhani, Bharti, Neha Sharma, and Rita Kakkar. "Gallic acid: a versatile antioxidant with promising therapeutic and industrial applications." Rsc Advances 5.35 (2015): 27540-27557. http://pubs.rsc.org/en/content/articlelanding/2015/ra/c5ra01911g#!divAbstract.
Benefits of Increased Blood Circulation. https://www.livestrong.com/article/323211-benefits-of-increased30blood-circulation, posted 2018.
Besco, Rauúl, et al. "The effect of nitric-oxide-related supplements on human performance." Sports medicine 42.2 (2012): 99-117.
Boynton, Alton L., et al. "Extracellular ATP mobilizes intracellular Ca2+ in T51B rat liver epithelial cells: a study involving single cell measurements." Experimental cell research 181.1 (1989): 245-255.
Byun, Eui-Baek, et al. "A procyanidin trimer, C1, promotes NO production in rat aortic endothelial cells via both hyperpolarization and PI3K/Akt pathways." European journal of pharmacology 692. 1-3 (2012): 52-60.http://doi.org/10.1016/j.ejphar.2012.07.011.
Casas, Mariana, Sonja Buvinic, and Enrique Jaimovich. "ATP signaling in skeletal muscle: from fiber plasticity to regulation of metabolism." Exercise and sport sciences reviews 42.3 (2014): 110-116.
Charest, Robert, P. F. Blackmore, and J. H. Exton. "Characterization of responses of isolated rat hepatocytes to ATP and ADP." Journal of Biological Chemistry 260.29 (1985): 15789-15794.

(Continued)

*Primary Examiner* — Theodore R. Howell

(74) *Attorney, Agent, or Firm* — Venable LLP; Keith G. Haddaway; Brenden G. McDearmon

(57) ABSTRACT

The present disclosure is directed to compositions, methods of use, and methods of making, wherein the compositions contain one or more galloylated procyanidins having between two and five epicatechin monomers, wherein the one or more galloylated procyanidins include epicatechin-(4-8)-epicatechin-(4-8)-epicatechin-gallate, catechin trimer gallate, catechin dimer digallate, or combinations thereof.

15 Claims, 19 Drawing Sheets

(56) References Cited

OTHER PUBLICATIONS

Crozier, Alan, Indu B. Jaganath, and Michael N. Clifford. "Dietary phenolics: chemistry, bioavailability and effects on health." Natural product reports 26.8 (2009): 1001-1043.

Davidov-Pardo, Gabriel, Iñigo Arozarena, and María R. Marín-Arroyo. "Optimization of a wall material formulation to microencapsulate a grape seed extract using a mixture design of experiments." Food and Bioprocess Technology 6.4 (2013): 941-951.

Fitzpatrick, David F., et al. "Isolation and characterization of endothelium—dependent vasorelaxing compounds from grape seeds." Journal of agricultural and food chemistry 48.12 (2000): 6384-6390.

Forstermann U, Sessa WC. "Nitric oxide synthases: regulation and function". European Heart Journal. 2012;33(7):829-837. doi:10.1093/eurheari/ehr304.

Gomaa, Adel A. "Characteristics of analgesia induced by adenosine triphosphate." Pharmacology & toxicology 61.3 (1987): 199-202.

Jang, Hyun-Ju, Simone D. Ridgeway, and Jeong-A. Kim. "Effects of the green tea polyphenol epigallocatechin-3-gallate on high-fat diet-induced insulin resistance and endothelial dysfunction." American Journal of Physiology—Endocrinology and Metabolism 305.12 (2013): E1444-E1451. http://doi.org/10.1152/ajpendo.00434.2013.

Jordan, Alexander N., et al. "Effects of oral ATP supplementation on anaerobic power and muscular strength." Medicine & Science in Sports & Exercise 36.6 (2004): 983-990.

Jorquera, Gonzalo, et al. "Cav1. 1 controls frequency-dependent events regulating adult skeletal muscle plasticity." Journal of cell science 126.5 (2013): 1189-1198.

Karas, Daniel, Jitka Ulrichová, and Kateřina Valentová. "Galloylation of polyphenols alters their biological activity." Food and Chemical Toxicology 105 (2017): 223-240. doi:https://doi.org/10.1016/j.fct.2017.04.021.

Khakh, Baljit S., and R. Alan North. "P2X receptors as cell-surface ATP sensors in health and disease." Nature 442.7102 (2006): 527-532.

Maréchal, Georges, and Philippe Gailly. "Effects of nitric oxide on the contraction of skeletal muscle." Cellular and Molecular Life Sciences CMLS 55.8-9 (1999): 1088-1102.

Moncada, S., and E. A. Higgs. "Endogenous nitric oxide: physiology, pathology and clinical relevance." European journal of clinical investigation 21.4 (1991): 361-374.

Mortensen, Stefan P., et al. "Skeletal muscle signaling and the heart rate and blood pressure response to exercise: insight from heart rate pacing during exercise with a trained and a deconditioned muscle group." Hypertension 61.5 (2013): 1126-1133. http://hyper.ahajournals.org/content/hypertensionaha/61/5/1126.full.pdf.

Nair, Anroop B., and Shery Jacob. "A simple practice guide for dose conversion between animals and human." Journal of basic and clinical pharmacy 7.2 (2016): 27-31. doi: 10.4103/0976-0105.177703 PMCID: PMC4804402.

Nogueira, Leonardo, et al. "(−)-Epicatechin enhances fatigue resistance and oxidative capacity in mouse muscle." The Journal of physiology 589.18 (2011): 4615-4631. http://doi.org/10.1113/jphysiol.2011.209924.

Nonaka, Gen-Ichiro, Naoko Miwa, and Itsuo Nishioka. "Stilbene glycoside gallates and proanthocyanidins from Polygonum multiflorum." Phytochemistry 21.2 (1982): 429-432.

Osorio-Fuentealba, Cesar, et al. "Electrical stimuli release ATP to increase GLUT4 translocation and glucose uptake via PI3Kγ-Akt-AS160 in skeletal muscle cells." Diabetes 62.5 (2013): 1519-152.

Parker, John C. "Metabolism of external adenine nucleotides by human red blood cells." American Journal of Physiology-Legacy Content 218.6 (1970): 1568-1574.

Parthasarathy, Sampath, et al. "Oxidized low-density lipoprotein." Free Radicals and Antioxidant Protocols. Humana Press, 2010. 403-417.

Perez-Jimenez, Jara, et al. "Systematic analysis of the content of 502 polyphenols in 452 foods and beverages: an application of the phenol-explorer database." Journal of agricultural and food chemistry 58.8 (2010): 4959-4969.

Ramirez-Sanchez, Israel, et al. "Stimulatory effects of the flavanol (−)-epicatechin on cardiac angiogenesis: additive effects with exercise." Journal of cardiovascular pharmacology 60.5 (2012): 429-438.

Rathmacher, John A., et al. "Adenosine-5′-triphosphate (ATP) supplementation improves low peak muscle torque and torque fatigue during repeated high intensity exercise sets." Journal of the International Society of Sports Nutrition 9.1 (2012):48.

Reiter, Chad EN, Jeong-A. Kim, and Michael J. Quon. "Green tea polyphenol epigallocatechin gallate reduces endothelin-1 expression and secretion in vascular endothelial cells: roles for AMP-activated protein kinase, Akt, and FOXO1." Endocrinology 151.1 (2010): 103-114. https://www.ncbi.nlm.nih.gov/pubmed/19887561.

Schrader, et al., "Uptake and metabolism of adenosine by human erythrocyte ghosts." American Journal of Physiology-Legacy Content 223.1 (1972): 159-166.

Science Daily, "Exercise is good for the heart, high blood pressure is bad: Researchers find out why", Published Jan. 9, 2018, available on-line: https://www.sciencedaily.com/releases/2018/01/180109125224.htm.

Stamlerjs, Meissner G. "Physiology of Nitric Oxide in Skeletal Muscle". Physiol. Rev. 2001;81(1):209-237. doi: 10.1152/physrev.2001.81.1.209.

Steinberg, Daniel. "Low density lipoprotein oxidation and its pathobiological significance." Journal of Biological Chemistry 272. 34 (1997): 20963-20966.

Suhr, et al., Skeletal muscle function during exercise-fine tuning of diverse subsystems by nitric oxide, Int J Mol Sci. 14 (2013) 7109-7139.

Tengan, Celia Harumi, Gabriela Silva Rodrigues, and Rosely Oliveira Godinho. "Nitric oxide in skeletal muscle: role on mitochondrial biogenesis and function." International journal of molecular sciences 13.12 (2012): 17160-17184.

Wilson, Jacob M., et al. "Effects of oral adenosine-5′-triphosphate supplementation on athletic performance, skeletal muscle hypertrophy and recovery in resistance-trained men." Nutrition & metabolism 10.1 (2013): 57.

International Preliminary Report on Patentability issued for Application No. PCT/US2019/022303, dated Sep. 24, 2020.

| Sample | Dose | Mean Fluorescence | (+/-) Standard Diviation |
|---|---|---|---|
| LPS Control | | 30.151 | 8.571 |
| VASO6™ (G.E.O.) | 300 µg/ml | 33.116 | 3.758 |
| VASO6™ (G.E.O.) | 600 µg/ml | 59.634 | 6.626 |
| VASO6™ (G.E.O.) | 1200 µg/ml | 64.107 | 5.22 |
| Arginine silicate | 300 µg/ml | 20.881 | 4.779 |
| Arginine silicate | 600 µg/ml | 24.465 | 5.76 |
| Arginine silicate | 1200 µg/ml | 52.574 | 13.261 |
| L-Citrulline DL-Malate 2:1 | 300 µg/ml | 2.055 | 3.94 |
| L-Citrulline DL-Malate 2:1 | 600 µg/ml | 3.095 | 0.26 |
| L-Citrulline DL-Malate 2:1 | 1200 µg/ml | 1.039 | 0.24 |
| L-Arginine | 300 µg/ml | 6.842 | 1.86 |
| L-Arginine | 600 µg/ml | 1.802 | 1.59 |
| L-Arginine | 1200 µg/ml | 2.336 | 1.6 |

*FIG. 4A*

| Sample | Dose | Mean Fluorescence | % of Change | Sample | Dose | Mean Fluorescence |
|---|---|---|---|---|---|---|
| Arginine silicate vs. VASO6™ (G.E.O.) | 300 μg/ml | 20.881 | 58.59% | VASO6™ (G.E.O.) | 300 μg/ml | 33.116 |
| Arginine silicate vs. VASO6™ (G.E.O.) | 600 μg/ml | 24.465 | 143.75% | VASO6™ (G.E.O.) | 600 μg/ml | 59.634 |
| Arginine silicate vs. VASO6™ (G.E.O.) | 1200 μg/ml | 52.574 | 11.53% | VASO6™ (G.E.O.) | 1200 μg/ml | 64.107 |
| L-Citrulline DL-Malate 2:1 vs. VASO6™ (GEO) | 300 μg/ml | 2.055 | 1511.48% | VASO6™ (G.E.O.) | 300 μg/ml | 33.116 |
| L-Citrulline DL-Malate 2:1 vs. VASO6™ (GEO) | 600 μg/ml | 3.095 | 1826.79% | VASO6™ (G.E.O.) | 600 μg/ml | 59.634 |
| L-Citrulline DL-Malate 2:1 vs. VASO6™ (GEO) | 1200 μg/ml | 1.039 | 6070.17% | VASO6™ (G.E.O.) | 1200 μg/ml | 64.107 |
| L-Arginine vs. VASO6™ (G.E.O.) | 300 μg/ml | 6.842 | 384.01% | VASO6™ (G.E.O.) | 300 μg/ml | 33.116 |
| L-Arginine vs. VASO6™ (G.E.O.) | 600 μg/ml | 1.802 | 3209.32% | VASO6™ (G.E.O.) | 600 μg/ml | 59.634 |
| L-Arginine vs. VASO6™ (G.E.O.) | 1200 μg/ml | 2.336 | 2644.31% | VASO6™ (G.E.O.) | 1200 μg/ml | 64.107 |

FIG. 4B

L-Arginine images (1) 300μg/ml  (2) 600μg/ml  (3) 600μg/ml (w/DAPI)  (4) 1200μg/ml L-Citrulline DL-Malate 2:1 images (1) 300μg/ml  (2) 600μg/ml  (3) 600μg/ml (w/DAPI)  (4) 1200μg/ml Arginine Silicate Images (1) 300μg/ml 
(2) 600μg/ml 
(3) 1200μg/ml Gallate Enhanced Oligomer™/"VASO™" Images (1) 300μg/ml 
(2) 600μg/ml 
(3) 1200μg/ml

GALLOYLATED PROCYANIDINS FOR TREATING ENDOVASCULAR DYSFUNCTION AND INCREASING BLOOD FLOW

CROSS REFERENCE TO RELATED APPLICATIONS

This application is a United States National Phase Patent Application of International Patent Application Number PCT/US2019/022303, filed on Mar. 14, 2019, which claims the benefit of priority to U.S. Provisional Application No. 62/642,846, filed Mar. 14, 2018, which is incorporated by reference herein in its entirety.

TECHNICAL FIELD

This invention relates, generally, to diseases or conditions associated with small or vasoconstricted blood vessels. More specifically, it relates to formulations for increasing intracellular nitric oxide levels to effectuate vasodilation.

BACKGROUND

An intrinsic role of nitric oxide (NO) in vascular physiology is capillary dilation, subsequently increasing oxygen and blood flow to muscle tissue. Since its discovery, there have been a litany of scientific papers that have been published acknowledging nitric oxide's crucial role in vasodilation and cell communication. The vasodilation effect of nitric oxide is relevant to athletics and exercise, as increased blood flow would increase endurance, muscle healing and protein anabolism, subsequently attenuating lactic acid levels. Nitric oxide reduces the amount of lactic acid produced during exercise and extends activity duration and intensity before exhaustion. In addition, it has been demonstrated to shorten healing time following strenuous exercise. By accelerating the delivery of oxygen and nutrients to muscles under stress, nitric oxide has a transient effect on endurance. In addition, continuous exposure of the muscle to nitric oxide has been shown to increase protein anabolism and subsequently increase muscle mass and strength. Additionally, nitric oxide has been shown to enhance both the uptake of glucose and the removal of ammonia in the muscle.

Attempts have been made to increase intracellular nitric oxide, including U.S. Pat. Nos. 6,706,756 and 7,132,446. Other references have described the biomedical significance of Nitric Oxide, such as European Patent No. EP 1,549,300 to Mantione et al. Nitric oxide (NO) is a major signaling molecule in the mammalian immune, cardiovascular and nervous systems. NO produced at one site can have an effect on tissues at a distance. NO is produced from L-arginine by the enzyme, nitric oxide synthase (NOS). NOS occurs in three forms: endothelial (e), neuronal (n), and inducible (i) NOS. The first two forms are constitutively expressed and Ca2+ dependent. Inducible (i) NOS is Ca2+ independent. The three forms of NOS are encoded for on three distinct genes on chromosomes. In general, n- and e-NOS depend on intracellular calcium transients and release NO in the nM range, whereas iNOS, following an induction/latency period, can release NO in the µM range for extended periods of time.

The presence of constitutive and inducible forms of NOS suggest that they may have distinct functions. c- and i-NOS can be distinguished on the basis of the length of time necessary to see an increase in levels of NO and the length of time these elevated levels can be maintained. NO derived from cNOS may occur in two functional forms: the first is always present at low "tonal" or "basal" levels; this basal level can be slightly increased for a short time in response to certain signals, e.g., acetylcholine (ACH). This brief enhanced release of cNOS derived NO can have profound physiological actions, which are evident long after NO has returned to its basal level, for a longer period of time. For example, endothelial cells briefly exposed to morphine and eNOS change their shape from elongated to round, a process that takes several hours. iNOS is induced by various signal molecules, e.g., proinflammatory cytokines. The induction of i-NOS is usually seen after a 3-4 hour delay; iNOS is capable of producing NO for 24-48 hours. These data suggest that NO is always present and that the levels of NO can be regulated either rapidly or slowly depending on the organism's needs. The presence of different regulatory processes implies that NO has different functions, and/or that the levels of NO must be progressively increased in order for it to exert its function.

NO functions as a vascular, immune and neural signal molecule and also has general antibacterial, antiviral actions and the ability to down-regulated proinflammatory events. In the vascular and immune system, one of the key stages in the immune response is the recruitment and activation of leukocytes by the endothelium. Leukocyte activation by the endothelium occurs in stages. The initial step is the attraction of the leukocytes to the endothelium. This is followed by increased leukocyte adhesion and change in shape and finally migration across the endothelium. These cellular changes are accompanied by scheduled changes in synthesis of molecules that regulate cell-matrix interactions.

Normally, non-activated leukocytes roll along the endothelium. The interaction between the two cell types is loose and reversible and mediated by a family of adhesion molecules known as selectins. Activation of leukocytes occurs in response to the release of several chemoattractants including leukotriene B4 and interleukin 8 (IL-8). In the presence of these agents, immunocytes cease to roll, becoming "activated," they start to flatten and adhere with greater strength to the endothelial lining. Activation is mediated by a family of adhesion molecules call the integrins, such as ICAM-1 and NCAM-1. Adherent immunocytes are able to undergo transendothelial migration in the presence of PECAM-1.

This immunocyte-endothelial interaction is down-regulated by NO. NO inhibits platelet and neutrophil aggregation and can diminish the adherence and level of activation of leukocytes and endothelial cells. NOS inhibitors increase platelet adhesion and enhance leukocyte adhesion. NO plays a similar role involving the microglia cells of the nervous system's immune response.

The central nervous system (CNS) is unique in that it uses all three isoforms of NOS to produce NO. The constitutive isoforms e- and n-NOS are found in the normal CNS; however, iNOS is not expressed in the healthy CNS. Pathological states, e.g., trauma, cerebral ischemia and neuronal diseases, increase the levels of e- and nNOS and induce iNOS activity. cNOS derived NO has the ability to down-regulate proinflammatory events via inhibition of NF-κB activation of proinflammatory cytokines. NO upregulates several enzymes involved in immunoregulation, including neutral endopeptidase. (CALLA, acute lymphoblastic leukemic antigen, enkephalinase) or CD10. Thus, cNOS derived No stimulates enzymes that process protein gene products, implying a link between signaling processes involving NO and naturally occurring antibacterial peptides.

NO controls and regulates enzymes that are responsible for liberating these crucial molecules that have a proactive protective function.

Evidence has also been provided that NO plays a role in neurotransmitter release. Morphine and cNOS derived NO release growth hormone and ACTH from rat brain fragments; these neuropeptides are involved in the stress response. Thus, NO is involved in vasodilation, antibacterial and antiviral responses, signal molecule release and inhibition of immunocyte adherence to the endothelium.

There appears to be a tonal or basal level of NO that is physiologically significant. Endothelia from non-insulin dependent diabetics do not exhibit a tonal level of NO and in these individuals vascular disease causes disability and eventual death. A number of researchers have attributed vascular disease in part to alterations associated with eNOS-derived NO and some have speculated this may be due to enhanced free radical generation. Decreases in basal NO levels may also contribute to enhanced platelet function and various neuropathies.

Thus, it appears that tonal or basal NO levels are important in limiting the degree of excitation of nervous, immune and vascular tissues. This tonal NO may manifest itself via effects on adhesion-mediated processes via NF-κB. Estrogen may exert it beneficial vascular protective actions via these processes as well, since it also releases cNOS derived NO. Strengthening this hypothesis in the finding of the cannabinoid CB1 receptor type on mammalian endothelial cells and the finding of a mu opiate receptor on human vascular endothelial cells. (Three general classes of cell surface opioid receptors (kappa, delta and mu) have been described. Receptors exhibiting high binding specificity for morphine have been designated mu opioid receptors.) Detailed analysis has revealed the existence of multiple mu opioid receptor subtypes. Isolated nucleic acid sequences encoding various mu receptors and polypeptides comprising mu receptors (and referred to here as "mu3 opioid receptor(s)") are disclosed in detail in PCT Patent Publication WO 99/24471, published 20 May 1999.

Various vasodilating compounds have been described that interact with NO, as described in U.S. Pat. No. 6,706,756 to Fitzpatrick. The antioxidant properties of various plant favonoids, including procyanidins, are well known. Procyanidins possess endothelium-dependent relaxing (EDR) activity in blood vessels in vitro. The endothelium is a single layer of cells lining every blood vessel. Maintaining healthy endothelial function is critical for overall health and well-being. Endothelial dysfunction is a common characteristic of altered cardiovascular function leading to coronary heart disease, and more generally atherothrombotic diseases including stroke and peripheral vascular disease. All risk factors for cardiovascular disease—raised LDL cholesterol, diabetes, smoking, high blood pressure (hypertension), increasing age and lack of exercise—have been linked to endothelial dysfunction. Endothelial dysfunction is widely recognized as a precursor to atherosclerotic lesion formation. Common characteristics of endothelial dysfunction include: increased inflammation; reductions in the healthy anti-thrombotic functions of the endothelium; increased synthesis of mediators that stimulate remodeling and vascular stiffness; and increased vasoconstriction with reduced vasodilatation.

Endothelial dysfunction is not only associated with the underlying mechanisms leading to cardiovascular disease, but also as a risk factor for cardiovascular events, including myocardial infarction. The severity of endothelial dysfunction is closely associated with increased risk of mortality in patients with chronic heart failure. Although statins and angiotensin-converting enzyme inhibitors cause modest improvements in endothelial function, there are currently no pharmaceutical medications that specifically treat endothelial dysfunction.

The original finding that red wines, grape juice and other grape products exhibited EDR activity was companied by strong evidence that this activity was due to stimulation of NO production by the endothelial cells which form the lining of all blood vessels. Vasorelaxation induced by grape extracts, wines and the like was reversed by NO synthase inhibitors, and vasorelaxation could be restored by exposure of the vessel to L-arginine, the normal substrate for NO synthase. The importance of nitric oxide synthase system is underscored by the finding that a dysfunctional NO system can contribute to several diseases, including atherosclerosis. Therefore, consumption (and absorption) of NO-stimulating compounds in the diet, or in the form of dietary supplements, could contribute to prevention or halting the progress of atherosclerosis, other chronic age-related diseases, or conditions known to involve failure of the NO/NO synthase system, e.g., erectile dysfunction. Although procyanidin compounds, particularly those from grape seed extracts are known to exhibit EDR activity, current supplements administered to patients and consumers do not identify, nor isolate the active and most potent compounds to achieve the desired EDR.

A further characteristic of endothelial dysfunction is increased synthesis of the vasoconstrictor peptide endothelin-1. Antagonists of endothelin-1 cause vasodilation and improve endothelium-dependent vasodilator responses in older people, and in patients with atherosclerosis.

Research on reversing endothelial dysfunction has identified the transcription factor Kruppel-like factor 2 (KLF2) as a key regulator of healthy endothelium, which affords protection from atherosclerosis. It has been proposed that agents that increase KLF2 in the endothelium could be used to treat endothelial dysfunction. Some procyanidins are known to increase KLF2 transiently for a few hours. Identification of agents that could sustain this induction would have greater therapeutic utility in restoring or maintaining endothelial function.

The beneficial effects on cardiac function have been attributed to the high content of flavanols, principally procyanidins. Proanthocyanidins represent a group of plant polyphenols found in roots, barks and fruits with an astringent taste. Proanthocyanidins include the subgroups of procyanidins and prodelphinidins. Proanthocyanidins are biopolymers composed of flavan subunits. Procyanidins are composed of catechin and epicatechin units, also called monomeric procyanidins.

The use of polyphenol compositions in the treatment of endothelial dysfunction have been previously described, as in European Patent No. 3,179,996 to Corder. High flavanol cocoa drinks and high flavanol dark chocolate have been found to improve endothelial function in patients with chronic heart failure, coronary artery disease, and diabetes. Grape seed extract, which is also mainly composed of procyanidins, also lowers blood pressure and improves vascular function. The improvement in cardiovascular function with products containing high amounts of procyanidins is consistent with studies on isolated vessels showing that purified procyanidins cause endothelium-dependent vasodilatation via NO release (U.S. Pat. No. 6,706,756) and inhibit the synthesis of endothelin-1. The anti-atherosclerotic actions of pomegranate juice (Punica Granatum) have been reported (U.S. Pat. No. 8,221,806). Pomegranate juice and pomegranate fruit extract promote endothelium-dependent vasodilatation of isolated vessels.

The use and treatments with polyphenol compositions in preventing or treating endothelial dysfunction can be found in U.S. Patent Publication No. 2017/0216245 to Corder. Polyphenol compounds are a class of organic compounds characterized by the presence of multiple phenol structural units. Thousands of naturally occurring polyphenol compounds are known, and the broad class of polyphenol compounds can be broken down into subgroups, such as flavonoids, which contain a 15 carbon atom scaffold comprising two aromatic rings linked by a three carbon bridge. The sub-class flavonoids can be broken down further to include compounds such as procyanidins, which are oligomeric compounds formed primarily from catechin and epicatechin molecules. One important class of non-flavonoid polyphenols are phenolic acids such as gallic acid, a precursor of hydrolysable tannins, such as ellagitannins.

Natural sources of polyphenols include common foodstuffs such as tea, coffee, cocoa, red wine, beer, cider, fruits, vegetables and nuts (Journal of Agricultural and Food Chemistry, 2010, 58: 4959-69). Other sources of polyphenols include plants that are generally not regarded as foodstuffs, but may be used as traditional herbal medicines, such as flowering plants of the *Epilobium* genus, commonly known as willowherb.

Isolation of procyanidins from raw materials is difficult. U.S. Pat. No. 6,544,581 attempts to resolve this issue, but drawbacks and inefficiencies continue to exist. Proanthocyanidins are extracted from plant material by conventional methods using solvents like water, ethanol or acetone or fluid carbon dioxide. The extracts are purified by solvent/solvent extraction, ultra-filtration or chromatographic procedures. The purified extracts are concentrated by solvent evaporation, freeze drying or spray drying.

An extract from the bark of French maritime pine PYCNOGENOL®, distributed by Horphag Research, Switzerland contains 70-75% by weight proanthocyanidins and other flavanols such as catechin, epicatechin and taxifolin. Furthermore, the extract contains phenolic acids such as caffeic acid, ferulic acid, p-coumarinic acid and p-benzoic acid, which are all present in plants. Of these acids, some are combined with glucose, forming glucose esters or glucose ethers. The extract from pine barks and especially PYCNOGENOL® pine bark extract contains essentially condensed tannins and no hydrolysable tannins. Other proanthocyanidins rich extracts can be obtained from grape seeds, cones from cypress trees, cocoa beans or other plant materials.

In addition, processes for improving the property of proanthocyanidins for improved proanthocyanidin production have been described as in U.S. Pat. No. 5,814,494 to Ariga et al. The proanthocyanidins are a group of compounds bonded by condensation or polymerization of condensed type tannin, that is, flavan-3-ols or flavan-3,4-diols which are present in various plants, as constitutional units. Those compounds may be treated with an acid to form anthocyanidins such as cyanidin, delphinidin and pelargonidin. The compounds include proanthocyanidins such as higher molecular procyanidin, prodelphinidin and propelargonidin, and their stereoisomers or the like which are dimers, trimers, tetramers or decamers.

U.S. Pat. No. 5,531,991 to Cheng, et al. describes the use of an alkaline aqueous extract from the roots of *Polygonum multiflorum* for treating hyperglycemia. Cheng et al. do not disclose the composition of that extract obtained from *Polygonum multiflorum*. However, a publication by Nonaka et al. describes an ethyl acetate extract from *Polygonum multiflorum* containing stilbene glycoside gallates and galloyl procyanidins (Nonaka et al., Stilbene glycoside gallates and proanthocyanidins from *Polygonum multiflorum*, Phytochemistry 21: 429 432 (1982)). It has not been reported that an alkaline extract of *Polygonum multiflorum* as described in the '991 reference contains the same constituents as the ethyl acetate extract described in Nonaka et al., namely galloylated stilbene glycosides and galloylated procyanidins. However, neither the '991 patent nor Nonaka describe galloylated procyanidins for increasing intracellular NO production. Galloylated procyanidins are the result of esterification of procyanidins with gallic acid. The esterification with gallic acid changes the molecular weight of procyanidins, their redox potential and affinity to proteins and enzymes. Galloylated procyanidins belong to the group of hydrolysable tannins and, are physically and chemically different from condensed tannins.

Accordingly, what is needed is an effective mechanism for elevating intracellular nitric oxide levels. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF DESCRIPTION OF THE DRAWINGS

For a fuller understanding of the invention, reference should be made to the following detailed description, taken in connection with the accompanying drawings, in which:

FIG. 4A depicts data showing nitric oxide production.
FIG. 4B depicts data showing nitric oxide production.

SUMMARY

Figure 1:
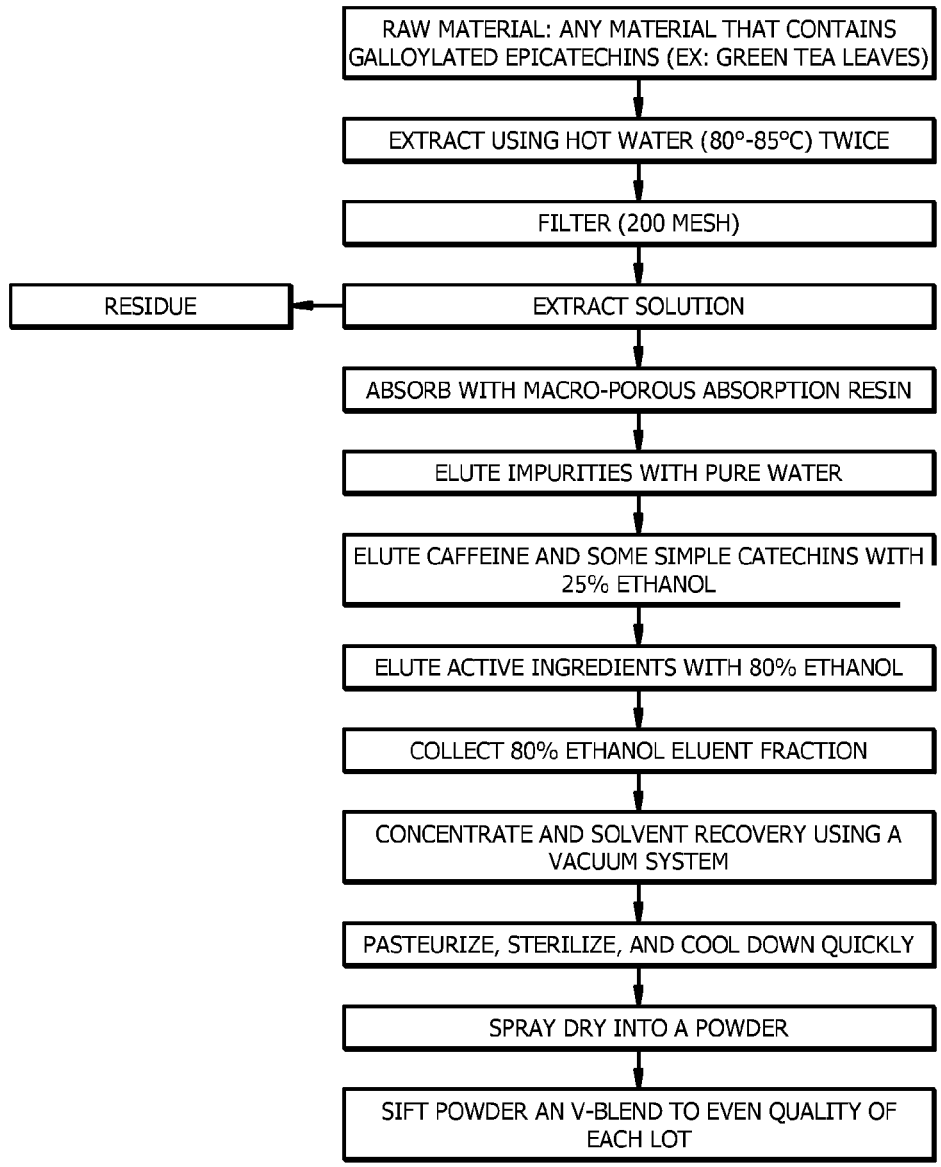
FIG. 1 is a manufacturing flow chart, according to an embodiment of the current invention.

This summary is provided to introduce a selection of concepts in a simplified form. These concepts are described in further detail in the detailed description of example embodiments of the disclosure below. This summary is not intended to identify key features or essential features of the claimed subject matter, nor is it intended to be used to limit the scope of the claimed subject matter.

Embodiments disclosed herein include a composition to treat endovascular dysfunction, the composition comprising: a procyanidin having a preponderance of (-)-epicatechins from materials that contain polyphenols, catechins, epicatechins, and galloylated epicatechins; wherein the procyanidin is galloylated; wherein the epicatechins include between two (2) and five (5) monomers; wherein the epicatechins include isolated epicatechin-(4-8)-epicatechin-(4-8)-epicatechin-gallate (C1-gallate); and a pharmaceutically acceptable excipient or carrier.

In additional embodiments, the composition further comprising one or more of inositol-stabilized arginine, inositol-stabilized arginine silicate, ASI, L-arginine AKG, L-citrulline, L-citrulline malate, arginine HCL, sodium bicarbonate, vitamin C, ascorbic acid, sucrose, aspartate, magnesium, *Saccharomyces cerevisiae*, valeriana officinalis root, alcohol, CBD (medical and recreational), THC (medical and recreational), acetaminophen, dextromethorphan, doxylamine, phenylephrine, ibuprofen, naproxen, Melissa officinalis, zinc, galphimia glauca, luffa operculate, sabadilla, zincum aceticum, zincum gluconicum, dioscorea pseudojaponica, passionflower extract, I-theanine, sceletium tortuosum, melatonin, diphenhydramine, citrus-based extracts, or agmatine sulfate; wherein the composition has enhanced bio-availability, effectiveness, and potency.

In additional embodiments, the composition wherein the procyanidin is obtained from raw materials; wherein the raw material is selected from a group consisting of: green tea leaves, apples (peel on), apricots, pecans, pistachios, almonds and hazelnuts, cherries, peaches, blackberries, black grapes, strawberries, concord grapes, red grapes, cocoa beans, plums (black diamond raw with peel on), pears, Oolong tea, milk chocolate, fava beans, dark chocolate, cherries, cacao beans, broadbeans (immature seeds), black tea, peanut skins, grape vine, blueberries and raspberries.

In further embodiments a method of treating an endovascular dysfunction, comprising: administering a composition to a subject, wherein the composition comprises: a procyanidin having a preponderance of (-)-epicatechins from materials that contain polyphenols, catechins, epicatechins, and galloylated epicatechins; wherein the procyanidin is galloylated; wherein the epicatechins include between two (2) and five (5) monomers; wherein the epicatechins include isolated epicatechin-(4-8)-epicatechin-(4-8)-epicatechin-gallate (C1-gallate); a pharmaceutically acceptable excipient or carrier; wherein the composition comprises a therapeutically effect amount of the galloylated procyanidins having a preponderance of (-)-epicatechins.

In additional embodiments, the method wherein the therapeutically effective amount of the galloylated procyanidins is greater than about 0.4 µM.

In additional embodiments, the method wherein the therapeutically effective amount of the galloylated procyanidins is 0.76 µM.

In additional embodiments, the method wherein a concentration of the therapeutically effective amount of the galloylated procyanidins is about 5%-45% by weight.

In additional embodiments, the method wherein the method further comprises upregulating a canonical pathway in the subject wherein the canonical pathway is selected from the group consisting of: Actin Cytoskeleton Signaling; CD28 Signaling in T Helper Cells; Chemokine Signaling; CREB Signaling in Neurons; CXCR4 Signaling; Ephrin Receptor Signaling; ERK/MAPK Signaling; Fcγ Receptor-mediated Phagocytosis in Macrophages and Monocytes; fMLP Signaling in Neutrophils; GNRH Signaling; GP6 Signaling Pathway; Gα12/13 Signaling; Gαq Signaling; Gαs Signaling; IL-6 Signaling; IL-8 Signaling; Insulin Receptor Signaling; Integrin Signaling; Melatonin Signaling; Nitric Oxide Signaling in the Cardiovascular System; Noradrenaline and Adrenaline Degradation; NRF2-mediated Oxidative Stress Response; Oncostatin M Signaling; Oxidative Phosphorylation; P2Y Purigenic Receptor Signaling Pathway; p70S6K Signaling; PAK Signaling; Phospholipase C Signaling; PI3K Signaling in B Lymphocytes; PI3K/AKT Signaling; Production of Nitric Oxide and Reactive Oxygen Species in Macrophages; Protein Kinase A Signaling; Rac Signaling; RANK Signaling in Osteoclasts; Regulation of Actin-based Motility by Rho; RhoA Signaling; Signaling by Rho Family GTPases; Synaptic Long Term Potentiation; Telomerase Signaling; and α-Adrenergic Signaling.

In additional embodiments, the method wherein administration to the subject causes an increase in intracellular nitric oxide production.

In additional embodiments, the method wherein administration to the subject causes increased blood flow, increased blood oxygenation, lower blood pressure, increased cognizance, dose-specific increase in nitric oxide production, dose-specific increase in vasodilation, reduced fat, increased muscle stamina, increased blood flow to muscles, increased blood flow to brain, decreased exercise/workout recovery time, increased exercise efficiency, increased alertness (e.g., aiding in treatment of narcolepsy, attention deficit disorder, chronic fatigue syndrome, depression, Addison's disease, or sleep deprivation), pre-performance/workout treatment for stimulation of workout vigor (mental and physical) and enhanced performance, post-performance/workout supplement for muscle recovery, male/female virility enhancement, increased metabolic rate, increased workout volume, reduced feeling of effort during exercise, increased motivation to exercise, as drug or supplement delivery mechanism, as a nutrient delivery mechanism, oxygenated blood delivery, as a prevention and/or treatment of endothelial dysfunction, reduced stress and anxiety, as a sleep aid, reduced hangover after alcohol consumption, increased energy, enhanced heart health, enhanced respiratory efficiency, increased angiogenesis, as treatment for wound closure, enhanced food and beverage flavoring, improved skin and hair/coat in non-humans, improved skin and hair in humans, enhanced matrix metalloproteinases proliferation, and as a general aid in animal health and wellness in the subject.

In alternative embodiments, a method of extracting or isolating galloylated procyanidins having a preponderance of (−)-epicatechins from a raw material, the method comprising: selecting the raw material that contains polyphenols, catechins, epicatechins, and galloylated epicatechins;

extracting from the raw material polyphenols, catechins, epicatechins, and galloylated epicatechins (collectively the unrefined material) from the sample using hot water at a temperature of about 80° C. to about 85° C.; passing the unrefined material through a mesh filter; absorbing the filtered material with a macro-porous absorption resin; eluting impurities from the absorbed, filtered material using pure water; eluting the material in ethanol and collecting an ethanol eluent fraction therefrom; concentrating the ethanol eluent fraction and recovering a solvent using a vacuum system; pasteurizing, sterilizing, and quickly cooling the resulting material; spraying drying the material into a powder; sifting and v-blending the powder to even quality of each lot.

In additional embodiments, the method wherein the raw material is selected from a group consisting of: green tea leaves, apples (peel on), apricots, pecans, pistachios, almonds and hazelnuts, cherries, peaches, blackberries, black grapes, strawberries, concord grapes, red grapes, cocoa beans, plums (black diamond raw with peel on), pears, Oolong tea, milk chocolate, fava beans, dark chocolate, cherries, cacao beans, broadbeans (immature seeds), black tea, peanut skins, grape vine, blueberries and raspberries.

In additional embodiments, the method wherein the epicatechins include between about two (2) and about five (5) monomers.

In additional embodiments, the method wherein the epicatechins include isolated epicatechin-(4-8)-epicatechin-(4-8)-epicatechin-gallate (C1-gallate).

In further embodiments, a method of extracting or isolating galloylated procyanidins having a preponderance of (−)-epicatechins from a sample, comprising: initially extracting polyphenols, catechins, epicatechins, and galloylated epicatechins from the sample using ethyl acetate; further extracting the polyphenols, catechins, epicatechins, and galloylated epicatechins from the sample using water; eluting the resulting material using resin and diluting the material with ethanol; filtering the material using activated carbon; concentrating the material; spraying drying the material into a powder; v-blending, sieving, and de-ironing the powder.

DETAILED DESCRIPTION OF THE PREFERRED EMBODIMENT

In the following detailed description, reference is made to the accompanying drawings, which form a part thereof, and within which are shown by way of illustration specific embodiments by which the invention may be practiced. It is to be understood that other embodiments may be utilized, and structural changes may be made without departing from the scope of the present application. These embodiments are described in sufficient detail to enable those of ordinary skill in the art to practice the present disclosure, and it is to be understood that other embodiments may be utilized, and that structural, logical, and electrical changes may be made within the scope of the disclosure.

From the following descriptions, it should be understood that components of the embodiments as generally described and illustrated in the figures herein could be arranged and designed in a wide variety of different configurations. Thus, the following more detailed description of various embodiments, as represented in the figures, is not intended to limit the scope of the disclosure but is merely representative of various embodiments. While the various aspects of the embodiments are presented in drawings, the drawings are not necessarily drawn to scale unless specifically indicated.

The following description provides specific details, such as material types, compositions, material thicknesses, and processing conditions in order to provide a thorough description of embodiments of the disclosure. However, a person of ordinary skill in the art will understand that the embodiments of the disclosure may be practiced without employing these specific details. Indeed, the embodiments of the disclosure may be practiced in conjunction with conventional techniques employed in the industry. Only those process acts and structures necessary to understand the embodiments of the disclosure are described in detail below. A person of ordinary skill in the art will understand that some process components are inherently disclosed herein and that adding various conventional process components and acts would be in accord with the disclosure. In this description, specific implementations are shown and described only as examples and should not be construed as the only way to implement the present disclosure unless specified otherwise herein.

Illustrations presented herein are not meant to be actual views of any particular material, component, or system, but are merely idealized representations that are employed to describe embodiments of the disclosure. Referring in general to the following description and accompanying drawings, various embodiments of the present disclosure are illustrated to show its structure and method of operation. Common elements of the illustrated embodiments may be designated with similar reference numerals. It should be understood that the figures presented are not meant to be illustrative of actual views of any particular portion of the actual structure or method but are merely idealized representations employed to more clearly and fully depict the present invention defined by the claims below.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

Any headings used herein should not be considered to limit the scope of embodiments of the invention as defined by the claims below and their legal equivalents. Concepts described in any specific heading are generally applicable in other sections throughout the entire specification.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

As used herein, "about" means approximately or nearly and in the context of a numerical value or range set forth means ±15% of the numerical. In an embodiment, the term "about" can include traditional rounding according to significant figures of the numerical value. In addition, the phrase "about 'x' to 'y'" includes "about 'x' to about 'y'".

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range.

As used herein, "treat", "treatment", "treating", and the like refer to acting upon a condition (e.g., vasoconstriction or ineffective blood vessels) with an agent (e.g., galloylated procyanidins) to affect the condition by improving or altering it. The improvement or alteration may include an improvement in symptoms or an alteration in the physiologic pathways associated with the condition. The aforementioned terms cover one or more treatments of a condition in a patient (e.g., a mammal, typically a human or non-human animal of veterinary interest), and includes: (a) reducing the risk of occurrence of the condition in a subject determined to be predisposed to the condition but not yet diagnosed, (b) impeding the development of the condition, and/or (c) relieving the condition, e.g., causing regression of the condition and/or relieving one or more condition symptoms (e.g., vasodilation or increased nitric oxide production).

As used herein, the terms "prophylactically treat" or "prophylactically treating" refers to completely or partially preventing (e.g., about 50% or more, about 60% or more, about 70% or more, about 80% or more, about 90% or more, about 95% or more, or about 99% or more) a condition or symptom thereof and/or may be therapeutic in terms of a partial or complete cure or alleviation for a condition and/or adverse effect attributable to the condition.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

The term "therapeutically effective amount" as used herein describes concentrations or amounts of components such as agents which are effective for producing an intended result, including increased intracellular nitric oxide production. Compositions according to the present invention may be used to effect a favorable change in nitric oxide levels, whether that change is an improvement, relieving to some extent one or more of the symptoms of the condition being treated, and/or that amount that will prevent, to some extent, one or more of the symptoms of the condition that the host being treated has or is at risk of developing, or a complete cure of the disease or condition treated.

The term "administration" or "administering" is used throughout the specification to describe the process by which a composition comprising a galloylated epicatechin as an active agent, are delivered to a patient or individual for therapeutic purposes. The composition of the subject invention and methodology in use thereof can be administered a number of ways including, but not limited to, parenteral (such term referring to intravenous and intra-arterial as well as other appropriate parenteral routes), subcutaneous, peritoneal, inhalation, vaginal, rectal, nasal, or instillation into body compartments.

Administration will often depend upon the amount of compound administered, the number of doses, and duration of treatment. In an embodiment, multiple doses of the agent are administered. The frequency of administration of the agent can vary depending on any of a variety of factors, such as nitric oxide levels, and the like. The duration of administration of the agent, e.g., the period of time over which the agent is administered, can vary, depending on any of a variety of factors, including patient response, etc.

The amount of the agent contacted (e.g., administered) can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and film-related factors. Optimization of such factors is well within the level of skill in the art, unless otherwise noted.

As used herein, the term "subject," "patient," or "organism" includes humans and mammals (e.g., mice, rats, pigs, cats, dogs, and horses). Typical hosts to which an agent(s) of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

The phrases "connected to" and "coupled to" refer to any form of interaction between two or more entities, including mechanical, electrical, magnetic, electromagnetic, fluid, and thermal interaction. Two components may be connected or coupled to each other even though they are not in direct contact with each other. For example, two components may be coupled to each other through an intermediate component.

The use of "including," "comprising," or "having," "containing," "involving," and variations thereof herein, is meant to encompass the items listed thereafter and equivalents thereof as well as any additional items a person of ordinary skill in the art would reasonably understand to be included.

Figure 2:
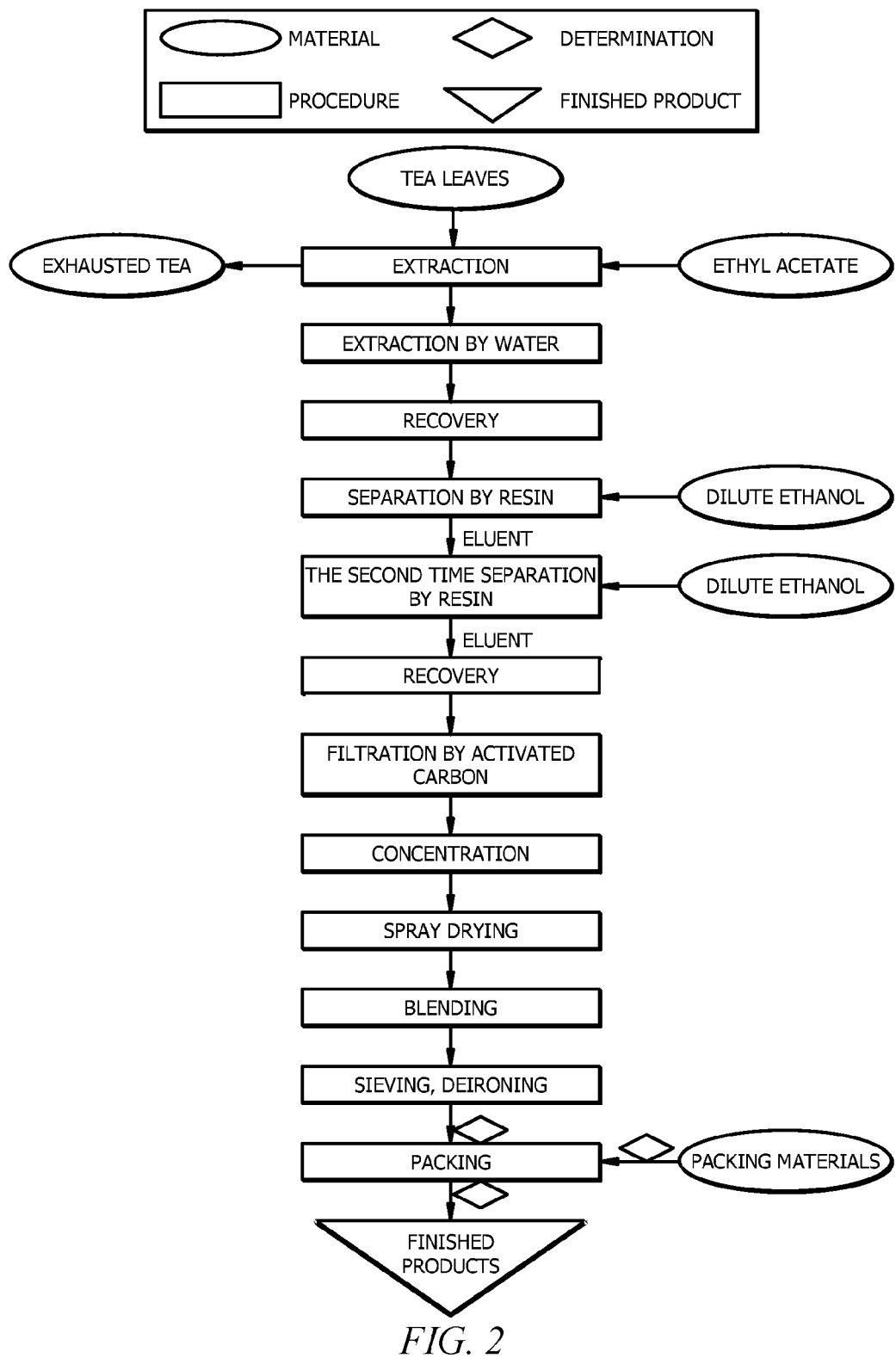
FIG. 2 is a manufacturing flow chart, according to an alternative embodiment of the current invention.
Figure 3A:
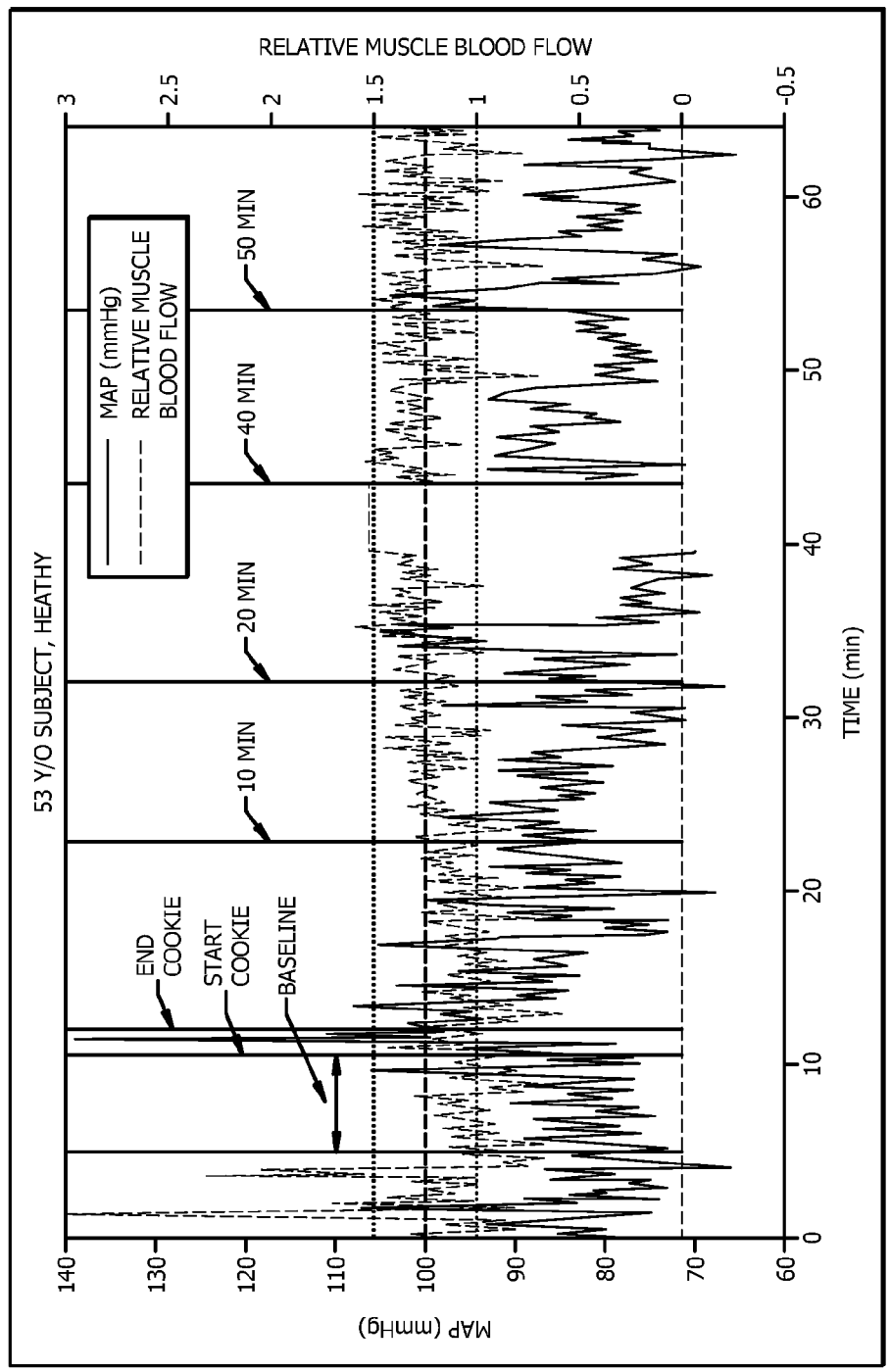
FIG. 3A depicts blood flow and blood pressure regulation/lowering within normal ranges, showing baseline, the start of cookie consumption, end of cookie consumption and readings at 10 min, 20 min, 40 min, and 50 min. Depicts the flow change is about 25-30%, in about 15 min. The dashed black lines are at 1 and 1.5 relative blood flow in a 53 year old subject categorized as healthy.
Figure 3B:
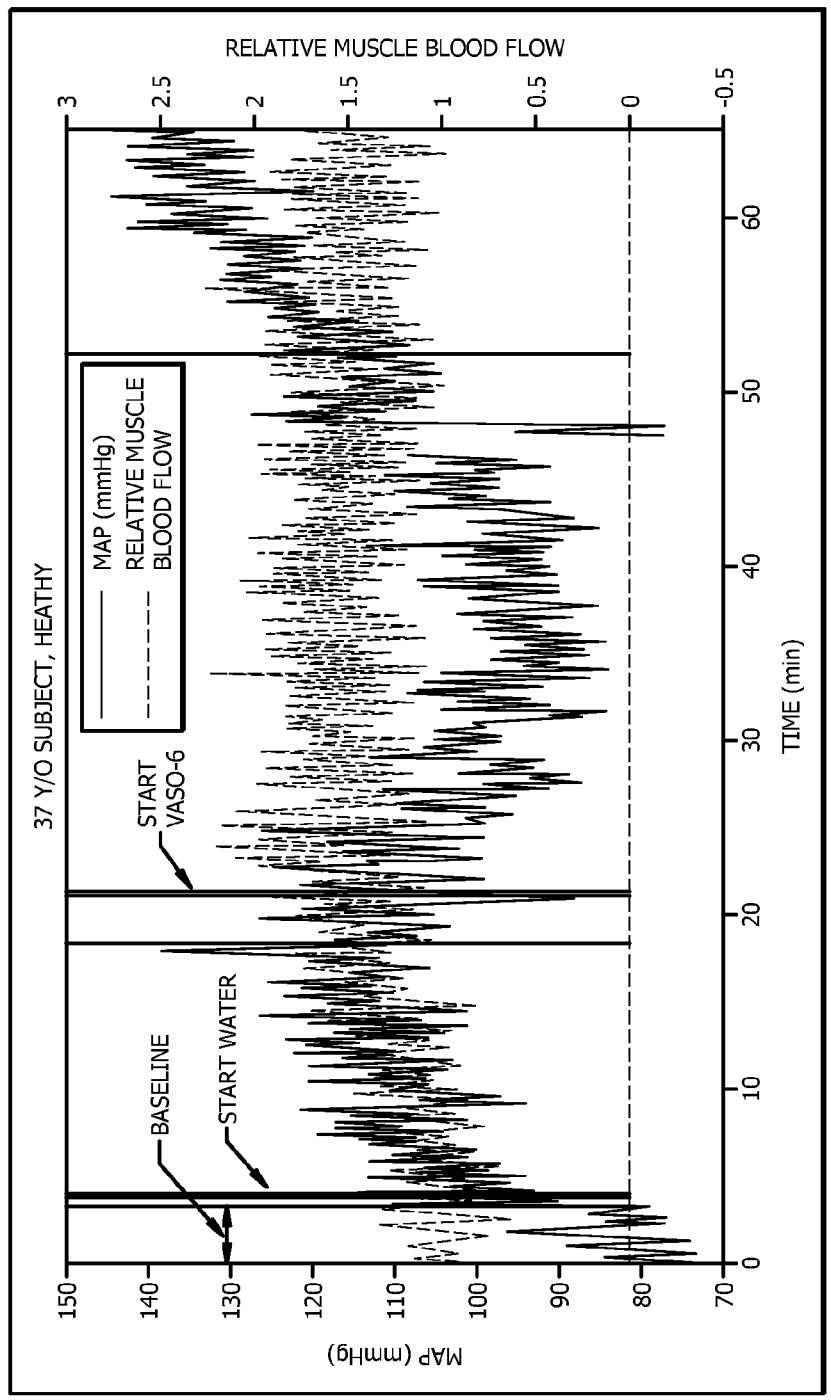
FIG. 3B depicts blood flow and blood pressure regulation/lowering within normal ranges, showing the start of water, start of VASO-6™ (GEO). Depicts there is an instantaneous transient flow increase after GEO (20-25% in 2-3 mins) followed by a more gradual increase to 15% over 10-15 mins. Mean BP decreases after GEO by as much as 15-20% over 15 min in a 37 year old subject categorized as healthy.
Figure 3C:
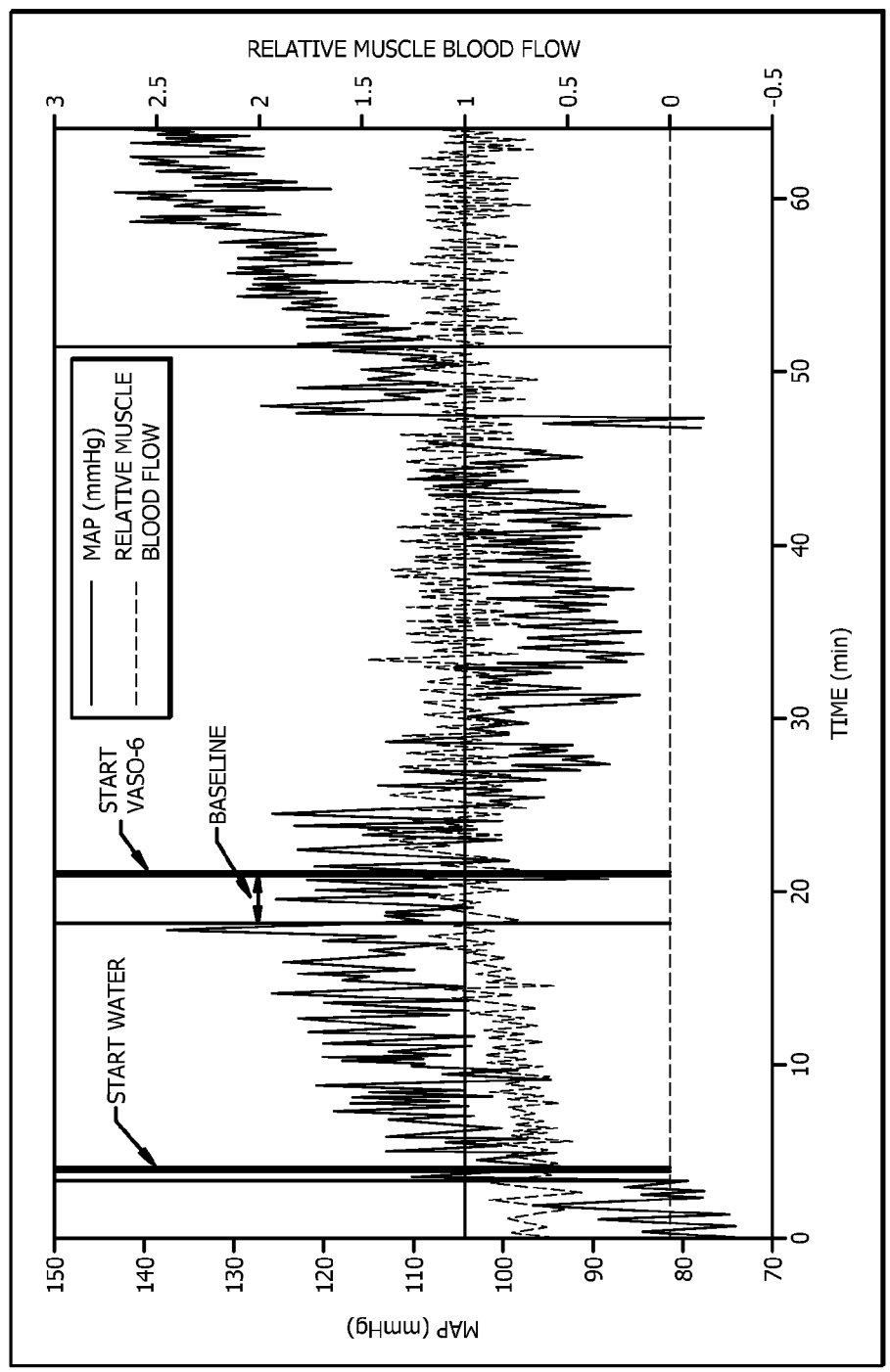
FIG. 3C depicts blood flow and blood pressure regulation/lowering within normal ranges, showing the start of water, start of VASO-6™ (GEO).
Figure 4C:
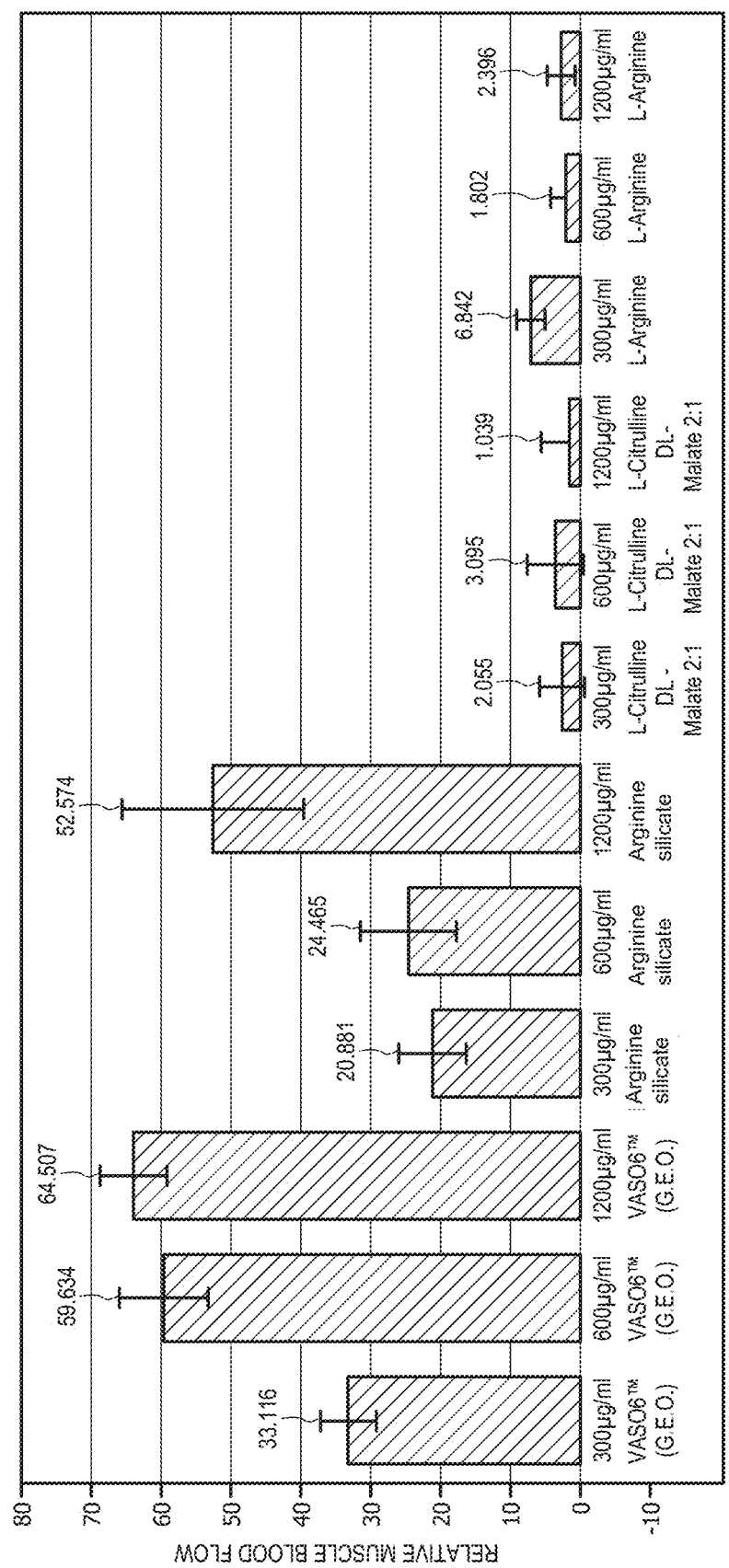
FIG. 4C depicts data showing nitric oxide production.
Figure 5A:
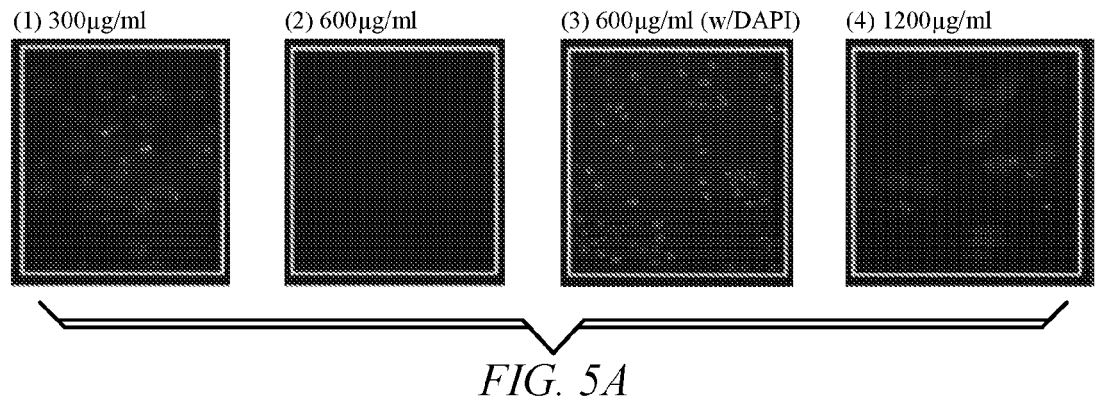
FIG. 5A is a plurality of L-arginine images.
Figure 5B:
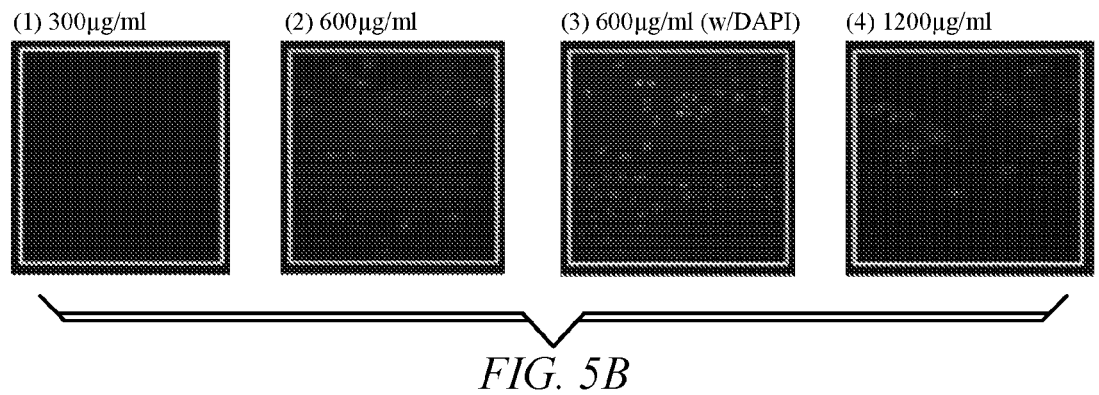
FIG. 5B is a plurality of L-citrulline DL-malate 2:1 images.
Figure 5C:
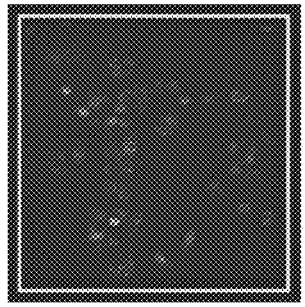
FIG. 5C is a plurality of arginine silicate images.
Figure 5C:
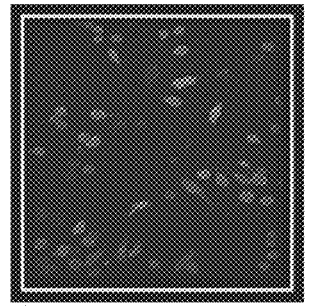
Figure 5C:
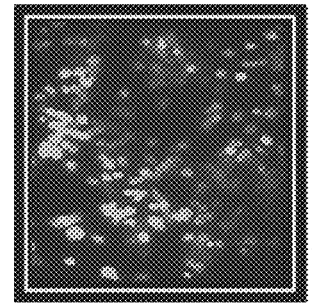
Figure 5D:
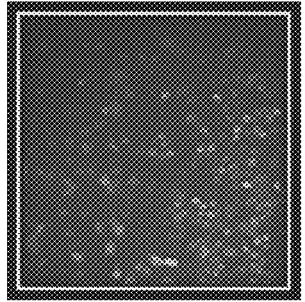
FIG. 5D is a plurality of images of the current formulation/extract.
Figure 5D:
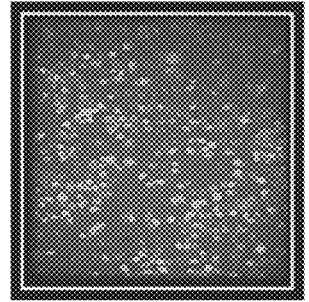
Figure 5D:
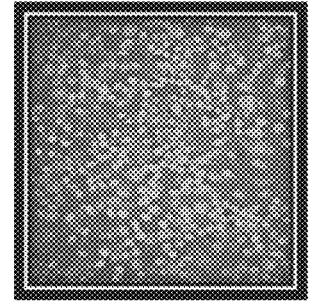
Figure 6A:
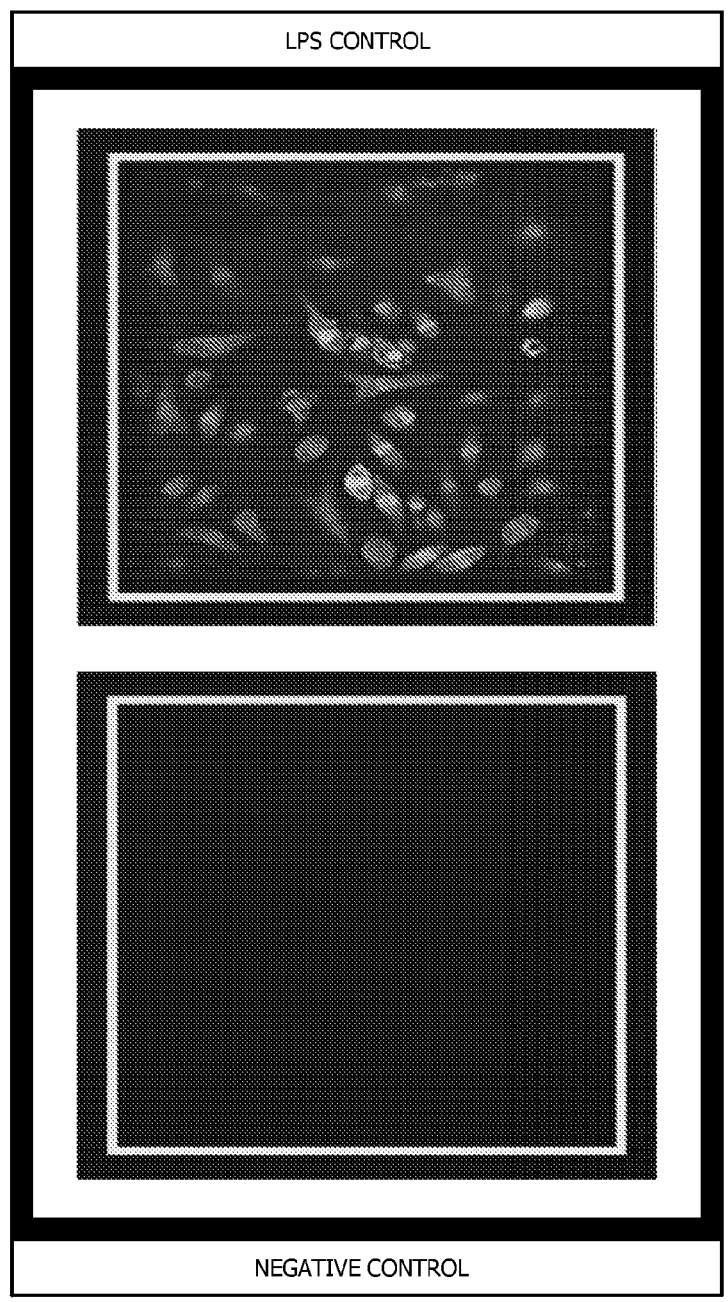
FIG. 6A depicts increase in nitric oxide production in RAW264.7 cells.
Figure 6B:
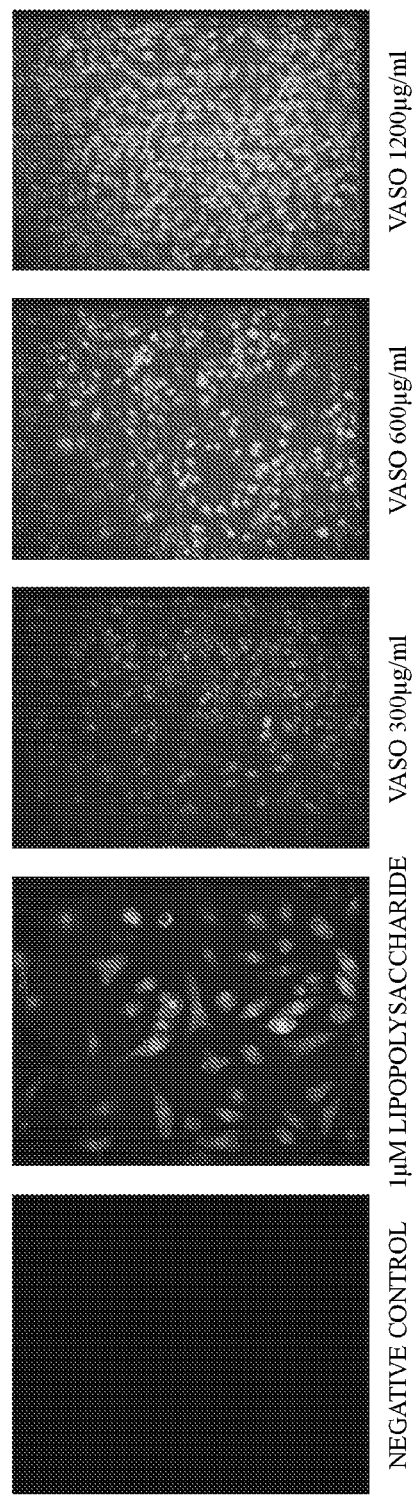
FIG. 6B depicts production of nitric oxide by RAW cells with increasing doses of the current formulation.

Referring in general to the following description and accompanying drawings, various embodiments of the present disclosure are illustrated to show its structure and method of operation. Common elements of the illustrated embodiments may be designated with similar reference numerals. Accordingly, the relevant descriptions of such features apply equally to the features and related components among all the drawings. Any suitable combination of the features, and variations of the same, described with components illustrated in FIG. 1, can be employed with the components of FIG. 2, and vice versa. This pattern of disclosure applies equally to further embodiments depicted in subsequent figures and described hereinafter. It should be understood that the figures presented are not meant to be illustrative of actual views of any particular portion of the actual structure or method but are merely idealized representations employed to more clearly and fully depict the present invention defined by the claims below.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

In certain embodiments, the current invention is formulations and associated methods and therapies for humans and other animals, in the treatment of small vessel disease, high blood pressure, endothelial dysfunction, and other diseases/co-morbidities associated with small vessel disease or with blood vessels that are no longer effective. The formulations include procyanidins having a preponderance of (−)-epicatechins, wherein the procyanidins are preferably galloylated and administered to a patient or subject in need. Flavonoids are known for their healthy effects and limited toxicity. The flavanol (−)-epicatechin (Epi) enhances exercise capacity in mice and Epi-rich cocoa improves skeletal muscle structure in heart failure patients. (−)-Epicatechin decreases myostatin and β-galactosidase and increases levels of markers of muscle growth. In humans, myostatin and β-galactosidase increase with aging while follistatin, MyoD and myogenin decrease. To achieve both bioavailability and potency, it is also contemplated that the number of epicatechins monomers forming each procyanidin is between two (2) and five (5). More specifically, isolated epicatechin-(4-8)-epicatechin-(4-8)-epicatechin-gallate (C1-gallate) is administered to the patient. Through this isolation, formulations were developed to maximize the large molecules responsible for ≥50% vasodilation and small molecules responsible for ≥15% vasodilation.

In certain embodiments, the current invention comprises a formulation, in a kit, including a gallate enhanced oligomer paired with one or more of inositol-stabilized arginine, inositol-stabilized arginine silicate, ASI, L-arginine AKG, L-citrulline, L-citrulline malate, arginine HCL, sodium bicarbonate, vitamin C, ascorbic acid, sucrose, aspartate, magnesium, *Saccharomyces cerevisiae*, valeriana officinalis root, alcohol, CBD (medical and recreational), THC (medical and recreational), acetaminophen, dextromethorphan, doxylamine, phenylephrine, ibuprofen, naproxen, Melissa officinalis, zinc, galphimia glauca, luffa operculate, sabadilla, zincum aceticum, zincum gluconicum, dioscorea pseudojaponica, passionflower extract, I-theanine, sceletium tortuosum, melatonin, diphenhydramine, citrus-based extracts, and/or agmatine sulfate to boost the bioavailability, effectiveness, and potency. In other embodiments, the current invention is a pharmaceutical compound of the dose-specific formulation and combination of the ingredients listed above.

Effects or uses of embodiments of the current invention include, but are not limited to, increased blood flow, increased blood oxygenation, lower blood pressure, increased cognizance, dose-specific increase in nitric oxide production, dose-specific increase in vasodilation, reduced fat, increased muscle stamina, increased blood flow to muscles, increased blood flow to brain, decreased exercise/workout recovery time, increased exercise efficiency, increased alertness (e.g., aiding in treatment of narcolepsy, attention deficit disorder, chronic fatigue syndrome, depression, Addison's disease, or sleep deprivation), pre-performance/workout treatment for stimulation of workout vigor (mental and physical) and enhanced performance, post-performance/workout supplement for muscle recovery, male/female virility enhancement, increased metabolic rate, increased workout volume, reduced feeling of effort during exercise, increased motivation to exercise, as drug or supplement delivery mechanism, as a nutrient delivery mechanism, oxygenated blood delivery, as a prevention and/or treatment of endothelial dysfunction, reduced stress and anxiety, as a sleep aid, reduced hangover after alcohol consumption, increased energy, enhanced heart health, enhanced respiratory efficiency, increased angiogenesis, as treatment for wound closure, enhanced food and beverage flavoring, improved skin and hair/coat in non-humans, improved skin and hair in humans, enhanced matrix metalloproteinases proliferation, and as a general aid in animal health and wellness.

Example 1

In an embodiment, the current invention is a method of manufacture of a formulation including an effective amount of galloylated procyanidins having a preponderance of (−)-epicatechins.

The method includes first selecting raw material that contains polyphenols, catechins, epicatechins, and galloylated epicatechins. Examples of such raw materials include, but are not limited to, green tea leaves (*Camellia sinensis*), apples (peel on), apricots, pecans, pistachios, almonds and hazelnuts, cherries, peaches, blackberries, black grapes, strawberries, concord grapes, red grapes, cocoa beans, plums (black diamond raw with peel on), pears, Oolong tea (*Camellia sinensis*), milk chocolate, fava beans, dark chocolate, cherries, cacao beans, broadbeans (immature seeds), black tea (*Camellia sinensis*), peanut skins, grape vine, blueberries and raspberries. Hot water, ranging from ~80-85° C., is used as an extraction method for the polyphenols, catechins, epicatechins, and galloylated epicatechins. The unrefined material is then run through a 200-mesh filter, and the residue is discarded. The filtered material is then absorbed with a macro-porous absorption resin.

After the filtered material is absorbed, the impurities of the filtered, absorbed material are eluted using pure water. After elution using pure water, the material is then eluted in 25% ethanol to remove caffeine and some simple catechins. Thereafter, the active ingredients are eluted using 80% ethanol, and the 80% ethanol eluent fraction is collected. The material is concentrated, and the solvent is recovered using a vacuum system. The material is then pasteurized, sterilized, and cooled down quickly, followed by being spray dried into a powder. Finally, the powder is sifted and v-blended to even quality of each lot.

Using the foregoing steps, a composition was generated and was tested using liquid chromatography-tandem mass spectrometry to identify analytes/oligomers and quantify concentrations of each analyte/oligomer. Results can be seen in Table 1.

TABLE 1

Oligomer/Analyte identification and concentrations.

| Analyte | Analyte Concentration (ng/mL) | Dilution Factor | Sample Concentration (mg/mL) | Analyte (%) |
|---|---|---|---|---|
| Catechin Dimer G | 56.8 | 100 | 0.0648 | 0.0876 |
| Catechin Trimer G | 6.47 | 5 | 1.30 | 0.000500 |
| ECGC Dimer-1 | 4030 | 100 | 0.0648 | 6.22 |
| Catechin Trimer G | 12.3 | 100 | 0.0648 | 0.0190 |
| ECGC Dimer-2 | 24.1 | 5 | 1.30 | 0.00186 |
| Catechin Tetramer | 6.50 | 5 | 1.30 | 0.000500 |
| Catechin Dimer OG | 93.5 | 100 | 0.0648 | 0.144 |
| ECG Dimer | 13200 | 100 | 0.0648 | 20.3 |
| Catechin Dimer | 4.93 | 100 | 0.0648 | 0.00760 |
| Catechin | 1100 | 5 | 1.30 | 0.0845 |

Example 2

In an embodiment, the current invention is an alternative method of manufacture of the current formulation. The method includes first selecting raw material that contains polyphenols, catechins, epicatechins, and galloylated epicatechins. Examples of such raw materials include, but are not limited to, green tea leaves, apples (peel on), apricots, pecans, pistachios, almonds and hazelnuts, cherries, peaches, blackberries, black grapes, strawberries, concord grapes, red grapes, cocoa beans, plums (black diamond raw with peel on), pears, Oolong tea, milk chocolate, fava beans, dark chocolate, cherries, cacao beans, broadbeans (immature seeds), black tea, peanut skins, grape vine, blueberries and raspberries. Ethyl acetate is used as an extraction method for the polyphenols, catechins, epicatechins, and galloylated epicatechins. A second extraction process, via water, is used to further extract the polyphenols, catechins, epicatechins, and galloylated epicatechins. This material is then recovered.

A separation step is performed by resin and is diluted using ethanol. This process is repeated twice, and the material is recovered. This material is filtered using activated carbon, and the filtered material is concentrated at this phase. The material is then spray dried into a powder. Finally, the powder is v-blended, where sieving and de-ironing takes place.

Concord Grape pumace and seed extracts provide various yield ratios based on the extract type is outlined in Table 2.

Concord GSE Type 1, analysis method GL-816 has provided the following results: Catechin Dimer Gallate: 668 ng/mL; Catechin Trimer Gallate 879 ng/mL; EGCG Dimer-1 ND; Catechin Trimer 337 ng/ML; EGCG Dimer-2 0.302 ng/mL; Catechin Tetramer 1.10 ng/mL; Catechin Dimer Digallate 2.18 ng/mL; ECG Dimer 3.38 ng/mL; Catechin Dimer 66 ng/mL; Catechin 6260 ng/mL.

Concord Pumace and Seeds, analysis method GL-816 has provided the following results: Catechin Dimer Gallate: 54.9 ng/mL; Catechin Trimer Gallate 3.48 ng/mL; EGCG Dimer-1 ND; Catechin Trimer 230 ng/ML; EGCG Dimer-2 0.278 ng/mL; Catechin Tetramer 0.919 ng/mL; Catechin Dimer Digallate 1.69 ng/mL; ECG Dimer 0.967 ng/mL; Catechin Dimer 54.9 ng/mL; Catechin 7700 ng/mL.

Using the foregoing steps, a composition was generated and was tested using liquid chromatography-tandem mass spectrometry to identify analytes/oligomers and quantify concentrations of each analyte/oligomer. Results can be seen in Table 3.

TABLE 2

Concord Grape Pumace & Seed Extracts

| Serial No. | Product & Spec. | Batch No. | Qty. | Yield Ratio | Remarks |
|---|---|---|---|---|---|
| SF-CGS001 | Concord Grape Seed Extract (Type 1) | 181006 | 10 g/bag | Seeds 30:1 | Most suitable for production |
| SF-CGS002 | Concord Grape Seed Extract (Type 2) | 181008 | 1 g/bag | Seeds 200:1 | Highest purity, impractical on actual production |
| SF-CGS003 | Concord Grape Seed Extract (Type 3) | 181010 | 15 g/bag | Seeds residues | |
| SF-CGP001 | Concord Grape Pumace Extract (Type 1) | 181011 | 10 g/bag | 45:1 (Pumace + seeds) | |
| SF-CGP002 | Concord Grape Pumace Extract (Type 2) | 181012 | 5 g/bag | residues (Pumace + seeds) | |

TABLE 3

Oligomer/Analyte identification and concentrations.

| Oligomers | Oligomer Concentration (ng/mL) | Oligomer Concentration (ug/mL) | Dilution Factor | Sample Concentration (mg/mL) | Oligomer (%) |
|---|---|---|---|---|---|
| Catechin Dimer Gallate | 24.1 | 0.0241 | 100 | 0.0611 | 0.0395 |
| Catechin Trimer Gallate | 9.46 | 0.00950 | 5 | 1.22 | 0.000770 |
| Epigallocatechin gallate Dimer 1 | 910 | 0.910 | 100 | 0.0611 | 1.49 |
| Catechin Trimer | 16.5 | 0.0165 | 100 | 0.0611 | 0.0270 |
| Epigallocatechin gallate Dimer 2 | 93.1 | 0.0931 | 5 | 1.22 | 0.00762 |
| Catechin Tetramer | 22.7 | 0.0227 | 5 | 1.22 | 0.00186 |
| Catechin Dimer Digallate | 158 | 0.158 | 100 | 0.0611 | 0.259 |
| Epicatechin gallate Dimer | 16,800 | 16.8 | 100 | 0.0611 | 27.4 |
| Catechin Dimer | 0.510 | 0.000500 | 100 | 0.0611 | 0.000830 |
| Catechin | 24.1 | 0.0241 | 5 | 1.22 | 0.243 |

Example 3

The method of Example 1 or Example 2 was performed to generate an extract including the components discussed above, where this extract was studied for efficacy. Ultimately, the in vitro study herein compares the efficacy of certain substances, along with the developed formulation/extract containing the mixture of polyphenolic compounds, in the induction of intracellular nitric oxide production. These substances are frequently found in sports performance foods and beverages, and include arginine silicate inositol complex (ASI), L-arginine, and L-citrulline-DL-malate (2:1).

Methods

Drug Preparation. Allometric scaling and the general equation of Body Surfaced Area Normalization Method was used to calculate an in vitro 7-dose, based upon the generally accepted human oral dose of these nutritional supplements. The current formulation, L-arginine (COMPOUND SOLUTIONS) and L-citrulline DL-malate 2:1 (COMPOUND SOLUTIONS) were each prepared at 300 mg/ml in DMEM without phenol red (CORNING) and stored at −20° C. until use. Arginine silicate and lipopolysaccharides from *E. coli* 0111: B4 (LPS; SIGMA ALDRICH) were dissolved in DMSO to 300 mg/ml and 50 μg/ml, respectively, and stored frozen until use. 4,5-Diaminofluorescein Diacetate (DAF-FM) was diluted from 5 mM stocks in DMSO.

Cell Culture. RAW264.7 mouse cells (ATCC) were grown at 37° C. in 5% $CO_2$ in DMEM lacking phenol red, supplemented with glucose, pyruvate and L-glutamine and 10% fetal bovine serum (GIBCO; FISHER SCIENTIFIC, LOT #1931538). All experiments were completed with cultures under 8 passages, and cell densities were maintained between $0.2 \times 10^6$ and $0.8 \times 10^6$ cells per ml during maintenance. For sub-culturing, the monolayer was washed twice with HEPES buffered saline (HBS; 140 mM NaCl, 1.5 mM $Na_2HPO_4 \cdot 2H_2O$, 50 mM HEPES, pH 7.2), and then incubated for 2 min in 0.25% Trypsin-EDTA (THERMOFISHER SCIENTIFIC).

Cells were triturated with complete growth medium. Density was determined under phase-contrast using 0.2% Trypan blue. Three viable cell counts were performed on the hemocytometer and averaged. Allometric scaling and the general equation of Body Surface Area Normalization method [J Basic Clin Pharm. March 2016-May 2016; 7(2): 27-31. doi: 10.4103/0976-0105.177703 PMCID: PMC4804402 A simple practice guide for dose conversion between animals and human Anroop B. Nair and Shery Jacob1] were used to calculate an in vitro dose based upon the generally accepted human oral dose of these nutritional supplements.

Nitric Oxide Assay. Nitric oxide levels induced by the various test agents were determined using a free radical-sensing fluorescent dye 4,5-diaminofluorescein diacetate (DAF-FM; THERMOFISHER). DAF-FM diacetate is essentially non-fluorescent until it reacts with nitric oxide to form a fluorescent benzotriazole. DAF-FM diacetate is cell-permeant and passively diffuses across cellular membranes. Once inside cells, it is deacetylated by intracellular esterases to become DAF-FM. Although there has been less published evidence of use of this dye than traditional methods such as the Griess method, this quantification reagent DAF-FM has exhibited extreme sensitivity to nitric oxide insofar as being able to detect individual NO-producing neurons in brain slices.

Here, cells (50,000) in 3 ml of complete growth medium were plated onto 35-mm glass bottom dishes (MATTEK) pre-coated with poly-D-lysine. Cells were grown for 24 h and washed twice in HBS. Three (3) ml of serum-free medium was added. Cells were then treated with 1 μM lipopolysaccharide or various concentrations of test agents and grown for an additional 30 min. DAF-FM was added to cells to a final concentration of 2 μM and incubated for an additional 30 min.

For confocal microscopy, medium was removed, and cells were washed once in HBS and replaced with 3 ml Live Cell Imaging solution (INVITROGEN). Cells were immediately imaged on a PERKIN ELMER ULTRAVIEW ERS confocal microscopy system. Images represent 400× final magnification and were taken using a 1500 ms exposure with a 488 nm Argon-ion laser and 527 nm emission filter. For cell treatments resulting in little or no fluorescence, 4',6-diamidino-2-phenylindole (DAPI, MOLECULAR PROBES) was added at a final concentration of 300 nM to an additional sample. Images were captured and analyzed as tiff formatted files. Densitometry was performed using IMAGEJ software (NIH-bundled with 64-bit Java 1.8.0_112). For determining fluorescence, the entire image was analyzed for each image taken.

Data are representative of 2 independently performed experiments.

Results

Red, green, and blue pixels were converted to brightness values using the formula $V=(R+G+B)/3$. DAPI counter staining is provided for the L-arginine and L-citrulline-DLmalate 2:1 600 µg/ml samples to confirm the adherence of cells in light of their noticeably low mean fluorescence. At corresponding doses of L-arginine, L-citrulline-DL-malate 2:1, and arginine silicate, the current formulation produced a greater amount of DAF-FM fluorescence correlating to an increase in nitric oxide levels against each comparative ingredient/compound. At the biologically active dose of 1 ng/ml incubated for 30 minutes, LPS induced a bright and consistent DAF-FM fluorescence indicating that nitric oxide levels increased, in this cell line.

This demonstrates the ability for the current formulation/extract to induce the production of intracellular nitric oxide in RAW 264.7 mouse macrophage cells. Nitric oxide is produced in various mammalian tissues by three classes of nitric oxide synthase enzymes: endothelium NO synthase (eNOS), neural NO synthase (nNOS) and inducible NO synthase (iNOS). It is the iNOS enzyme that is activated in RAW cells in response to *Lipopolysaccharide*. These murine immune cells provide a static response to an infectious presence by releasing pro-inflammatory mediators including nitric oxide. The mediators aid in increasing blood flow to the site of infection and this in turn improves the invasion of leukocytes. Although a component of immune clearance, compounds that can safely mimic the effects of lipopolysaccharides are sought after since increasing blood flow to the tissues, especially over long periods of time, can increase endurance and protein anabolism.

Example 4

Gallate enhanced oligomer (GEO) with tradename VASO-6™ has been examined using human endothelial cells. The GEO chemical structure contains (−)epicatechins, galloylated procyanidin, epicatechin procyanidin monomers (2-5), isolated epicatechin-(4-8)-epicatechin-(4-8)-epicatechin-gallate (C1-gallate), and flavonoid. The GEO has effects on vasodilator/vasorelaxor-NO production, anti-inflammation, ATP producer, muscle growth, angiogenesis, vasculogenesis, multiple protein/genetic controller for cancer inhibition and viral/bacterial inhibition.

Proanthocyanidins are a class of oligomeric polyphenol compounds composed primarily of (+)-catechin and (−)-epicatechin molecules, as shown below:

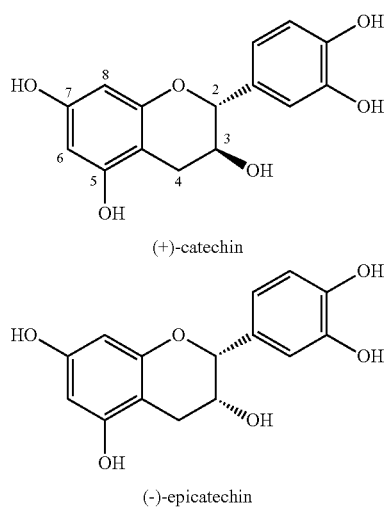

(+)-catechin (−)-epicatechin

Proanthocyanidins can occur as polymers of up to 50 monomer units. Procyanidins are a class of proanthocyanidin that consist exclusively of epicatechin and catechin molecules (Natural Products Report 2009, 26:1001-1043). Structural elucidation of proanthocyanidins, such as procyanidins, is far from trivial, and requires complex NMR analysis, usually at low temperature. However, it is known that catechin/epicatechin units can be linked through a single carbon-carbon bond: a C4-C8 or a C4-C6 linkage. Alternatively, an additional ether bond can be present, i.e. C4-C6, C2-O—C7 or C4-C8, C2-O—C7. As shown below one example of a procyanidin tetramer, joined via C4-C8 linkages:

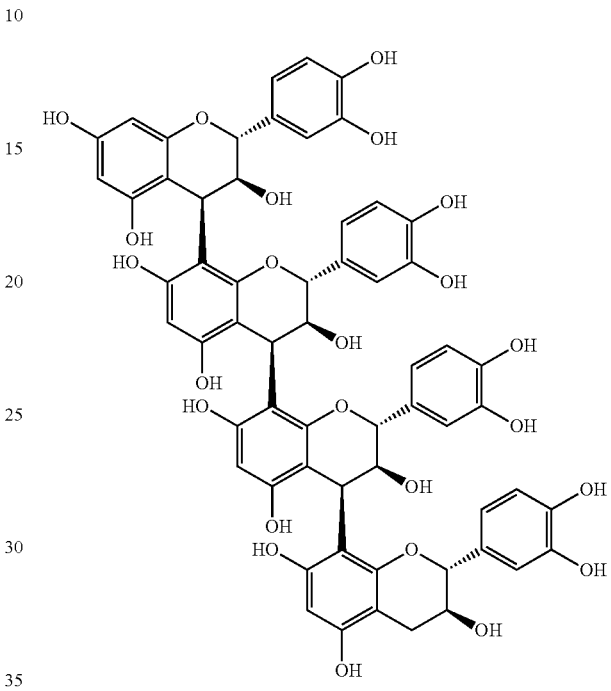

The term "galloylated" is intended to mean that at least one gallic acid molecule is attached to the proanthocyanidin molecule. The gallic acid molecule(s) can be attached in any position. However, it is commonly found that the at least one gallic acid molecule is joined to the (epi)catechin core via an ester linkage to the hydroxyl group at the 3 position. Galloylated proanthocyanidins are frequently found when the proanthocyanidins are derived from particular plant sources, including grapes and grape products. An example of a galloylated epicatechin molecule is shown below:

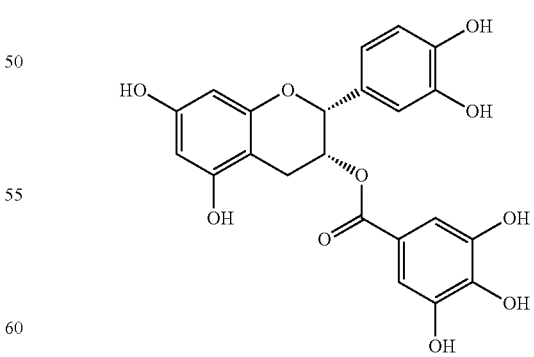

In one embodiment, the compositions of the present invention may be used to enable ergogenic effects, preferably leading to more sustained athletic performance. Thus, in one embodiment the compositions of the invention may be used as ergogenic aids.

In one embodiment, the compositions of the present invention may be used as prophylactics in order to prevent or delay the onset of endothelial dysfunction in patients at risk thereof.

In a further embodiment, the present invention is directed to use of a composition of the invention for the prevention or treatment of endothelial dysfunction.

In a further embodiment, the present invention is directed to use of a composition of the invention in the manufacture of a medicament for use in the prevention or treatment of endothelial dysfunction.

In a further embodiment, the present invention is directed to a method of treating endothelial dysfunction comprising administering to a patient in need thereof, either simultaneously or sequentially, at least one procyanidin, preferably wherein the at least one procyanidin is galloylated. In the case of simultaneous administration, this may be in the form of a pharmaceutical composition of the invention.

In one embodiment, the compositions of the present invention may be used in preventing or treating diseases associated with endothelial dysfunction including arteriosclerosis, hypertension, pulmonary hypertension, coronary artery disease, chronic heart failure, peripheral artery disease, diabetes, chronic renal failure and erectile dysfunction.

In an embodiment, the process of the present invention further involves the addition of at least one pharmaceutically acceptable excipient or carrier. Addition of the pharmaceutically acceptable excipient or carrier may occur simultaneously with, or separately from, the mixing of the galloylated procyanidin, and in any order.

The present application provides compositions comprising certain polyphenol compounds that may be used for the prevention or treatment of endothelial dysfunction. The dosage regimen for the compositions of the present invention will, of course, vary depending upon factors such as the route of administration, the age, sex, health, medical condition and weight of the recipient; the nature and extent of the symptoms; the nature of any concurrent treatment; the frequency of treatment; the route of administration and the effect desired. In particular it is noted that compositions of the present invention may be formulated for use in therapy, or for use as a prophylactic or as an ergogenic aid.

Compositions of this invention may be administered in a single daily dose, or the total daily dosage may be administered in divided doses two, three, or four times daily.

In an embodiment of the invention, desired polyphenol compounds are microencapsulated, either separately or together, to increase stability, or bioavailability or to mask taste. Preferably, microencapsulation is carried out using water-in-oil microencapsulation technology for liquid formulations (see U.S. Pat. No. 8,685,446 B2) or using a three-component microencapsulation mixture of maltodextrin, mesquite gum, and zein, which is spray dried for solid or powder formulations (see Food and Bioprocess Technology, 2013, 6: 941-51).

In an embodiment of the invention, the compositions can be in the form of any pharmaceutically acceptable formulations such as tablets, capsules, buccal tablets, orally disintegrating tablets, oral fast dissolving tablets, dispersible tablet, masticatory, granules, dry suspension, injection, solution, slow-release formulation, controlled-release formulation, rapid-release formulation, and transdermal preparations.

In an embodiment of the invention, the compositions can be prepared as part of a nutraceutical product, for example as a snack bar or a pre-prepared drink/powdered drink formula.

In an embodiment of the invention, the compositions of the invention may advantageously comprise further components such as vitamins, minerals and/or fibre. Suitable vitamins and minerals include, but are not limited to, the B vitamins, vitamin C, folic acid, calcium, iron, magnesium, zinc, selenium, niacin, vitamin D, vitamin A, vitamin E, chromium, copper, manganese, boron, molybdenum, omega fatty acids and co-enzyme Q10. Mixtures of such additional components may be advantageous. For example, in patients with cognitive impairment, it may be advantageous to combine compositions of the invention with a source of omega 3 fatty acids and vitamin B12. Where the compositions are intended for use as ergogenic aids, formulation with a protein source, such as whey powder, may be desirable.

TABLE 4

| Biological activity of galloylated and non-galloylated and non-galloylated polyphenols | | | |
|---|---|---|---|
| Biological activity | Control | Compound[a] | Effect[b] |
| Inhibition of fatty acid synthase activity | Untreated enzyme | GA | ↑ |
| | | C | • |
| | | EC | ↑ |
| | | EGC | ↑ |
| | | EGCG | ↑↑↑ |
| | | ECG | ↑↑↑ |
| Inhibition of rat liver microsomal 5α-reductase | Untreated enzyme | EGCG | ↑ |
| | | PGG | ↑↑↑ |
| | | TDG | ↑↑↑ |
| | | T3G | ↑↑ |
| | | T3'G | ↑↑↑ |
| Trolox-equivalent antioxidant activity | C, EC | EGCG | ↑↑ |
| Triggering of suicidal erythrocyte death | Untreated erythrocytes | PGG | ↑↑ |
| Inhibitory effects on LNCaP and DU145 cells | Untreated cells | PGG | ↑↑↑ |
| Induction of apoptosis in HL-60 cells | Untreated cells | GA | ↑↑ |
| | | DGR | ↑↑↑ |
| Growth inhibition of MCF-7 and MDA-MB231 cells | Untreated cells | PGG | ↑↑↑ |
| Cytotoxicity towards K562 cells | Untreated cells | PGG | ↑ |
| Reduction of pancreatic lipase activity in vitro | Untreated enzyme | EGCG | ↑↑ |
| | | GCG | ↑↑↑ |
| | | ECG | ↑↑ |
| | | CG | ↑↑↑ |

TABLE 4-continued

Biological activity of galloylated and non-galloylated and non-galloylated polyphenols

| Biological activity | Control | Compound[a] | Effect[b] |
|---|---|---|---|
| Induction of apoptosis in HTB9 cells | Untreated cells | 7-GSB | ↑↑↑ |
| Inhibition of VEGF-induced proliferation of HUVEC | Untreated cells | ECGC | ↑↑ |
| | | ECG | ↑↑ |
| | | EGC | ↑ |
| | | EC | ↑ |
| Activiation of type 1 ryanodine receptor | Untreated receptor | EGCG | ↑↑↑ |
| | | ECG | ↑↑↑ |
| | | EGC | ↑ |
| | | EC | • |
| Cytotoxicity towards S-G cells (immortalized gum epithelial cells) | Untreated cells | EGCG | ↑↑↑ |
| | | EGC | ↑↑ |
| | | ECG | ↑↑↑ |
| | | EC | ↑ |
| | | CG | ↑↑↑ |
| | | C | ↑ |
| Inhibition of NA+/K+ ATPase pump activity | Untreated pump | EGCG | ↑↑ |
| | | ECG | ↑↑ |
| | | EGC | ↑ |
| | | EC | ↑ |
| Inhibition of NA/H exchanger activity | Untreated exchanger | EGCG | ↑ |
| | | ECG | ↑↑ |
| | | EGC | ↑↑↑ |
| | | EC | ↑↑↑ |
| Suppression of fatty acid synthase expression n MCF-7 cells | Untreated cells | C | • |
| | | EC | • |
| | | EGC | • |
| | | EGCG | ↑↑↑ |
| Reduction of cell viability in HL-60 cells | Untreated cells | EGCG | ↑↑ |
| | | PGG | ↑↑↑ |
| | | TDG | ↑↑ |
| | | T3G + T3'G | ↑ |
| | | TF | • |

By way of example, the daily dosage of procyanidins in the compositions of the invention is from about 100 mg to about 1000 mg, preferably about 250 to about 600 mg. The daily dosage of ellagitannins in the compositions of the invention is from about 50 mg up to about 1000 mg, preferably about 300 mg to about 600 mg.

TABLE 5

Biological activity of galloylated polyphenols compared to their non-galloylated parent molecules

| Parent molecule[a] | Galloyl-derivative[a] | Biological activity | Effect[b] |
|---|---|---|---|
| SB | 7-GSB | Antioxidant activity | ↑↑↑ |
| DB1 | DGB1 | Cytotoxicity towards human cancer cell lines derived from breast | ↑[c] |
| DB2 | DGB2 | (MDA-MB-231, MDA-MB-435, MCF-7, BT-20); prostate (LNCap, DU-145); stomach (SNU-1); duodenum (Hu-Tu-80); colon (HT-29); rectum (SW-1463); lung (A549); central nervous system (U-87); bone (U202) and skin (SK-MEL-5) cancer | ↑[c] |
| RST | DGR | Growth inhibition of HT-29 human colorectal carcinoma cells | ↑ |
| RST | DGR | DPPH• radical scavenging activity | ↑↑↑ |
| RST | DGR | Inhibition of BxPC-3 cell colony formation (pancreatic adenocarcinoma cells) | ↑ |
| Quercetin | 3GQ | Induction of heme oxygenase 1 in RAW264, 7 cells | ↓↓ |
| Taxifolin | 7GT | | ↑↑↑ |
| Quercetin | 3GQ | Cytotoxicity, inhibition of proliferation, migration and tube formation of HUVEC[d] | ↑↑ |
| Taxifolin | 7GT | | ↑↑ |
| EGC | EGCG | | ↑↑[c] |
| EC | ECG | Inhibition of VEGF-induced proliferation migration and tube formation of human umbilical vein endothelial cells (HUVEC) | ↑[c] |
| SB | 3-GSB | Cytotoxicity, inhibition of proliferation, migration and tube formation of HUVEC[d] | •[c] |
| | 7-GSB | | ↑↑↑ |
| | 20-GSB | | ↑[c] |
| | 23-GSB | | ↑[c] |
| DHS | 3-GDHS | Cytotoxicity, inhibition of proliferation, and migration of HUVEC[d] | ↓↓[c] |
| | 7-GDHS | | ↑↑↑ |
| | 20-GDHS | | •[c] |
| | 23-GDHS | | ↑[c] |

Example 5

Figure 7:
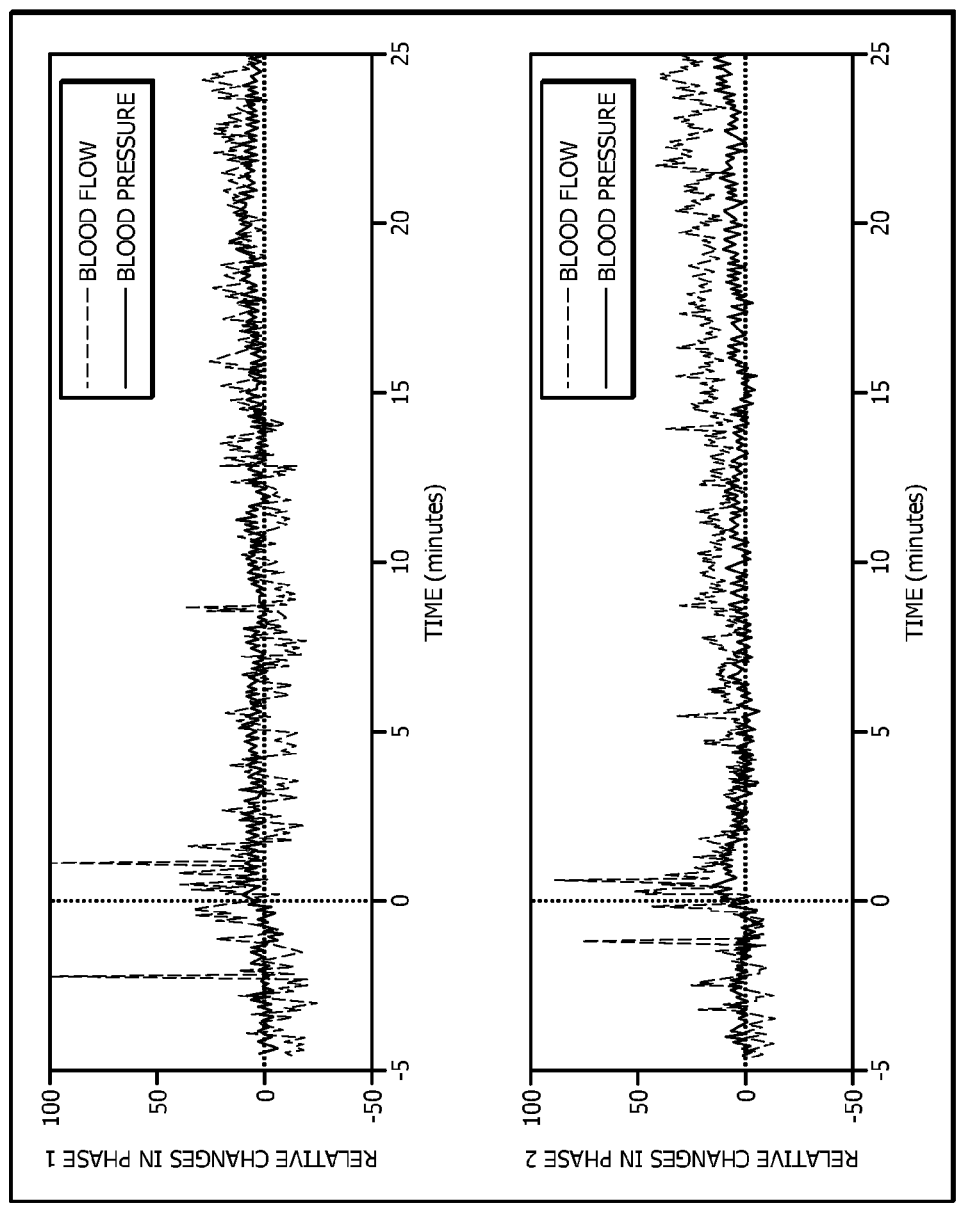
FIG. 7 depicts a graph showing the relative changes in blood flow and blood pressure in subjects using just energy drink in phase 1, and energy drink plus VASO-6 in phase 2.
Figure 8:
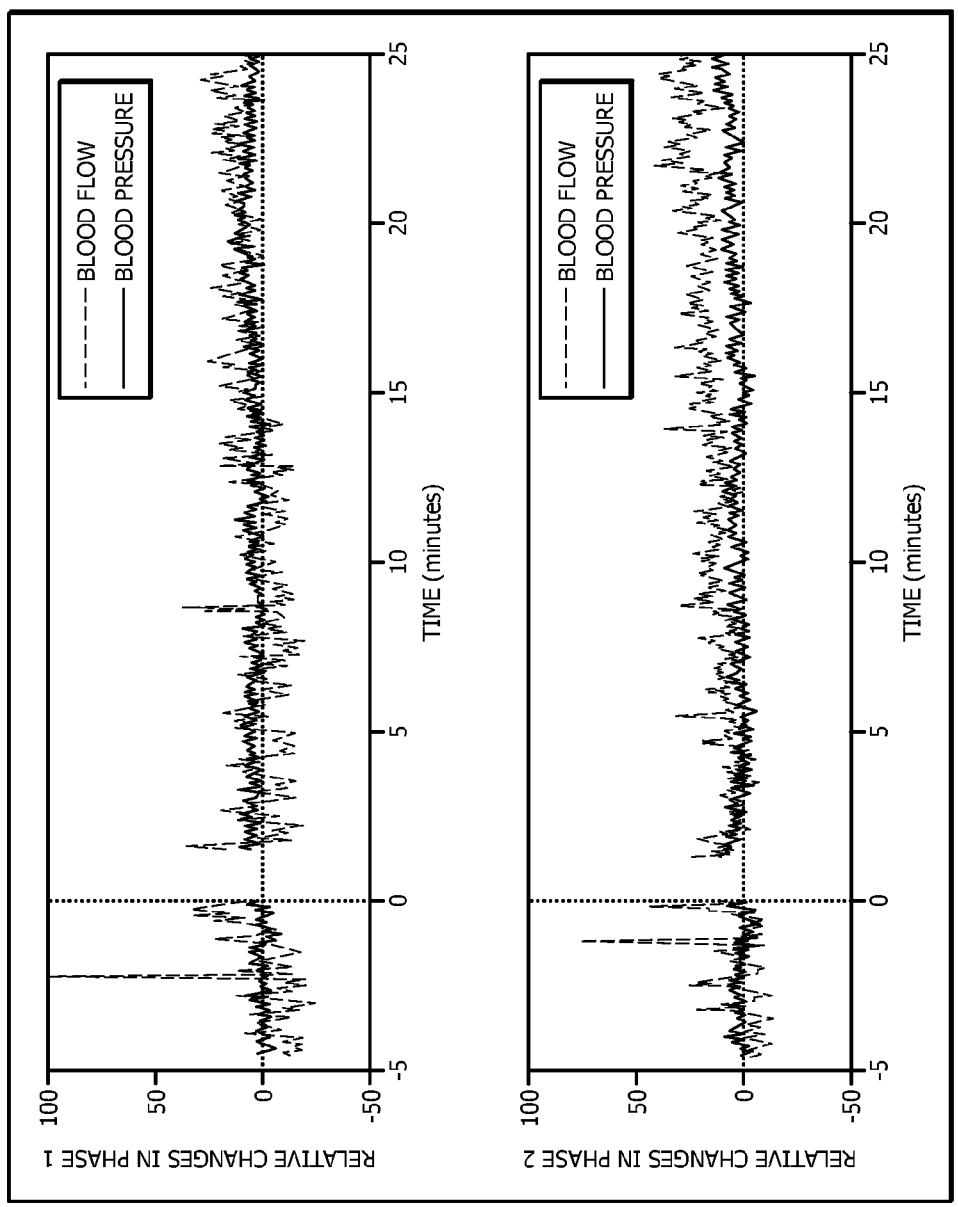
FIG. 8 depicts a graph showing the relative changes in blood flow and blood pressure in subjects using just energy drink in phase 1, and energy drink plus VASO-6 in phase 2.
Figure 9:
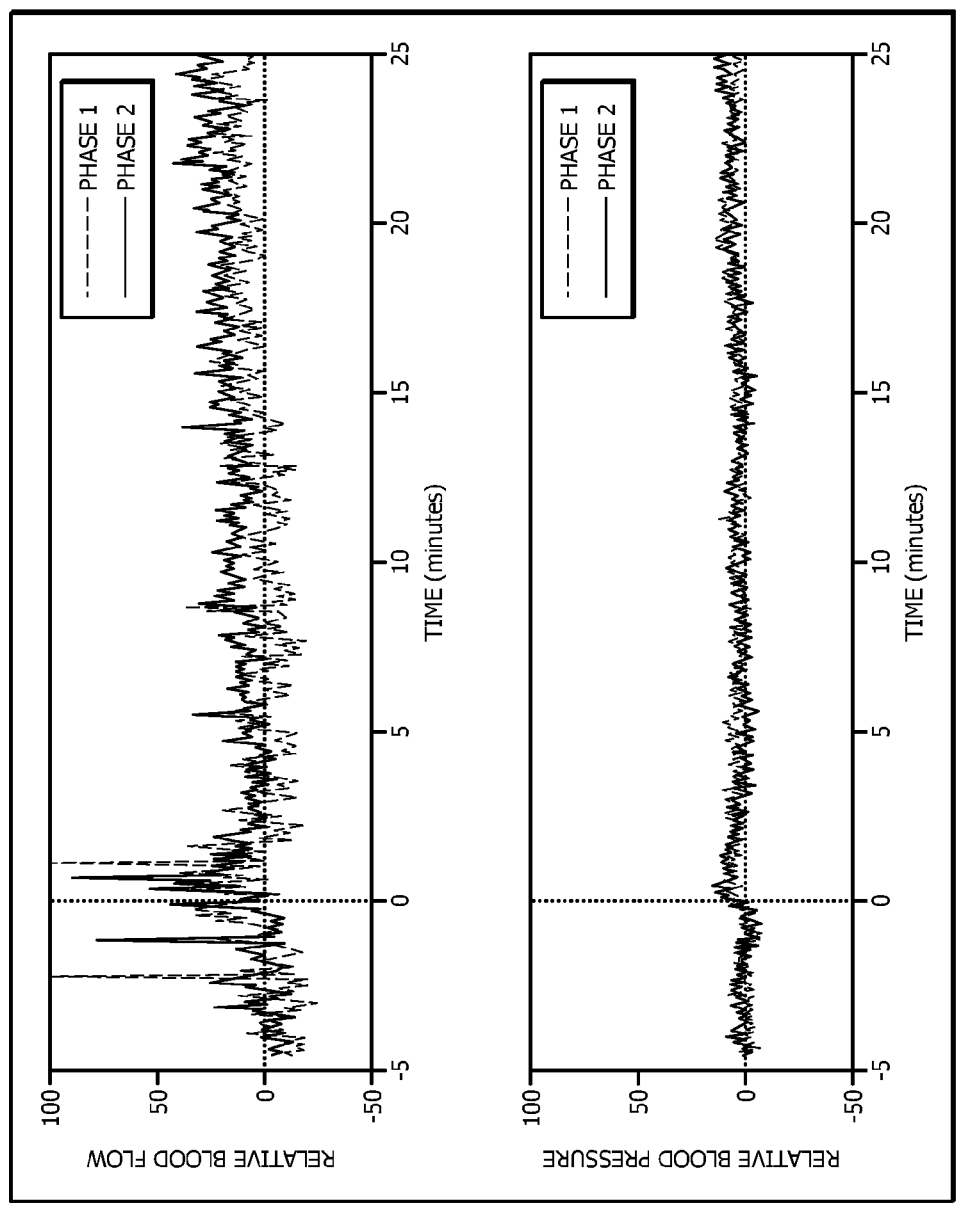
FIG. 9 depicts a graph showing the relative changes in blood flow in subjects using just energy drink in phase 1, and energy drink plus VASO-6 in phase 2 and a graph showing relative changes in blood pressure in subjects using just energy drink in phase 1, and energy drink plus VASO-6 in phase 2.
Figure 10:
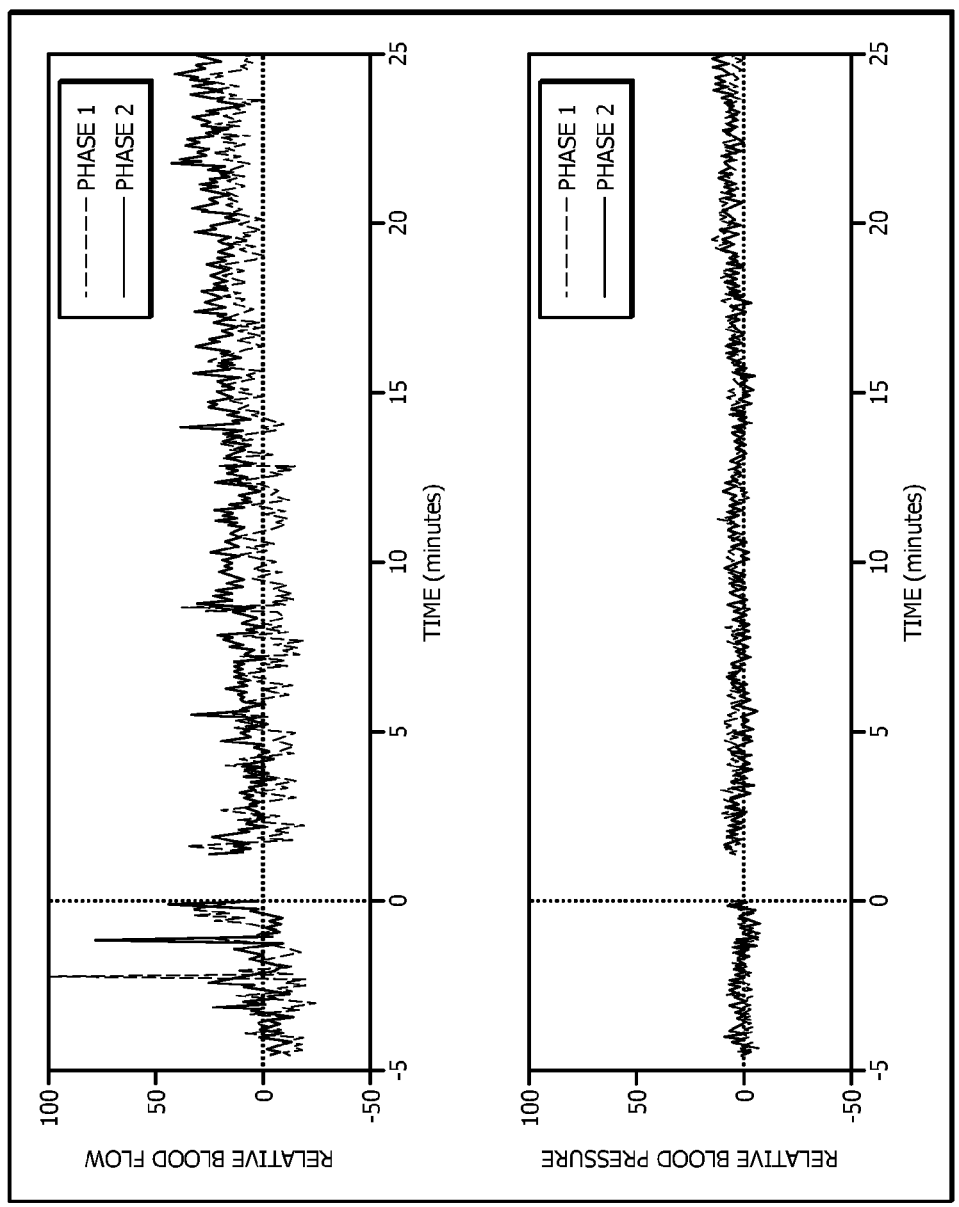
FIG. 10 depicts a graph showing the relative changes in blood flow in subjects using just energy drink in phase 1, and energy drink plus VASO-6 in phase 2 and a graph showing relative changes in blood pressure in subjects using just energy drink in phase 1, and energy drink plus VASO-6 in phase 2.

Data on human subject blood flow and blood pressure were gathered with subjects drinking just an energy drink and an energy drink with VASO-6™. FIGS. 7 and 9 depict the graph of the changes in blood flow and blood pressure recorded during the time the subjects drink the cocktail including the time after the subjects are done drinking the cocktail. FIGS. 8 and 10 depict the graph of the changes in blood flow and blood pressure recorded only with the time after the subjects are done drinking the cocktail. As can be seen in the graphs in FIGS. 7-10 the addition of VASO-6™ increased the blood flow by about 15% starting approximately at the ten (10) minute mark. This increase in blood flow is maintained until the end of the test. As can be seen in the graphs in FIGS. 7-10 the addition of VASO-6™ does not appear to change the blood pressure in the subjects.

While clinical results have shown VASO-6™ promotes nitric oxide production and blood flow, as well as increased vasodilation, little is known about the cellular or molecular mechanisms involved.

To further elucidate the molecular mechanisms affected by VASO-6™ treatment, mas spectrometry-based proteomics was performed on cultured human aortic endothelial cells treated with 2 doses of VASO-6™ (300 and 600 mg) while the control was DMSO treated.

Human aortic endothelial cells were collected, and protein was solubilized before being proteolytically digested with Trypsin to generate peptides for LC-MS/MS analysis. Peptides were separated on a 50 cm C18 column (Thermo) using an Ultimate 300 UHPLC system (Thermo) and analyzed on a hybrid quadrupole-Orbitrap mass spectrometer (Q Exactive Plus, Thermo).

Raw data files were searched using MaxQuant (www-.maxquant.org) against the Uniprot Homo Sapiens reference proteome database. Ratios were generated by dividing the intensity of a given protein in the treatment group by the intensity of the protein in the control sample. Significant outliers were determined using the Significance A test in Perseus (www.coxdocs.org). Proteins that were found to be significant were uploaded into Ingenuity Pathways Analysis software for bioinformatic analysis.

Over 2300 proteins were identified in each sample, of which 198 showed significant changes in abundance after treatment with 300 mg VASO-6™, while 181 proteins showed significant changes following treatment with 600 mg VASO-6™.

IPA analysis revealed several canonical pathways, as well as cellular and molecular and functions associated with the significantly altered proteins. Significance is established using a z-score.

Comparison analysis provides an indication of potential dose-dependent changes. For example, joint inflammation is moderately inhibited in the 300 mg dose (z-score −0.655) and is significantly inhibited with the 600 mg dose (z-score −1.982). angiogenesis, inhibited with 300 mg (z-score −1.021), while it is increased with 600 mg VASO-6 (z-score 1.447).

Increased nitric oxide in the blood stream leads to endothelial-dependent relaxation (EDR), which aids in the delivery of oxygen to muscles, subsequently increase ATP production and nutrient delivery.

The pathway involved in nitric oxide signaling in the cardiovascular system showed a significant positive z-score (1.342) with 300 mg VASO-6™ treatment, suggesting increased activity/NO signaling, which is consisting with clinical findings. The proteins identified in the pathway: arginase 2 (Arg2), calmodulin like 5 (CALML5), heat shock protein 90 (Hsp90b1), mitogen-activated protein kinase kinase 1 (MAP2K1), mitogen-activated protein kinase kinase 2 (MAP2K2), and mitogen-activated protein kinase 3 (MAPK3).

MAP2K1, MAP2K2, and MAPK3 are involved in numerous pathways involved in the regulation of many biological functions. For example, ERK/MAPK signaling was also shown to have increased activity, as well as alpha-adrenergic signaling, and actin cytoskeleton signaling.

Oxidative phosphorylation had significant positive z-score in both 300 mg and 600 mg doses (2.236 and 2, respectively). Oxidative phosphorylation is the production of ATP using energy derived from the transfer of electrons in the electron transport in the mitochondria.

TABLE 6

Proteins identified in the Oxidative Phosphorylation Canonical Pathway. Values are ratios of LFQ intensity values corresponding to either the 300 mg or 600 mg dose compared with untreated control samples.

| Protein ID | Protein Name | 300 mg | 600 mg |
|---|---|---|---|
| UQCRQ | Ubiquinol-cytochrome c reductase complex | 32.967 | 22.153 |
| UQCRH | Ubiquinol-cytochrome c reductase hinge | 2.142 | 4.559 |
| NDUFB3 | NADH: ubiquinone oxidoreductase subunit B3 | 2.495 | NA |
| COX7A2 | Cytochrome c oxidase subunit 7A2 | 3.285 | NA |
| COX5B | Cytochrome c oxidase subunit 5B | 2.236 | NA |
| ATP5F1D | ATP synthase F1 subunit delta | NA | 5.214 |
| ATP5PF | ATP synthase peripheral stalk subunit F6 | NA | 5.054 |

These human aortic endothelial cell findings are fairly consistent with the clinical findings, suggesting an increase in NO and ATP production, as well as the increased activity of several pathways related to angiogenesis.

The best-characterized extracellular functions of ATP in humans is that it improves muscular performance include enhanced muscular contraction, increased vasodilation and the capacity to decrease pain perception. These effects are triggered when ATP binds to a specific set of adenosine receptors embedded within the cell membrane. This interaction between ATP and the adenosine receptor initiates certain cellular-signaling cascades that produce the aforementioned ergogenic outcomes. Collectively, these recently discovered roles of ATP indicate that ATP supplementation can produce performance-enhancing effects without requiring a high amount of ATP in the body.

TABLE 7 showing the effects and z-score for different functions and their medically relevant categories with 600 mg of VASO-6 ™

| Functions | Activation z-score | Action | Categories |
|---|---|---|---|
| angiogenesis | 1.447 | Up Regulated/ Increases | Cardiovascular System Development and Function, Organismal Development |
| formation | 1.195 | Up Regulated/ Increases | Embryonic Development, Organ Development, Organismal Development, Skeletal and Muscular System Development and Function, Tissue Development |
| formation | 1.387 | Up Regulated/ Increases | Cellular Development, Cellular Growth and Proliferation, Embryonic Development, Organ Development, Organismal Development, Skeletal and |

TABLE 7-continued showing the effects and z-score for different functions and their medically relevant categories with 600 mg of VASO-6 ™

| Functions | Activation z-score | Action | Categories |
|---|---|---|---|
| inflammation | −1.982 | Down Regulated/ Reduces | Muscular System Development and Function, Tissue Development Connective Tissue Disorders, Inflammatory Disease, Inflammatory Response, Organismal Injury and Abnormalities, Skeletal and Muscular Disorders |
| migration | 2.926 | Up Regulated/ Increases | Cardiovascular System Development and Function, Cellular Movement |
| vasculogenesis | 1.283 | Up Regulated/ Increases | Cardiovascular System Development and Function, Organismal Development |

TABLE 8 showing the effects and z-score for different function and their medically relevant categories for 300 mg of VASO-6 ™

| Diseases or Functions Claims | Functions | Activation z-score | Action | Categories |
|---|---|---|---|---|
| Inflammation of joint | inflammation | −0.655 | Down Regulated/Reduces | Connective Tissue Disorders, Inflammatory Disease, Inflammatory Response, Organismal Injury and Abnormalities, Skeletal and Muscular Disorders |
| Proliferation of endothelial cells | proliferation | 0.251 | Up Regulated/Increases | Cardiovascular System Development and Function, Cellular Development, Cellular Function and Maintenance, Cellular Growth and Proliferation, Organismal Development, Tissue Development |
| Migration of endothelial cells | migration | 0.37 | Up Regulated/Increases | Cardiovascular System Development and Function, Cellular Movement |
| Proliferation of smooth muscle cells | proliferation | 1.39 | Up Regulated/Increases | Cellular Development, Cellular Growth and Proliferation, Organ Development, Skeletal and Muscular System Development and Function, Tissue Development |
| Cell movement of smooth muscle cells | cell movement | 1.807 | Up Regulated/Increases | Cellular Movement, Skeletal and Muscular System Development and Function |

Figure 11:
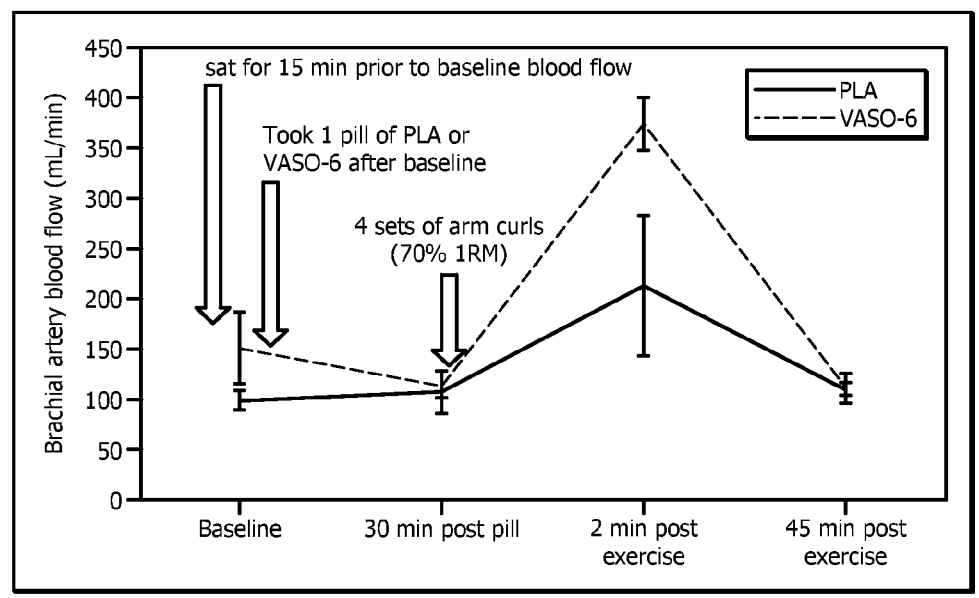
FIG. 11 depicts a graph showing the difference in brachial artery blood flow between placebo and VASO-6™.
Figure 12:
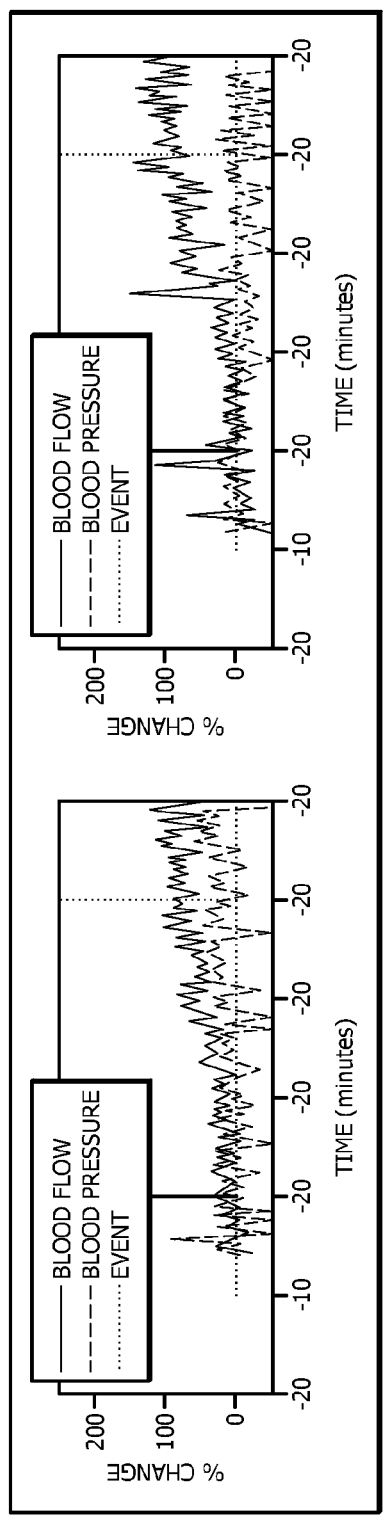
FIG. 12 depicts graphs showing changes in blood flow and blood pressure when a subject is given VASO-6™.

Human Subjects given placebo are compared to those given VASO-6™ with respect to brachial arterial blood flow at baseline, 30 min after taking drug, 2 min after exercise, and 45 min after exercise is depicted in FIG. 11. VASO-6™ shows a significant increase in blood flow, in comparison to placebo most clearly at 2 min after exercise. The approximate 78.6% approximate increase in blood flow with VASO-6™ is depicted in FIG. 11. The increase in muscular skeletal pump can also be seen in FIG. 12 which shows VASO-6™ synergizing the post exercise blood flow in these two subjects when given a 300 mg dose. This can be in part due to increases in muscular skeletal pump.

The pumping action of the heart propels the blood into the arteries, from an area of higher pressure toward an area of lower pressure. If blood is to flow from the veins back into the heart, the pressure in the veins must be greater than the pressure in the atria of the heart. Two factors help maintain this pressure gradient between the veins and the heart. First, the pressure in the atria during diastole is very low, often approaching zero when the atria are relaxed (atrial diastole). Second, two physiologic "pumps" increase pressure in the venous system. The use of the term "pump" implies a physical device that speeds flow. These physiological pumps are less obvious.

Skeletal Muscle Pump

Figure 13:
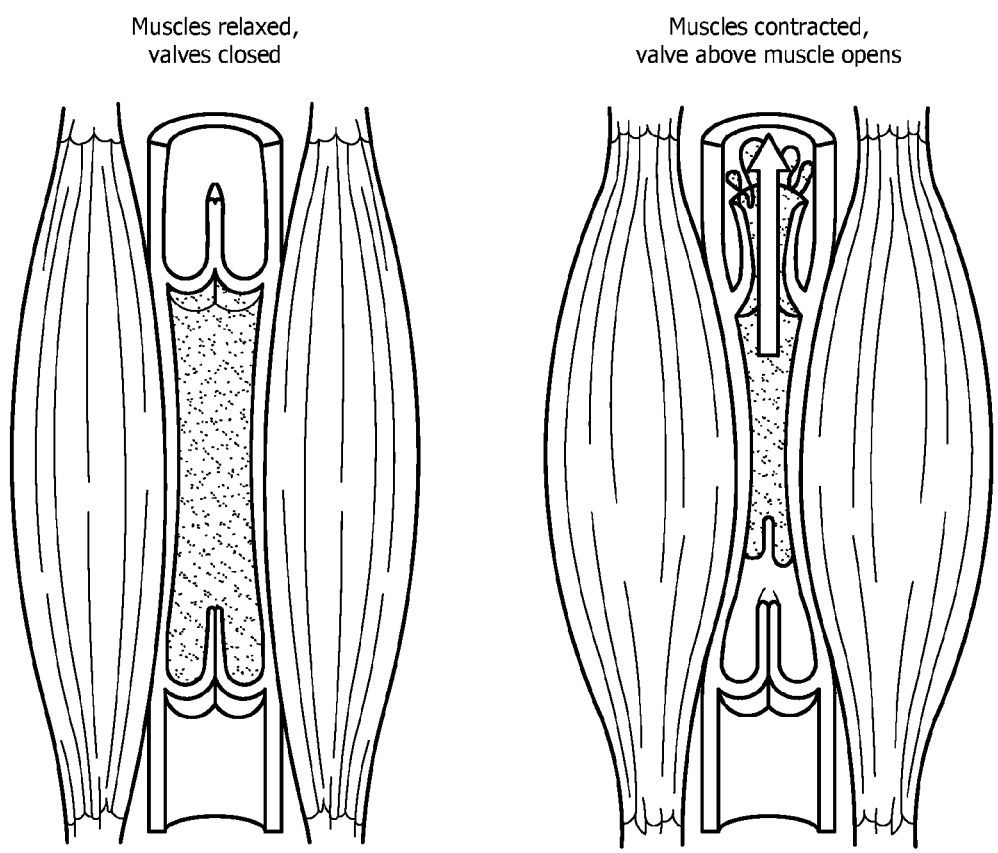
FIG. 13 depicts skeletal muscle pump, showing the contraction of skeletal muscles surrounding a vein compresses the blood and increases the pressure in that area. This action forces blood closer to the heart where venous pressure is lower. The importance of the one-way valves can be seen to ensure blood flows in the proper direction.

In many body regions, the pressure within the veins can be increased by the contraction of the surrounding skeletal muscle. This mechanism, known as the skeletal muscle pump (FIG. 13), helps the lower-pressure veins counteract the force of gravity, increasing pressure to move blood back to the heart. As leg muscles contract, for example during walking or running, they exert pressure on nearby veins with their numerous one-way valves. This increased pressure causes blood to flow upward, opening valves superior to the contracting muscles so blood flows through. Simultaneously, valves inferior to the contracting muscles close; thus, blood should not seep back down toward the feet. Military recruits are trained to flex their legs slightly while standing at attention for prolonged periods. Failure to do so may allow blood to pool in the lower limbs rather than returning to the heart. Consequently, the brain will not receive enough oxygenated blood, and the individual may lose consciousness. The use of VASO-6™ enhances skeletal muscle pump in part as evidenced by FIG. 12.

Benefits of Increased Blood Flow for Exercise

An increase in blood flow or circulation in the human body can help benefit the heart and the body's muscles and arteries throughout the body. Increased blood circulation improves oxygen rich blood flow to extremities. https://www.livestrong.com/article/323211-benefits-of-increased-blood-circulation. A subject may experience an increase in blood flow to vital organs when oxygen levels in blood are improved by exercising muscles and working out. Working out muscles and increasing aerobic activity can help with blood circulation.

Benefits of Regulated Blood Pressure During Exercise

The lower HR, blood pressure, and ventilatory responses to human exercise at a given workload with a trained skeletal muscle suggest that factors within the contracting skeletal muscle contribute to a lower sympathetic activation during exercise. Changes in skeletal muscle lactate and K+ concentrations and pH are likely to contribute to these changes by altering afferent feedback, whereas the markedly lower interstitial ATP concentrations during exercise with the previously immobilized leg suggest that interstitial ATP contributes to blood flow regulation in other ways than by simulating muscle afferents. The similar CO and O2 delivery, despite an 8% to 14% lower HR and blood pressure during exercise with the trained leg, suggest that adaptations within the skeletal muscles can result in ≈20% lower myocardial work during exercise without compromising O2 delivery and aerobic metabolism. http://hyper.ahajournals.org/content/hypertensionaha/61/5/1126.full.pdf.

Negative Effects of High Blood Pressure and Exercise

When the heart is put under stress during exercise, it is considered healthy. Yet stress due to high blood pressure is bad for the heart. Researchers have obtained new findings which indicate that a previously undetected signal pathway causes or protects from heart failure—depending on the type of stress. https://www.sciencedaily.com/releases/2018/01/180109125224.htm.

The canonical pathways in which GEO leads to up regulation of the pathway include: Actin Cytoskeleton Signaling; CD28 Signaling in T Helper Cells; Chemokine Signaling; CREB Signaling in Neurons; CXCR4 Signaling; Ephrin Receptor Signaling; ERK/MAPK Signaling; Fcγ Receptor-mediated Phagocytosis in Macrophages and Monocytes; fMLP Signaling in Neutrophils; GNRH Signaling; GP6 Signaling Pathway; Gα12/13 Signaling; Gαq Signaling; Gαs Signaling; IL-6 Signaling; IL-8 Signaling; Insulin Receptor Signaling; Integrin Signaling; Melatonin Signaling; Nitric Oxide Signaling in the Cardiovascular System; Noradrenaline and Adrenaline Degradation; NRF2-mediated Oxidative Stress Response; Oncostatin M Signaling; Oxidative Phosphorylation; P2Y Purigenic Receptor Signaling Pathway; p70S6K Signaling; PAK Signaling; Phospholipase C Signaling; PI3K Signaling in B Lymphocytes; PI3K/AKT Signaling; Production of Nitric Oxide and Reactive Oxygen Species in Macrophages; Protein Kinase A Signaling; Rac Signaling; RANK Signaling in Osteoclasts; Regulation of Actin-based Motility by Rho; RhoA Signaling; Signaling by Rho Family GTPases; Synaptic Long Term Potentiation; Telomerase Signaling; α-Adrenergic Signaling.

Actin Cytoskeleton Signaling

The actin cytoskeleton plays an important role in dynamic processes such as cell motility, axon guidance, cytokinesis and phagocytosis. Cell movements are the result of adhesion, loss of attachment and successive re-adhesion of filopodia and lamellipodia. These cellular remodeling requires precise regulation of actin filament assembly/disassembly and organization. Multiple signaling pathways control the rearrangements of the actin cytoskeleton. Members of the Rho family of small GTPases, including RhoA, Cdc42 and Rac, are activated by various classes of transmembrane receptors, such as Integrin receptors, Receptor tyrosine kinase, G protein-coupled receptors, and transmit signals to their downstream effector proteins involved in cytoskeletal regulation. RhoA is implicated in the formation of actin stress fibers, focal adhesion and actinomyosin assembly. RhoA binds and activates Rho kinase (ROCK), which has several downstream cytoskeletal targets. ROCK increases myosin light chain (MYL) phosphorylation by directly phosphorylating MYL and by inhibiting the myosin light chain phosphatase (MLCP), leading to actinomyosin assembly. ROCK also phosphorylates LIM-kinase (LIMK), which subsequently phosphorylates the actin depolymerizing protein, cofilin, inhibiting its function.

Cofilin inhibition leads to stabilization of actin. In addition, ROCK increases the activity of the Na+/H+ exchange protein NHE1 and the PI4P5K, potentiating stress fiber formation and focal adhesion assembly. On the other hand, integrin ligation stimulate the c-Src-dependent activation of GRLF1, which suppresses RhoA activity. The direct binding between integrins and FAK leads to the activation of the FAK-CAS-CRK-DOCK1-Rac pathway, which also antagonizes RhoA activity. Activated Rac and Cdc42 activate PAK which disassembles stress fibers and focal adhesion, through inactivation of MLCK and stabilizes actin filaments, through activation of LIMK. IQGAP is a scaffolding protein downstream of Rac and Cdc42, which promotes formation of adherens junctions. While RhoA causes the formation of stress fibers, stimulation of Rac, through the activation of WAVE and the Arp2/3-actin complex, induces the formation of lamellipodia and activation of Cdc42 leads to the formation of filopodia, through the binding to NWASP.

CD28 Signaling in T Helper Cells

CD28 is a co-receptor for the TCR/CD3 complex and is responsible for providing the co-stimulatory signal required for T-cell activation. Priming of naive T-cells in lymphoid organs depends on the interaction between CD28 on T-cells and both CD80 and CD86 on antigen presenting cells (APC), and induces subsequent IL-2 production and clonal expansion of T-cells for an effective cell-mediated immune response. CD28 is a major positive co-stimulatory molecule required for T-cell activation and functional differentiation, and upon ligation with CD80 and CD86, CTLA4 provides a negative co-stimulatory signal for the termination of activation and cellular function of T-cells. One of the important receptors on T-cells is CD45, which occurs as a component of a complex of proteins associated with the antigen receptor. CD45 can regulate signal transduction by modulating the phosphorylation state of tyrosine kinases such as Lck. Lck and Fyn remain attached to the cytoplasmic domain of either CD4 or CD8. Concomitantly, activation of Lck and Fyn phosphorylates ZAP70, SYK and Vav1. Activated Lck in turn activates CD28 and induces activation of LAT. LAT binds to a number of proteins, including GADS, SLP76, ITK, Vav1 and Tec. These interaction lead to the activation of PLC-γ,RLK,CARMA1,BCL10, CDC42 and Rac, thereby facilitating the recruitment of key signal transduction components to drive T-cell activation.

Further binding of CD28 to Class-I regulatory PI3K recruits PI3K to the membrane, resulting in generation of PIP3 and recruitment of proteins that contain a pleckstrin-homology domain to the plasma membrane, such as PIK3C3. PI3K is required for activation of AKT, which in turn regulates many downstream targets that to promote cell survival. In addition to NFAT, NF-κB has a crucial role in the regulation of transcription of the IL-2 promoter and anti-apoptotic factors. For this, PLC-γ utilizes PIP2 as a substrate to generate IP3 and DAG. IP3 elicits release of Ca2+ via IP3R, and DAG activates PKC-θ. Under the influence of RLK, PLC-γ, and Ca2+; PKC-θ regulates the phosphorylation state of IKK complex through direct as well as indirect interactions. Moreover, activation of CARMA1 phosphorylates BCL10 and dimerizes MALT1, an event that is sufficient for the activation of IKKs.

The two CD28-responsive elements in the IL-2 promoter have NF-κB binding sites. NF-κB dimers are normally retained in cytoplasm by binding to inhibitory l-κBs. Phosphorylation of I-κBs initiates its ubiquitination and degradation, thereby freeing NF-κB to translocate to the nucleus. Likewise, translocation of NFAT to the nucleus as a result of calmodulin-calcineurin interaction effectively promotes IL-2 expression. Activation of Vav1 by TCR-CD28-PI3K signaling connects CD28 with the activation of Rac and CDC42, and this enhances TCR-CD3-CD28 mediated cytoskeletal re-organization. Rac regulates actin polymerization to drive lamellipodial protrusion and membrane ruffling, whereas CDC42 generates polarity and induces formation of filopodia and microspikes. CDC42 and Rac GTPases function sequentially to activate downstream effectors like WASP and PAK1 to induce activation of ARPs resulting in cytoskeletal rearrangements. CD28 impinges on the Rac/PAK1-mediated IL-2 transcription through subsequent activation of MEKK1, MKKs and JNKs. JNKs phosphorylate and activate c-Jun and c-Fos, which is essential for transcription of IL-2. Signaling through CD28 promotes cytokine IL-2 mRNA production and entry into the cell cycle, T-cell survival, T-Helper cell differentiation and Immunoglobulin isotype switching.

Chemokine Signaling

The chemokines are a family of proinflammatory cytokines that act through cell surface receptors to regulate numerous cellular processes. Chemokines exert their effects through G protein-coupled receptors (GPCRs) which are relatively non-selective in their ligand binding. As a result of this promiscuity, many chemokine receptors bind more than one chemokine with high affinity. Chemokines are classified into four subfamilies according to the pattern of conserved cysteines in their amino acid sequences. They include CC chemokines, CXC chemokines, C chemokines and CX3C chemokines. The nomenclature of the chemokine receptors follows the notation used for the chemokine subfamilies.

Intracellular signaling by chemokine receptors depends on coupling to heterotrimeric G-proteins. During ligand binding, chemokine receptors associate with G-proteins, facilitating the exchange of guanosine diphosphate (GDP) for guanosine triphosphate (GTP). Activation of CXCR4 and CCR5 receptors for e.g. couple and activate Gq proteins. In the active state, G-proteins dissociate into Gα and Gβsubunits; the latter are able to activate the membrane-associated enzyme phospholipase Cβ2 which in turn results in the production of phosphatidylinositol 1, 4, 5-triphosphate (IP3) and diacyl-glycerol (DAG)). IP3 mobilizes calcium from intracellular stores, whereas DAG acts in conjunction with calcium to activate various isoforms of protein kinase C (PKC). The activation of PKC and of various calcium-sensitive protein kinases e.g. calmodulin kinase (CAMK)catalyze protein phosphorylation which triggers a series of signaling events that eventually leads to cellular responses. One such example is the PKC mediated activation of the focal adhesion kinase PYK2, which in turn triggers the mitogen activated protein kinase (MAPK) pathway, resulting in the further production of chemokines.

The chemokine receptor CCR3 is activated by several ligands e.g. eotaxin, monocyte chemotactic peptide 3 (MCP-3), MCP-4, and Regulated on activation normal T cell expressed and secreted (RANTES). The ligand Eotaxin plays an important role in the inflammatory response of eosinophils involving intracellular calcium release, production of reactive oxygen species and changes in actin polymerization through pathway involving Gi proteins. The activation of PLCγ by Gi α results in the production of IP3 and DAG, which trigger RHO kinase and PKC respectively. RHO and its downstream kinase-Rho-associated coiled-coil forming protein kinase (ROCK) regulate actin stress fiber formation and are required for eosinophil chemotaxis. Activated PKC on the other hand is responsible for ROS production in eosinophils. Following CCR3 activation, extracellular signal regulated kinase (ERK) is regulated through the phosphatidylinositol 3 kinase-gamma-(PI3Kγ)/RAS/RAF-1 pathway resulting in ROS production.

This pathway highlights some important molecular events involved in chemokine receptor signaling.

CREB Signaling in Neurons

The process of consolidating a new memory and the dynamic complexity of information processing within neuronal networks is greatly increased by activity-dependent changes in gene expression within individual neurons. A key paradigm of such regulation is the activation of the nuclear transcription factor CREB (cAMP responsive element binding protein) and its family members the ATF (activating transcription factor) and CREM (cAMP response element modulator). CREB can form homodimers or heterodimers with other members of the ATF family. Heterodimerization of CREB decreases its stability and CRE (cAMP Responsive Element) binding affinity. Activation of CREB leads to a variety of biological responses such as neuronal excitation, long-term memory formation, neural cell proliferation, and opiate tolerance.

The crucial event in the activation of CREB is the phosphorylation of Ser133 in its kinase-inducible domain (KID). Ser133 phosphorylation of CREB can be caused by kinases like PKA, CaMK and p70S6K in response to electrical activity, growth factors, neurotransmitter or hormone action on GPCR, or by neurotrophin effects on RTKs. In the nucleus, activated CREB results in the recruitment of the transcriptional coactivators CBP and p300. Elk1 is a part of a Ternary Complex Factor (TCF) that activates RSKs and binds SRF to the SRE. Phosphorylation of Elk1 increases its transcriptional ability to form ternary complexes with SRF at the SRE in the promoter region of many genes, such as c-Fos. CBP/p300 stimulates gene expression by interacting with components of the general transcriptional machinery or by promoting the acetylation of specific lysine residues in nucleosomes located near transcriptionally active promoters thus creating access to the gene for the basal transcriptional machinery. The basal transcriptional machinery includes TBP, TFIIB, and RNA Pol-II. The accumulation of cAMP in response to activation of GPCR also induces PLC-γ that catalyzes the formation of DAG, a PKC activator through phosphatidylinositols (PI). PI3K is responsible for activation of Akt/PKB which directly or indirectly affects CREB.

In the presynaptic terminal, metabotropic Glutamate Receptors Group-I (GLUR) augment glutamate release via interaction of PKC and PKA whereas Group-II/III Receptors inhibit glutamate release. In the postsynaptic striatal neurons, group-I receptors increase PKC activity as well as intracellular Ca2+ levels from internal store via PLC/DAG and PI/IP3 pathways, respectively. Activated PKC induces an increase in extracellular Ca2+ influx through phosphorylation of iGluR. Elevation of Ca2+ through calcium channels upregulates Ca2+-dependent CaMK-II/ERK1/2 signaling cascades resulting in CREB and Elk1 phosphorylation. In contrast, group-II/III receptors suppress the Ca2+ cascades by inhibiting AC coupling to GPCRs such as dopamine receptors.

The cAMP/CREB signaling pathway has been strongly implicated in cell proliferation and survival, glucose homeostasis, spermatogenesis, circadian rhythms and the synaptic plasticity that is associated with a variety of complex forms of memory including spatial and social learning indicating that CREB may be a universal modulator of processes required for memory formation.

Ephrin Receptor Signaling

The Eph receptors consist of the largest group of receptor tyrosine kinases, which bind to the ephrins, a family of cell surface associated ligands. The ephrin-Eph receptor complexes influence cell behavior such as attraction/repulsion, adhesion/de-adhesion implicated in axon guidance, cell migration, angiogenesis and synaptic plasticity.

The ephrins are divided into two subclasses, the ephrin A subclass contains ephrin A1 to A5, which are tethered to the cell membrane by a GPI anchor. The ephrin B subclass contains ephrin B1 to B3, which have transmembrane domain followed by a short cytoplasmic tail. The Eph receptors are also divided into two subclasses (Eph A1 to A8) and (EphB1 to B4, EphB6) based on their sequence similarity and ligand affinity. EphA receptors typically bind to most ephrin A ligands and EphB receptors bind most of the ephrin B ligands, with the exception of EphA4, which binds both ephrin A and B ligands.

These ephrin-Eph complexes are unique in the receptor tyrosine kinase family in that their signaling is bi-directional, propagating downstream signaling in the Eph receptor bearing cells (forward signaling) and in the cells expressing ephrins (reverse signaling).

Forward signaling: upon ephrin engagement, each member of the Eph receptor dimer auto- and transphosphorylates several tyrosine residues in their cytoplasmic domain. This phosphorylation creates binding sites for SH2 domains of several adaptor proteins. EphA receptors can directly activate Rho GTPases through the exchange factor Ephexin. The activation of Rho and its downstream effectors induced growth cone collapse, axon repulsion, and cell repulsion. EphA receptors can also inhibit or promote integrin-mediated adhesion through FAK. EphB receptors interact with different exchange factors, intersectin and kalirin. The intersectin-Cdc42-WASP-actin and kalirin-Rac-PAK-actin pathways regulate cytoskeleton dynamics leading to dendritic spines morphogenesis. EphB receptors can also promote integrin-mediated adhesion through the NCK-NIK pathway and the SHEP1-CAS-CRK-C3G-RAP1 pathway. Furthermore, EphB receptors activate Src, which phosphorylates NMDA receptors and increases calcium influx, having an effect on synaptic plasticity. Both EphA and EphB can negatively regulate the Ras-MAPK pathway downstream of other receptors, such as integrins or receptor tyrosine kinases (VEGFR, PDGFR, EGFR), affecting cell proliferation and axon guidance.

Reverse signaling: upon receptor engagement, ephrin A ligands activates FYN, which regulate cell morphology and integrin-mediated adhesion. Upon binding to an EphB receptor, ephrin B ligands are phosphorylated on cytoplasmic tyrosine residues by Src. Adaptor protein GRB4 is then recruited and initiates signaling pathways that regulate cytoskeleton dynamics and lead to disassembly of focal adhesions. Ephrins B binds constitutively to RGS3, which links G-protein-coupled receptors to ephrin-Eph receptor signaling.

ERK/MAPK Signaling

The ERK (extracellular-regulated kinase)/MAPK (mitogen activated protein kinase) pathway is a key pathway that transduces cellular information on meiosis/mitosis, growth, differentiation and carcinogenesis within a cell. Membrane bound receptor tyrosine kinases (RTK), which are often growth factor receptors, are the starting point for this pathway. Binding of ligand to RTK activates the intrinsic tyrosine kinase activity of RTK. Adaptor molecules like growth factor receptor bound protein 2 (GRB2), son of sevenless (SOS) and Shc form a signaling complex on tyrosine phosphorylated RTK and activate Ras. Activated Ras initiates a kinase cascade, beginning with Raf (a MAPK kinase kinase) which activates and phosphorylates MEK (a MAPK kinase); MEK activates and phosphorylates ERK (a MAPK). ERK in the cytoplasm can phosphorylate a variety of targets which include cytoskeleton proteins, ion channels/receptors and translation regulators.

ERK is also translocated across into the nucleus where it induces gene transcription by interacting with transcriptional regulators like ELK-1, STAT-1 and -3, ETS and MYC. ERK activation of p90RSK in the cytoplasm leads to its nuclear translocation where it indirectly induces gene transcription through interaction with transcriptional regulators, CREB, c-Fos and SRF.

RTK activation of Ras and Raf sometimes takes alternate pathways. For example, integrins activate ERK via a FAK mediated pathway. ERK can also be activated by a CAS-CRK-Rap1 mediated activation of B-Raf and a PLCγ-PKC-Ras-Raf activation of ERK.

Fcγ Receptor-Mediated Phagocytosis in Macrophages and Monocytes

Phagocytosis is a host cell endocytic response to particulate matter like bacteria. Avidly phagocytic cells, like macrophages and neutrophils, are an early line of defense against invading bacteria. The process of phagocytosis is complex and comprises of several events like particle binding, receptor clustering, actin nucleation, pseudopod extension, membrane recycling and phagosome closure. The Fc gamma receptors (FcγR; subtypes FcγR1A, FcγRIIA and FcγRIIIA) of the immunoglobulin superfamily are the best characterized receptors for phagocytosis in macrophages and monocytes. The activated receptors signal via immunoreceptor based tyrosine activation motifs (ITAM) which are present either in the cytosolic domain of the receptor (FcγRIIA), in an associated γ(FcγR1A and FcγRIIIA) or ζ (FcγIIIA) subunit.

Binding of IgG opsonized particles to the FcγR results in its activation and tyrosine phosphorylation of the associated ITAM. This phosphorylation is probably mediated by members of the SRC kinase family like FGR. Phosphorylated ITAM creates a binding site for the SRC kinase members like LYN and HCK and the spleen tyrosine kinase (SYK). It is thought that many downstream effectors are triggered by these kinases. Actin assembly is a crucial early step in phagocytosis and is triggered by G proteins like RAC and cell division cycle 42 protein (CDC42) by the activation of the actin related protein 2/3 (ARP2/3) complex and p21 activated kinase (PAK1). RAC in turn can be activated by the guanine nucleotide exchange factor (GEF) DOCK180 and adaptor protein CRKII. Other important promoters of actin assembly include ADP-ribosylation factor 6 (ARF6), protein kinase B (PKB/AKT) and protein tyrosine kinase 2 beta (PYK2). Local polymerization of actin filaments is required for the protrusion of pseudopodia that eventually internalize the particle. A large molecular complex consisting in part of vasodilator-stimulated phosphoprotein (VASP), the Fyn-binding/SLP-76-associated protein (FYB/SLAP), Src-homology-2 (SH2)-domain-containing leukocyte protein of 76 kD (SLP-76), non-catalytic region of tyrosine kinase (NCK), and the Wiskott-Aldrich syndrome protein (WASP) is recruited to the nascent phagosome and plays a crucial role in actin polymerization and pseudopod extension. In addition to actin, structural proteins like talin, ezrin and myosin are also recruited to the nascent phagosome.

Phagosome closure and particle internalization are important steps towards the formation of the mature phagosome. Phosphoinositide 3 kinase (PI3K), a down stream target of SYK, participates in nascent phagosome closure; this PI3K signal is amplified by Grb2 associated binder 2 (GAB2). Another target of FcγR activation is protein kinase C (PKC), which via the activation of phospholipase C A2 (PLC-A2) and formation of arachidonic acid, promotes phagosome closure and membrane fusion. Several other FcγR activated proteins play key roles in the formation of the mature phagosome: e.g. phospholipase C gamma 1 (PLC-γ1) and phospholipase D (PLD) in particle internalization; G protein RAB11 and vesicle-associated membrane protein 3 (VAMP3) in membrane recycling and remodeling. Structural proteins that are associated with the mature, actin depleted phagosome include myosin and ezrin.

This pathway highlights the important molecular events during FcγR activation in macrophages and monocytes.

fMLP Signaling in Neutrophils

Neutrophils play an important role in the host defense by invading microbial pathogens. Upon infection neutrophils become activated through interaction with chemo attractants and cytokines. These ligands bind to a variety of cell surface receptors, including heterotrimeric GPCR for N-formyl-Met-Leu-Phe (fMLP) and Platelet Activating Factor (PAF), and tyrosine kinase-associated receptors for GMCSF. Receptor activation triggers intracellular signal transduction pathways, resulting in the correct biological response, for instance, migration, phagocytosis, antibody-dependent cell mediated cytotoxicity, degranulation, superoxide production, transcriptional activation, and actin reorganization. When G-protein is blocked by pertussis toxin, cells do not respond to fMLP. Improper functioning of neutrophils is implicated in the pathogenesis of a variety of inflammatory diseases resulting in tissue damage.

fMLP receptor expression is upregulated by various cytokines. The human fMLP receptor shows sequence homology to the receptor of IL-8 (Interleukin-8). Granulocytes and mononuclear cells are the conventional target for fMLP actions. fMLP signal transduction pathways lead to biosynthesis of the prostanoid. Activation of PLC-β results in production of the intracellular second messengers DAG and IP3. These second messengers activate PKC; mobilize Ca2+ from intracellular stores, which regulate Calm (Calmodulin) and calcineurin. Calcineurin activates the transcription factor NFAT (Nuclear Factor of Activated T-Cells), which contributes to activation of chemokine genes. PKC leads to NF-κB activation and I-κB (Inhibitor of κ Light Chain Gene Enhancer in B-Cells) degradation. Activation of MAPK (Mitogen Activated Protein Kinase) cascades leads to ERK1/2 (Extracellular Signal-Regulated Kinase) dependent p47Phox phosphorylation as well as activation of the Elk1 transcription factor and chemokine gene expression. fMLP receptor ligands also activate the multisubunit enzyme NADPH oxidase, which produces ROS (Reactive Oxygen Species) rapidly released in the respiratory burst. One of the components of the NADPH (Nicotinamide Adenine Dinucleotide Phosphate) oxidase is p47Phox.

In granulocytes a short exposure to fMLP induces actin polymerization, membrane ruffling, and cell polarization leading to cell migration toward a concentration gradient. The FPR (Formyl Peptide Receptor) activates proteins that are implicated in actin reorganization such as Rho family GTPases. PI3K (Phosphatidylinositiol-3 Kinase) activity is induced during leukocyte motility by GPCR and tyrosine kinase receptors. Activated CDC42 sets in motion signaling pathways leading through Rac, and presumably phosphoinositide synthesis to actin filament barbed-end uncapping and maximal catalytic activity of WASP (Wiskott-Aldrich Syndrome Protein) family proteins activated by GTP-CDC42. Active WASP proteins in turn cause the ARP2/3 (Actin-Related Proteins) complex to promote actin nucleation.

The receptor agonist fMLP is used as a general-purpose agent to induce cell activation of granulocytes. The stimulatory activity of fMLP is influenced negatively by IL-1 and positively by TNF-α. fMLP is a strong chemoattractant and, among other things, induces adherence, degranulation and production of tissue-destructive oxygen-derived free radicals in phagocytic cells. Endogenous fMLP is produced in both physiological and pathological conditions. As regards human pregnancy, fMLP causes an enhancement of amniotic Ptg (Prostaglandin) release. fMLP-activated granulocytes and mononuclear cells release cytokines that, in turn, stimulate PGE2 production from amnion cells. fMLP and fMLP antagonists represent new tools in the future management of premature labor, a major cause of maternal and fetal morbidity and mortality.

GNRH Signaling

Neutrophils play an important role in the host defense by invading microbial pathogens. Upon infection neutrophils become activated through interaction with chemo attractants and cytokines. These ligands bind to a variety of cell surface receptors, including heterotrimeric GPCR for N-formyl-Met-Leu-Phe (fMLP) and Platelet Activating Factor (PAF), and tyrosine kinase-associated receptors for GMCSF. Receptor activation triggers intracellular signal transduction pathways, resulting in the correct biological response, for instance, migration, phagocytosis, antibody-dependent cell mediated cytotoxicity, degranulation, superoxide production, transcriptional activation, and actin reorganization. When G-protein is blocked by pertussis toxin, cells do not respond to fMLP. Improper functioning of neutrophils is implicated in the pathogenesis of a variety of inflammatory diseases resulting in tissue damage.

fMLP receptor expression is upregulated by various cytokines. The human fMLP receptor shows sequence homology to the receptor of IL-8 (Interleukin-8). Granulocytes and mononuclear cells are the conventional target for fMLP actions. fMLP signal transduction pathways lead to biosynthesis of the prostanoid. Activation of PLC-β results in production of the intracellular second messengers DAG and IP3. These second messengers activate PKC; mobilize Ca2+ from intracellular stores, which regulate Calm (Calmodulin) and calcineurin. Calcineurin activates the transcription factor NFAT (Nuclear Factor of Activated T-Cells), which contributes to activation of chemokine genes. PKC leads to NF-κB activation and I-κB (Inhibitor of κ Light Chain Gene Enhancer in B-Cells) degradation. Activation of MAPK (Mitogen Activated Protein Kinase) cascades leads to ERK1/2 (Extracellular Signal-Regulated Kinase) dependent p47Phox phosphorylation as well as activation of the Elk1 transcription factor and chemokine gene expression. fMLP receptor ligands also activate the multisubunit enzyme NADPH oxidase, which produces ROS (Reactive Oxygen Species) rapidly released in the respiratory burst. One of the components of the NADPH (Nicotinamide Adenine Dinucleotide Phosphate) oxidase is p47Phox.

In granulocytes a short exposure to fMLP induces actin polymerization, membrane ruffling, and cell polarization leading to cell migration toward a concentration gradient. The FPR (Formyl Peptide Receptor) activates proteins that are implicated in actin reorganization such as Rho family GTPases. PI3K (Phosphatidylinositiol-3 Kinase) activity is induced during leukocyte motility by GPCR and tyrosine kinase receptors. Activated CDC42 sets in motion signaling pathways leading through Rac, and presumably phosphoinositide synthesis to actin filament barbed-end uncapping and maximal catalytic activity of WASP (Wiskott-Aldrich Syndrome Protein) family proteins activated by GTP-CDC42. Active WASP proteins in turn cause the ARP2/3 (Actin-Related Proteins) complex to promote actin nucleation.

The receptor agonist fMLP is used as a general-purpose agent to induce cell activation of granulocytes. The stimulatory activity of fMLP is influenced negatively by IL-1 and positively by TNF-α. fMLP is a strong chemoattractant and, among other things, induces adherence, degranulation and production of tissue-destructive oxygen-derived free radicals in phagocytic cells. Endogenous fMLP is produced in both physiological and pathological conditions. As regards human pregnancy, fMLP causes an enhancement of amniotic Ptg (Prostaglandin) release. fMLP-activated granulocytes and mononuclear cells release cytokines that, in turn, stimulate PGE2 production from amnion cells. fMLP and fMLP antagonists represent new tools in the future management of premature labor, a major cause of maternal and fetal morbidity and mortality.

GP6 Signaling Pathway

GPVI is a member of the immunoglobulin superfamily and is expressed in platelets and their precursor megakaryocytes. It serves as the major signaling receptor for collagen, which induces platelet activation and thrombus formation. GPVI can also be activated by laminin, fibrin, collagen-related peptide (CRP), convulxin, alborhagin and by low shear stress. The extracellular region of GPVI contains two Ig-like domains, which are responsible for collagen binding, and a short mucin-like Ser/Thr-rich stalk. GPVI is expressed on platelets in a mixture of monomeric and dimeric forms. The affinity of collagen for monomeric GPVI is too low to mediate activation, and dimeric GPVI is the active form with increased affinity.

Platelets abundantly express sheddases of the metalloproteinase (ADAM) family, which is used to regulate the function of adhesion and signaling receptors. The sheddase responsible for GPVI proteolysis is ADAM10. The association of calmodulin with GPVI inhibits the activation of ADAM10, and is regulated by calcium signaling, which plays a key role in overall platelet activation.

On the platelet plasma membrane, GPVI forms a complex with the homodimeric FcR-gamma. Each FcR-gamma chain contains one copy of an immunoreceptor tyrosine-based activation motif (ITAM) with two Tyr residues. Src family protein kinases Fyn and Lyn phosphorylate the ITAM Tyr residues which triggers GPVI-mediated signaling.

Phosphorylated FcR-gamma activates tyrosine kinase Syk, which leads to a cascade of protein phosphorylation events, phosphorylating the transmembrane adapter protein LAT, cytosolic adapter protein SLP76 and GADs and other adaptor and effector proteins, which together form LAT signalosome. The recruitment and phosphorylation of these proteins leads to the activation of phospholipase PLC-gamma-2 which cleaves phosphatidylinositol 4,5-diphosphate (PIP2) into the second messengers 1,2-diacylglycerol (DG) and inositol 1,4,5-trisphosphate (IP3). IP3 binds to receptors in plasma and intracellular membranes, leading to the release of Ca2+, while DG is the activator molecule for protein kinase C (PKC). The accumulated Ca2+ and PKC contribute to integrin-mediated platelet activation, which induce thrombus formation.

The phosphoinositide 3-kinase (PI3K) phosphorylates PIP2, converting it into phosphatidylinositol 3,4,5-triphosphate (PIP3), which leads to platelet activation via Akt signaling and also supports the recruitment of the tyrosine kinase BTK to the membrane, which undergoes autophosphorylation subsequent to phosphorylation by Lyn. BTK is responsible for PLC-gamma-2 phosphorylation and protein tyrosine kinase 2 (PTK2) activation. PTK2 activation leads to dense granule secretion and also has an important role in platelet activation via intracellular ROS accumulation.

Gα12/13 Signaling

The G12 subfamily of heterotrimeric G proteins, comprising of Gα12 and Gα13, has been implicated as a signaling component in cellular processes ranging from cytoskeletal change to cell growth and oncogenesis. They stimulate mitogenic signaling pathways leading to the oncogenic transformation of fibroblast cell lines. Gα12 and Gα13 regulate cytoplasmic as well as nuclear signaling events through downstream targets such as Ras, Rac, Rho, and CDC42 leading to cytoskeletal reorganization and activation of MAPK, JNK, the Na+-H+ exchanger, c-Fos, SRE and transcriptional activation of specific primary response genes.

Gα12 and Gα13 induce Rho activation and Rho-dependent biological responses including stress fiber formation and focal adhesion assembly. Two novel RhoGEFs, PDZ-RhoGEF and LARG, interact with the activated α-subunits of G12/G13 and thus mediate GPCR-induced Rho activation. Gα12/13 stimulate small GTPases by stimulating specific GEFs, competing with GDIs, or inhibiting specific GAPs. Both Gα12 and Gα13 can physically interact with the RGS motif containing RhoGEF. Signal coupling between Gα13 and Rho involve RTKs such as EGFR and other non-receptor kinases. In contrast, the coupling between Gα12 and Rho is independent of any tyrosine kinases. Similarly, a role for BTK family of kinases in Gα12/13 coupling to Rho has been observed. Activated Rho induces the formation of actin stress fibers and promotes the assembly of focal adhesions.

GPCRs that activate Rho and use Gα12 or Gα13 for signal transduction include receptors for lysophosphatidic acid, sphingosine 1-phosphate, thrombin, thromboxane A2 and the orphan receptor G2A. PYK2 is itself activated by Gα13, and to a lesser extent by Gα12. The RGS domain of Lsc blocks activation of PYK2 by Gα12 and Gα13. Gα12 also physically interacts with a novel RasGAP as well as BTK and stimulates their activity. Gα12/13 coordinates several critical signaling events through its interaction with the Ras and Rho family of GTPases. These include the regulation of different kinase modules as well as the activation of several transcription factors such as SRFs, TCFs, Jun and ATF2. In many cases it appears that different members of the MAPK family such as ERK5 or JNK are activated. This activation leads to regulation of gene expression. Gα13, besides directly interacting with and activating Rho, also engages the PI3K pathway to activate the protein kinase AKT and regulates NF-κB, through the activation of PYK2.

Gα12 and Gα13 also interact with the cytoplasmic domains of several members of the cadherin family of cell surface adhesion proteins, causing dissociation of the transcriptional activator from cadherins. Among proteins previously found to associate with the cadherin cytoplasmic region, β-Ctnn is a multi-functional protein that not only serves to link cadherin to the actin cytoskeleton, but also serves as a transcriptional activator. These findings provide a potential molecular mechanism for the cellular transforming ability of Gα12/13 subfamily, and reveal a link between heterotrimeric G-proteins and cellular processes controlling growth and differentiation.

Gαq Signaling

The heterotrimeric G-proteins are signaling molecules that transduce signals from a number of types of ligands such as hormones, neurotransmitters and chemokines. These extracellular signals are received by members of a large superfamily of receptors, the GPCRs, that activate the G-proteins, which then route the signals to several distinct intracellular signaling pathways. Heterotrimeric G-proteins are composed of an α, β, and γ subunit. Classically, G-proteins are divided into four families: G-αi/o, G-αs, G-αq/11, and G-α12/13, based on a similarity of their α-subunits. Each family consists of various members that often show very specific expression patterns. Members of one family are structurally similar and often share some of their functional properties. The G-αq/11 family of G proteins consists of 4 members: GNAQ, GNA11, GNA14 and GNA15/16. The α-subunits of Gq and G11 are almost ubiquitously expressed while the other members of this family such as G-α14 and G-α15/16 show a rather restricted expression pattern.

The G-αq pathway transduces signals from cell surface receptors that are activated by hormones such as angiotensin-II, endothelin-1, catecholamines, and prostaglandin F2-α to regulate diverse physiological functions. The most well characterized downstream molecule of G-αq is PLC-β, the activation of which leads to the production of intracellular messengers IP3 and DAG. IP3, which accumulates rapidly and transiently, binds to IP3R in the ER and activates calcium release from the ER lumen to the cytoplasm. Calcium signaling facilitates the activation of NFATc and axonal growth. Calcium release also activates PKC-mediated Raf/MEK/ERK signaling. G-αq, working through PKC appears to regulate various isoforms of PLD. PLDs catalyze the hydrolysis of phosphatidylcholine to produce phosphatidic acid and choline, which take part in cell activation. G-αq activates the transcription factor NF-κB through PYK2. Receptors transmitting signals through G-αq can promote Rho activation. ROCK acts downstream of Rho to regulate cytoskeletal rearrangements. G-αq activates CSK which in turn phosphorylates GSK3β thus playing a role in glycogen metabolism. Negative regulators of G-αq include the RGS proteins. G-protein mediated pathways interact with one another to form a network that regulates metabolic enzymes, ion channels, transporters, and other components of the cellular machinery controlling a broad range of cellular processes, including transcription, motility, contractility, and secretion.

Gαs Signaling

G-proteins are heterotrimers, consisting of an α, β, and γ subunit. They are involved in signal transduction for a number of types of ligands such as hormones, neurotransmitters and chemokines. These extracellular signals are received by members of a large superfamily of receptors, the GPCRs, that activate the G-proteins, which then route the signals to several distinct intracellular signaling pathways thus initiating changes in cell behavior. In the inactive heterotrimeric state, GDP is bound to the G-α subunit. Upon activation, GDP is released, GTP binds to G-α, and subsequently G-α-GTP dissociates from the G-βγ heterodimer and from the receptor. Both G-α-GTP and G-βγ are then free to activate downstream effectors. The duration of the signal is determined by the intrinsic GTP hydrolysis rate of the G-α-subunit and the subsequent re-association of G-α-GDP with G-βγ.

Four classes of heterotrimeric G-α proteins are found in eukaryotes: G-αi/o, G-αs, G-αq/11, and G-α12/13. As with all G-protein α-subunits, G-αs consists of two domains: a GTPase domain that is involved in the binding and hydrolysis of GTP and a helical domain that buries the GTP within the core of the protein. The G-αs family of G-proteins consists of 3 members: GNAS, GNASXL and GNAL. The most well characterized function of G-αs is in the regulation of adenylate cyclase (AC). Once active, AC produces the second messenger cAMP. The main downstream targets of cAMP are PKA and the GTP-exchange protein, EPACs. cAMP activates Rap1A through a PKA-independent and EPAC-dependent pathway. Rap1A activates the B-Raf/MEK/ERK pathway. A major target of PKA is the calcium channel RyR1. RyR1 function is modulated by proteins that bind to its large cytoplasmic scaffold domain, including PKA. Besides activating AC, G-αs also stimulates the kinase activity of Src and Hck, members of Src-family tyrosine kinases. G-αs binds to the catalytic domain and changes the conformation of Src, leading to increased accessibility of the active site to substrates. Src activated by direct interaction with GPCRs or components of the GPCR signaling machinery including G-αs is associated with the regulation of G-protein function, receptor desensitization, and endocytosis. The activity of the G-αs subunit can be markedly reduced by RGS proteins. RGS proteins are multifunctional, GTPase-accelerating proteins that promote G-αs subunit GTP hydrolysis, thereby directly terminating α subunit signaling and indirectly terminating the G-βγ dimer signaling through α subunit binding.

IL-6 Signaling

Interleukin 6 (IL-6) is considered a regulator of acute-phase responses and a lymphocyte stimulatory factor. The central role of IL-6 in inflammation makes it an important target for the management of infectious and inflammatory diseases. IL-6 responses are transmitted through Glycoprotein 130 (GP130), which serves as the universal signal-transducing receptor subunit for all IL-6-related cytokines.

IL-6-type cytokines utilize tyrosine kinases of the Janus Kinase (JAK) family and signal transducers and activators of transcription (STAT) family as major mediators of signal transduction. Upon receptor stimulation by IL-6, the JAK family of kinases associated with GP130 are activated, resulting in the phosphorylation of GP130. Several phosphotyrosine residues of GP130 serve as docking sites for STAT factors mainly STAT3 and STAT1. Subsequently, STATs are phosphorylated, form dimers and translocate to the nucleus, where they regulate transcription of target genes.

In addition to the JAK/STAT pathway of signal transduction, IL-6 also activates the extracellular signal-regulated kinases (ERK1/2) of the mitogen activated protein kinase (MAPK) pathway. The upstream activators of ERK1/2 include RAS and the src homology-2 containing proteins GRB2 and SHC. The SHC protein is activated by JAK2 and thus serves as a link between the IL-6 activated JAK/STAT and RAS-MAPK pathways.

The phosphorylation of MAPKs in response to IL-6 activated RAS results in the activation of nuclear factor IL-6 (NF-IL6), which in turn stimulates the transcription of the IL-6 gene. The transcription of the IL-6 gene is also stimulated by tumor necrosis factor (TNF) and Interleukin-1 (IL-1) via the activation of nuclear factor kappa B (NFκB).

This pathway highlights the important molecular components involved in IL-6 signaling.

IL-8 Signaling

Interleukin 8 (IL-8) is a member of the C-X-C family of chemokines that plays a central role in angiogenesis, tumor growth and inflammation. The cell surface receptors for IL-8 which are coupled to G proteins include CXCR1 (IL-8 receptor type 1) and the CXCR2 (IL-8 receptor type 2). While the CXCR1 is selectively activated by IL-8 only, CXCR2 responds to several additional chemokines. The IL-8 receptors are expressed on several cell types like neutrophils, endothelial cells, monocytes and tumor cells.

Angiogenesis is a multistep process including endothelial cell proliferation, migration, gap formation, capillary tube formation, endothelial cell survival and death. IL-8 plays a key role in many aspects during the early stages of the angiogenic process. Several kinases like Extracellular signal regulated kinase (ERK), p21 activated kinase (PAK) and LIM kinase are activated by IL-8 signaling and regulate the cytoskeletal response in angiogenesis. IL-8 also induces nuclear transcription factor-kappa B (NF-κB) through a TRAF6-dependent pathway, leading to the transcription of proangiogenic genes like ICAM and VCAM. The IL-8 mediated physical interaction between CXCR1, CXCR2 and vascular endothelial growth factor receptor (VEGFR) leads to the transactivation and phosphorylation of the latter, in a VEGF-independent manner. The formation of this complex results in the activation of Rho kinase (ROCK) which promotes endothelial gap formation. Similar to VEGFR, IL-8-induced transactivation of the EGFR is mediated by the CXCR2 and involves cathepsin B. Stimulation of EGFR leads to the activation of Phosphoinositide 3 kinase (PI3K) which facilitates endothelial cell migration. The upregulation of matrix metalloproteinase (MMP2 and MMP9) expression by IL-8 is another mechanism that leads to increased endothelial cell migration. Migration and gap formation in endothelial cells lead to increased vascular permeability.

Tumor growth and metastasis is related to neovascularization or angiogenesis within the tumor tissue. IL-8 upregulates the expression of genes involved in tumor growth (EGFR), angiogenesis (VEGF) and tumor invasion (MMP2 and MMP9). Additionally, IL-8 enhances cell proliferation by activating cyclin D via a protein kinase B (PKB/Akt) mediated mechanism.

Activation by IL-8 can trigger inflammation in cells like neutrophils leading to chemotaxis, the respiratory burst, granule release, and increased cell adhesion. The RAS/RAF/ERK1/2 pathway is activated by IL-8 resulting in neutrophil degranulation releasing proteins like myeloperoxidase (MPO) and defensins (HNP) that play an antimicrobial role. IL-8 activation of phospholipase D (PLD) triggers nucleotide adenosine phosphate dehydrogenase (NADPH) leading to respiratory burst. Chemotaxis is triggered by the several IL-8 activated kinases like PKB/Akt, focal adhesion kinase (FAK) and protein tyrosine kinase 2 (PYK2).

This pathway highlights the important components of IL-8 signaling.

Insulin Receptor Signaling

Insulin is an anabolic hormone essential for maintenance of whole-body glucose homeostasis, growth and development. Insulin regulates glucose homeostasis at many sites. It reduces hepatic glucose output via decreased gluconeogenesis and glycogenolysis and increases the rate of glucose uptake into striated muscle and adipose tissue. Insulin also profoundly affects lipid metabolism, increasing lipid synthesis in liver and fat cells, and controlling fatty acid release from triglycerides in fat and muscle.

Insulin action is initiated by binding to its cell surface receptor which is an α2β2 heterotetrameric complex. Once activated, the insulin receptor tyrosine phosphorylates a number of important proximal substrates including members of the insulin receptor substrate family (IRS1/2/3/4), the SHC adapter protein isoforms, Grb2-associated binder-1 (GAB-1) and the adapter protein CBL. Tyrosine phosphorylation of the IRS proteins creates recognition sites for additional effector molecules containing Src homology 2 (SH2) domains. These include the small adapter proteins GRB2 and NCK, which can trigger the RAS/Mitogen activated protein kinase (MAPK) pathway leading to cell growth. However, one of the most important targets of insulin receptor mediated phosphorylation is phosphatidylinositol 3-kinase (PI 3K).

Two classes of serine/threonine kinases are known to act downstream of PI 3-kinase, namely the serine/threonine kinase Akt, also known as protein kinase B (PKB), and the atypical protein kinase C isoforms zeta and gamma (PKCζ/γ). The activation of PKB results in the phosphorylation and activation of cyclic nucleotide phosphodiesterase (PDE) which is a regulator of cyclic adenosine monophosphate cAMP levels. As a result of the lower levels of cAMP, hormone sensitive lipase (HPL) is inhibited, thus decreasing lipolysis. AKT also inhibits the activity of Glycogen synthase kinase 3 (GSK3). This relieves the inhibition of ATP citrate lyase, thereby promoting fatty acid synthesis. In addition to its effects on lipid homeostasis, Insulin activated PKB phosphorylates and inhibits the tuberous sclerosis complex (TSC), which in turn is an inhibitor of mammalian target of rapamycin (mTOR)—a central regulator of protein synthesis. The inhibition of TSC thus leads to an enhancement of protein synthesis. In addition, insulin activation results in the translocation of PKB to the nucleus. where it regulates members of the Fork head family of transcription factors and promotes cell survival. In the cytoplasm PKB phosphorylates and inactivates components of the apoptotic machinery, including BAD. Thus, the PI3K/PKB pathway is an important component of insulin signaling.

One of the fundamental actions of insulin is to stimulate the uptake of glucose from blood into tissues. This uptake occurs via glucose transporters (GLUT). The most important GLUT in insulin action is GLUT4, which is localized in endosomal vesicles and is induced by insulin to translocate with the vesicle to the plasma membrane. Several proteins have been identified in association with the GLUT4 compartment and are known to be associated with GLUT4 at the plasma membrane. These include the vesicle-associated membrane protein 2 (VAMP2), which interacts with a target membrane SNAP receptor (t-SNARE) for e.g. syntaxin. Insulin mediated activation of PKC ζ induces serine phosphorylation of VAMP2 in the GLUT4 compartment, which in turn promotes GLUT4 vesicle transport to the plasma membrane and thereby increases glucose uptake.

This pathway highlights the key components of insulin signaling.

Integrin Signaling

Integrins are cell surface glycoproteins that are involved in cell-cell and cell-extracellular matrix (ECM) interactions. These interactions are the basis for a number of diverse effects that include cell migration and anchorage, cell growth and differentiation. Integrins are a family of more than 20 different cell surface receptors which are comprised of non-covalently associated α and β subunits. The ligands for integrins include the ECM proteins vitronectin, fibronectin and collagen.

Integrins have the property of attaching the cell to the ECM and the cytoskeleton to the cell membrane. In doing so, integrins are able to communicate changes in the external environment of the cell and translate them into structural changes within the cell. It is the cytoplasmic face of the Integrin β subunit that is responsible for interactions with cytoskeletal proteins like a actinin, talin, vinculin, zyxin and F-actin. Other key mediators of integrin signaling include Focal adhesion kinase (FAK) and integrin linked kinase (ILK). These proteins are important in the formation of focal adhesions, which are responsible for signal transduction and assembly of stress fibers.

Cytoskeletal remodeling is important in many cellular responses, including cell adhesion, spreading, and motility. Rho family members of small guanosine triphosphatases (GTPases)—RHO, RAC, and CDC42—have been implicated as critical regulators of cytoskeletal changes. The primary changes in cytoskeleton are brought about by interaction between actin and myosin. Myosin light chain kinase (MLCK) is the enzyme that phosphorylates and activates myosin light chain (MLC). MLCK is inhibited by p21 activated kinase (PAK) an effector molecule activated by RAC and CDC42. The inhibition of MLCK thus regulates cytoskeletal rearrangement. On the other hand, Rho-kinase (ROCK) an effector molecule of RHO phosphorylates myosin light chain phosphatase (MLCP) and inhibits the phosphatase activity. The inhibition of MLCP increases phosphorylation and activation of MLC, which then mediates the assembly of stress fibers and other cytoskeletal changes.

Integrins also trigger the activation of mitogen activated protein kinase (MAPK) pathways. Integrin mediated activation of PAK leads to the phosphorylation and activation of MAPK kinase MEK1. The activation of MEK1 leads to the downstream activation of Extracellular signal regulated kinase (ERK) which in turn activates MLCK promoting stress fiber formation. PAK is also involved in the activation of the MAPK c Jun kinase (JNK). In addition to PAK, another integrin activated kinase, FAK triggers the adapter protein SHC and signaling through the RAS/MAPK pathway leading to cell proliferation. Likewise, the Integrin mediated triggering of ILK leads to activation of a LIM domain containing protein PINCH which in turn activates a SH2/SH3 domain containing protein non-catalytic region of tyrosine kinase adaptor protein 2 (NCK2). NCK2 interacts with several growth factor pathways in addition to interacting with cytoskeletal proteins. Thus there are several integrin activated kinases that could serve as sites of convergence in the action of integrins and growth factors.

This pathway highlights the important components of integrin signaling.

Melatonin Signaling

Melatonin is a hormone secreted mainly by the pineal gland or epiphysis, and in small quantity by the retina. Dissemination of circadian information relies on the activation of melatonin receptors, which are most prominently expressed in the suprachiasmatic nucleus (SCN), and the hypophyseal pars tuberalis, but also in many other tissues. Melatonin can activate or inhibit signal transduction cascades through receptors or independent of receptors. The hormone binds with high affinity in the picomolar range to its plasma membrane receptors, and/or in the nanomolar range to nuclear receptors (RZR/ROR), as well as to calmodulin. At higher concentrations, melatonin exhibits a free radical scavenging function. Two of the melatonin receptors are GPCRs (MTNR1A and MTNR1 B), while the third belongs to the family of quinone reductases. MTNR1A and MTNR1B can couple to multiple signal transduction cascades, whereas the signaling cascades mediating the responses of the third receptor are yet to be elucidated.

Plasma membrane melatonin receptors are expressed mainly in the CNS, whereas RZR/ROR is prominently expressed both in the periphery and the brain. The action of plasma membrane receptors have been associated with circadian rhythmicity, whereas direct effects of melatonin in the periphery, such as immunomodulation, cellular growth, bone differentiation, and circadian rhythmicity mainly appear to be mediated by RZR. After binding to its plasma membrane receptors, melatonin changes the conformation of the a-subunit of specific intracellular G proteins. It regulates cell function via second messengers such as cAMP, Ca2+, cGMP, DAG, and arachidonic acid. Besides the cAMP-dependent cascade, MTNR1A can couple to a PLC-dependent signal transduction cascade directly or indirectly via G-βγ subunits for phosphoinositide turnover, and can also activate PKC signaling. On the other hand, activation of MTNR1A promotes ERK/MAPK signaling. These receptors can also modulate the formation of arachidonic acid and activation of JNK. In addition, several functional responses to melatonin are mediated by regulation of ion channels. Activation of MTNR1As potentiates vasoconstriction by blocking calcium-activated potassium channels in smooth muscle. This blockade may result from a decrease in cAMP and in phosphorylation of the potassium channels by PKA. Melatonins can also induce vasoconstriction in cerebral arteries through inhibition of potassium channels. MTNR1As also couple to the GIRK/Kir3 channels.

Similar to MTNR1A, activation of the MTNR1B by melatonin inhibits cAMP formation. Additionally, MTNR1B activation leads to the inhibition of cGMP formation through proteins upstream of guanylate cyclase such as NOS. In the SCN, melatonin increases PKC activity through activation of Gαq, which stimulates the PLC signaling cascade. Other responses of melatonin receptors include phase advance of circadian rhythms in the isolated SCN, enhancement of cell-mediated and humoral immunity, inhibition of leukocyte rolling in the microvasculature, and inhibition of proliferation of human choriocarcinoma cells, most likely by delay of G1 to S phase transition. Furthermore, activation of MTNR1B decreases the expression of the glucose transporter GLUT4, which in turn decreases glucose uptake in human brown adipocytes.

Melatonin binds to calmodulin with high affinity and acts as an antagonist of calmodulin-mediated CalmKII activation. Melatonin scavenges oxygen-centered free radicals, especially the highly toxic hydroxyl radical, and neutralizes them by a single electron transfer, which results in detoxified radicals. Melatonin has been proclaimed to be a cure-all for a wide variety of conditions, ranging from insomnia to cancer, to acting as an anti-aging agent.

Nitric Oxide Signaling in the Cardiovascular System

Nitric oxide (NO) is produced in the vascular system by endothelial nitric oxide synthase (eNOS), a Ca+2/calmodulin (CaM)-dependent enzyme. NO production is promoted by diverse agonists that transiently increase intracellular Ca+2 concentration and activate eNOS. For example, interaction of eNOS with caveolin, the structural scaffolding protein of caveolae reduces eNOS activity. The calveolin-eNOS complex undergoes cycles of association and dissociation modulated by Ca+2 concentrations. Other regulators of eNOS action include HSP90 and Akt which synergistically increase eNOS activity along with formation of a ternary complex comprised of HSP90, Akt, and CaM-bound eNOS.

In the heart, excitation-contraction (EC) coupling is driven by an ion-channel-mediated calcium cycle that produces myofilament contraction and relaxation. NO in the heart is able to regulate the activaty of ion channels like the L-type Ca(+2). These effects are mediated by cGMP, through the activity of three main proteins: the cGMP-dependent protein kinase (PKG), the cGMP-stimulated phosphodiesterase (PDE2) and the cGMP-inhibited PDE (PDE3). There is also evidence that NO may modulate the function of the ryanodine receptor Ca(2+) release channel (RyR2) on the cardiac sarcoplasmic reticulum.

Noradrenaline and Adrenaline Degradation

General Background The catecholamines dopamine, noradrenaline, and adrenaline function as neurotransmitters and hormones. They have important physiological regulatory roles and are involved in the development of many diseases. Overall, approximately half of the dopamine produced in the body is not converted to noradrenaline and is degraded to inactive metabolites (see pathway dopamine degradation). Although the degradation of endogenous catecholamines has been well studied, many inaccuracies based on early studies still remain in the literature. For example, noradrenaline degradation has been depicted as a series of reactions, including oxidative deamination, that form 3,4-dihydroxymandelate, followed by O-methylation to form vanillyl mandelate. However, updated pathways are shown in (Eisenhofer04) and here. Catecholamines are synthesized in both neuronal and non-neuronal cells, including the central nervous system, sympathetic nerves, adrenal medulla, gastrointestinal tract, and kidneys. They have previously been considered to be metabolized after their release from cells. They are now believed to be largely metabolized in the cells in which they are synthesized. In addition, intracellular catecholamines stored in vesicles were believed to be released extracellularly only upon stimulation. It is now thought that vesicular catecholamines are in a dynamic equilibrium with the cytoplasm. Outward leakage from vesicles is countered by active transport back into vesicles by monoamine transporters. The small amount of catecholamines remaining in the cytoplasm are a major source of metabolites. The metabolism of the transient (and toxic) aldehyde intermediates of catecholamine metabolism 3,4-dihydroxyphenylglycolaldehyde and 3,4-dihydroxyphenylacetaldehyde is dependent upon the presence (in noradrenaline and adrenaline) or absence (in dopamine) of the β-hydroxyl group. Its absence in dopamine and 3,4-dihydroxyphenylacetaldehyde favors oxidation by aldehyde dehydrogenase. Its presence in noradrenaline, adrenaline and 3,4-dihydroxyphenylglycolaldehyde favors reduction by aldehyde reductase, or aldose reductase. Thus, dopamine is preferentially converted to an acid metabolite, and noradrenaline and adrenaline are preferentially converted to an alcohol metabolite.

About This Pathway The major route of vanillyl mandelate production from noradrenaline and adrenaline is currently believed to involve initial oxidative deamination to the unstable aldehyde intermediate 3,4-dihydroxyphenylglycolaldehyde and reduction to 3,4-dihydroxyphenylglycol by aldehyde reductase or aldose reductase. These reactions occur mainly in neuronal tissue, whereas the O-methylation of noradrenaline and 3,4-dihydroxyphenylglycol occurs in extraneuronal tissues. 3,4-dihydroxyphenylglycol is O-methylated to 3-methoxy-4-hydroxyphenylglycol and this alcohol is dehydrogenated to the unstable aldehyde intermediate 3-methoxy-4-hydroxyphenylglycolaldehyde which is then dehydrogenated to vanillyl mandelate, the major end product of noradrenaline and adrenaline degradation. Alcohol dehydrogenase and aldehyde dehydrogenase play the major role in vanillyl mandelate production in liver. Vanillyl mandelate is excreted in urine. An alternative route following the oxidative deamination of noradrenaline and adrenaline to 3,4-dihydroxyphenylacetaldehyde is its dehydrogenation to 3,4-dihydroxymandelate, which was believed for many years to be the main route. It is now considered to be quantitatively insignificant under normal conditions and 3,4-dihydroxyphenylglycol is the main product (see above). Consequently, the O-methylation of 3,4-dihydroxymandelate to vanillyl mandelate is no longer considered to be the main source of vanillyl mandelate. Two minor routes that contribute to vanillyl mandelate production are via the O-methylation of noradrenaline and adrenaline to normetanephrine and metanephrine, respectively.

NRF2-Mediated Oxidative Stress Response

General Background The catecholamines dopamine, noradrenaline, and adrenaline function as neurotransmitters Oncostatin M Signaling Cytokines are the principal intercellular mediators of the tissue reaction to trauma and infection. Members of Interleukin 6 (IL-6) hematopoietic cytokine family include IL-6, IL-11, Leukemia Inhibitor Factor (LIF), Oncostatin M (OSM), Ciliary Neurotrophic Factor (CNF), Cardiotrophin-1, and Neurotrophin-1, and play a particularly prominent role in orchestrating initiation and progression of inflammation, hematopoiesis, acute phase response, bone and heart development as well as Neurogenesis. Their redundant effect is attributed to the shared use of the common signal transducing receptor chain GP130. GP130 is homodimerized by IL-6 and IL-11 upon binding to their ligand-specific α-receptors. The other cytokines of this family trigger the heterodimerization of GP130 with the LIFR or the OSMR. Human OSM has the capability to signal both via GP130-LIFR and GP130-OSMR heterodimers to form the high affinity, signaling-competent OSMRI or OSMRII.

OSM is produced by activated monocytes and lymphocytes and acts locally on stromal cells. Stromal cells in turn respond prominently by enhanced production of IL-6 and LIF. IL-6 and LIF enter into circulation and participate in the recruitment of systemic inflammatory response that includes the acute phase reaction of the liver. In bovine and human endothelial cells, OSM promotes the expression of urokinase plasminogen activator, basic FGF, GCSF, and GMCSF. In human fibroblasts, OSM modulates not only matrix metalloproteinases but also TIMP. OSM binds to a receptor shared with LIFR-β and GP130, and to a high affinity OSMR-β that binds only OSM and also involves the subunit GP130. The two receptors for OSM may be functionally different and they can be coupled to different signal transduction pathways. Ligand-induced oligomerization of receptor subunits activates JAKs, which in turn phosphorylate tyrosine residues in the receptor cytoplasmic domain. This phosphorylated tyrosine create docking sites for STAT1, STAT3, and STAT5, protein-tyrosine phosphatase SHP2, and linker proteins such as GAB1, GRB2, SOS, or SHC, which propagate the signal to other pathways such as MEK (MAPK/ERK Kinases), ERK1/2 (Extracellular Signal Regulated Kinase), JNK and PI3K. Receptor signaling is manifested by the activation of genes such as acute phase proteins or CDK inhibitor p21/WAF1, which is primarily activated through STATs and immediate early response genes such as c-Fos and c-Jun, primarily through ERK1/2. OSMR-β does not possess a phosphorylation site for ERK1/2 and, thus, do not appear to be appreciably influenced by activated ERK.

As a pleiotrophic cytokine, OSM is involved in regulation of the acute phase reaction, hematopoiesis, bone remodeling, and homeostasis of the extracellular matrix, and can act as a mediator for both the proliferation and the growth arrest of various cell lines. OSM inhibits the growth of many cancer cell types, including human melanoma, neuroblastoma, and fibrosarcoma. Due to its ability to induce TIMP1 and TIMP3, profibrotic properties have been attributed to this cytokine. Compared with other IL-6-type cytokines, OSM often induces stronger effects with regard to STAT and MAPK activation, induction of protease inhibitors or growth inhibition. In rheumatoid arthritis, OSM levels correlate with disease severity.

Oxidative Phosphorylation

Oxidative phosphorylation is the production of ATP using energy derived from the transfer of electrons in an electron transport system and occurs by chemiosmosis. The process is accomplished though oxidation-reduction reactions in the mitochondria. During oxidative phosphorylation, electrons are transferred from electron donors to electron acceptors, referred to as the electron transport chain. The flow of electrons from NADH to O2 through protein complexes located in the mitochondrial inner membrane leads to the pumping of protons out of the mitochondrial matrix. The resulting uneven distribution of protons generates a pH gradient and a transmembrane electrical potential that creates a proton-motive force. ATP is synthesized when protons flow back to the mitochondrial matrix through an enzyme complex (Complex V). The oxidation of fuels and the phosphorylation of ADP are coupled by the proton gradient across the inner mitochondrial membrane.

Oxidative phosphorylation consists of five protein-lipid enzyme complexes (Complex I-V) located in the mitochondrial inner membrane that contain flavins (FMN, FAD), quinoid compounds (coenzyme Q10, CoQ10) and transition metal compounds (iron-sulfur clusters, hemes, protein-bound copper). These enzymes are designated complex I (NADH:ubiquinone oxidoreductase, EC 1.6. 5.3), complex II (succinate:ubiquinone oxidoreductase, EC 1.3.5.1), complex III (ubiquinol:ferrocytochrome c oxidoreductase, EC 1.10.2.2), complex IV (ferrocytochrome c:oxygen oxidoreductase or cytochrome c oxidase, EC 1.9.3.1), and complex V (ATP synthase, EC 3.6.1.34). Complex I transports electrons from NADH to ubiquinone. Complex II catalyzes the oxidation of succinate to fumarate and transfers electrons to ubiquinone pool of respiratory chain. Complex III transfers electrons from ubiquinol to cytochrome c coupled with the transfer of electrons across inner mitochondrial membrane. Complex IV, the final step in the electron transport chain, is the reduction of molecular oxygen by electrons derived from cytochrome c. Complex V, the final enzyme in the oxidative phosphorylation pathway, couples a proton gradient generated by respiratory chain to ATP synthesis where protons flow from intermembrane mitochondrial space to the matrix.

P2Y Purigenic Receptor Signaling Pathway

Angiogenesis plays an important role in pathological events such as tumor growth, wound healing and psoriasis. Recent research reveals the contribution of purines and pyrimidines to this process. ATP, ADP, UTP, UDP and adenosine play pivotal signaling roles in these long-term events, mediated through P1 and P2 receptors. Specific to the P2 receptors, physiological effects can be exerted via receptor P2X, which are fast ionotropic receptors that function as cationic-gated channels, and P2Y which are GPCRs. These receptors are coupled to specific cellular functions as diverse as angiogenesis, neurotransmission, wound healing, morphogenesis and apoptosis.

The P2Y family consists of seven functional mammalian P2Y receptors: P2Y1, P2Y2, P2Y4, P2Y5, P2Y6, P2Y11, and P2Y12 with each member displaying ligand preferences and the ability to activate a variety of downstream signaling pathways. For example, P2Y1, P2Y2, P2Y4, P2Y6, and P2Y11 receptors are coupled to the activation of PLC, mobilization of intracellular Ca2+ and activation of PKC whereas the newly cloned P2Y12 receptor couples solely to the inhibition of AC. The P2Y11 receptor is dually coupled to the activation of PLC and AC.

P2Y receptors are expressed ubiquitously, but specific tissue responses are achieved by cell-specific expression profiles. For example, endothelial cells release ATP and UTP during shear stress and hypoxia which acts on P2Y1, P2Y2 and sometimes P2Y4 purinoceptors leading to the production of NO and subsequent vasodilation. ATP and UTP released from endothelial cells stimulate endothelial and smooth muscle cell proliferation via P2Y1, P2Y2, and P2Y4 receptors. Blood-borne platelets possess P2Y1 and P2Y12 ADP-selective purinoceptors. Activation of the P2Y1 receptor alone causes platelet shape change but no aggregation unless the P2Y12 receptor is activated concomitantly. This concomitant activation initiates signaling pathways that ultimately trigger the activation of GPIIB/IIIA which promotes high-affinity binding to fibrinogen and platelet aggregation. Mitogenesis/cell proliferation is another important function of P2Y receptors. P2Y2, P2Y4, P2Y6 and P2Y11 activate various other downstream signaling pathways including PI3K/AKT, PLC/Ca+2 and AC/PKA leading to the activation of transcription factors such as c-Fos, c-Jun, CREB and c-Myc. These factors regulate the expression of genes that are involved in cell proliferation. Since the P2Y receptors are coupled to multiple specific cellular functions, they have a tremendous potential in therapeutic applications.

p70S6K Signaling

The p70S6K protein is a Serine/Threonine kinase that phosphorylates the ribosomal S6 subunit, a component of the 40S subunit of eukaryotic ribosomes. It plays a role in protein synthesis and in cell growth control during G1 phase via enhanced translation of certain mRNA species. This enzyme has a complex regulation: phosphorylation by PDK1 at the activation loop is required for activation. Activity is also modulated by phosphorylation by ERK1 and ERK2 and dephosphorylation by phosphatases. The mTOR Serine/Threonine kinase is also required for full activation of p70S6K.

p70S6K is activated through a complex network of signaling molecules. The enzymatic activity of p70S6K is stimulated by GM-CSF in hematopoietic cell and neutrophils. The generation of 3-phosphoinositide lipid products by PI3K, which is activated in response to ligands such as angiotensin II, EGF, insulin and IGF1, is required for the phosphorylation of p70S6K by PDK1, AKT and mTOR. PI3K, which is important for activation of p70S6K, can be activated by several proteins. In thrombin signaling, binding of thrombin to its receptor PAR-1 leads to the activation of PI3K via Gαi. In B cells, identification of a novel B cell adaptor termed BCAP, has been reported to activate PI3K.

Mechanical stimuli activate p70S6K via mTOR signaling through a PLD-dependent increase in PA. The downstream mediator of AKT/p70S6K signaling regulates mRNA translation and cell cycle progression. Both AKT and p70S6K are capable of phosphorylating and inactivating BAD, thus regulating cell death.

mTOR controls multiple cellular functions in response to amino acids and growth factors. For effective mTOR-catalyzed p70S6K phosphorylation, the disruption of the ternary complex of mTOR-RAPTOR-p70S6K is necessary. AKT and p70S6K are actively involved in mediating cell adhesion. p70S6K regulates cell growth by inducing protein synthesis in response to cytokines. IL-4 activates p70S6K via PI3K and PKC-δ. The IL-4 receptors (IL-4Ralpha; and IL-4Rγ) induce JAK1 to activate IRS which in turn modulates PI3K.

p70S6K is also an important regulator of cell proliferation. Its activation by growth factors requires an ERK-dependent signal. Constitutive p70S6K activation occurs in some human malignancies and may contribute to dysregulated cell growth. FRAP-p70S6K signaling appears to be necessary for G1-S phase progression and proliferation in pancreatic cancer cells. Rapamycin, a specific inhibitor of p70S6K, inhibits functional chemotaxis which is induced by p70S6K through MAPK signaling.

p70S6K phosphorylates the 40S ribosomal protein S6, modulating the translation of an mRNA subset that encodes ribosomal proteins and translation elongation factors. p70S6K is activated in response to mitogenic stimuli and is required for progression through the G1 phase of the cell cycle and for cell growth. Besides S6, other important targets of p70S6K include the microtubule associated protein Tau. A p70S6K-modulated up-regulation of Tau translation might contribute to PHF-tau accumulation in neurons with neurofibrillary changes. p70S6K also phosphorylates Ser366 of eEF2K, causing inactivation which also leads to protein synthesis. Thus p70S6K is known for its role in modulating cell cycle progression, cell size and cell survival. In response to mitogen stimulation, p70S6K activation up-regulates ribosomal biosynthesis and enhances the translational capacity of the cell.

PAK Signaling

The p21 activated protein kinases (PAK) are a growing family of serine/threonine protein kinases which are activated in response to extracellular signals and regulate diverse cellular functions including cytoskeletal actin assembly, neurite outgrowth, cell cycle control and apoptosis.

The GTPase family proteins Cdc42 and Rac are the major activators of PAKs. The GTP bound forms of Cdc42 and Rac regulate assembly of the actin cytoskeleton, in part by stimulation of PAKs and in part by activation of the intermediate switch proteins, WASP and N-WASP. PAKs respond to receptor mediated signals that direct their recruitment to the plasma membrane followed by their activation. Major receptors that activate PAK signaling include RTK and integrins. Growth factors such as EGF bind and activate RTK such as EGFR which eventually results in activation of Ras. Ras then activates several effectors such as the ser/thr kinase Raf and PI3K. The PI3K pathway activates Cdc42 and Rac through Vav. Activated Cdc42 and Rac then activate PAKs. EGFR can also be linked to PAK through an adapter protein called NCK which binds PAK to form a tertiary complex of ErbB1-NCK-PAK. Furthermore, PAKs activate Raf by phosphorylating ser338, leading to the activation of ERK/MAPK signaling. Stimulation of EGFR also enhances the level of EGFR-associated PAK1 and GRB2 although the PAK1-GRB2 association is itself independent of this stimulation. ECM components interact with integrins, which via FAK and ETK activate PAK1 which eventually activates the Raf/MEK/ERK kinase cascade. DSCAM, a type I transmembrane protein directly interacts with PAK1 and also stimulates JNK and p38 MAP kinases. Interaction of hPIP1 with PAK1 inhibits the Cdc42/Rac-stimulated kinase activity through the N-terminal regulatory domain of PAK1. PAK2 on the other hand is activated in response to apoptotic stimuli such as ceramide or TNF, and by caspase cleavage followed by autophosphorylation.

Once activated, PAKs can influence actin organization and cell polarity through phosphorylation of substrates such as myosin and MLCK. PAKs also activate MAPK cascades in vertebrates and yeast, as well as the JNK and NF-κB pathways. Activation of JNK causes phosphorylation and activation of several transcription factors. Recently, a family of PIXs were identified as binding tightly to the fourth proline-rich domain in the N-terminus of PAK. PIX can regulate PAK activity both by catalyzing GTP exchange on Cdc42/Rac and by direct binding to PAK. Paxillin, a focal adhesion adaptor protein, acts as a mediator of p21 GTPase-regulated actin cytoskeletal reorganization through the recruitment to nascent focal adhesion structures of an active PAK/PIX complex, potentially via interactions with p95PKL. In contrast to the activation of PAK2 by Rac and Cdc42, cleavage and activation of PAK2 by caspases or caspase-like proteases is involved in the execution of programmed cell death. Proteolytic cleavage generates constitutively active PAK2p34, a 34 kDa C-terminal fragment. Therefore, PAK2 appears to be unique among the PAK isoforms because it can stimulate cell survival or induce cell death depending on the mechanism of activation. Stimulation of cell growth and cell survival by activated PAK appears to be involved in the development of human cancer.

Phospholipase C Signaling

The phospholipase c (PLC) family is divided into six classes: PLC-β, PLC-γ, PLC-δ, PLC-ε, PLC-ζ and PLC-η. PLC-β is activated by the G-αQ or G-β γ subunits released from heterotrimeric G-proteins after ligand stimulation. They are also activated by Rac. PLC-γ, on the other hand, is activated by receptor or non-receptor tyrosine kinases. Polypeptide growth factors activate PLC-γ1 in a wide variety of cells. PLC-γ is also activated by BCR, TCR, the high affinity IgE receptor and the IgG receptors.

Ligation of TCR triggers the activation of Lck and Fyn followed by ZAP70. These proteins, then phosphorylate various downstream substrates including membrane bound LAT and ITK bound SLP76, eventually activating PLC-γ1. BCR engagement triggers the activation of Lyn followed by SYK which phosphorylates BLNK thereby inducing its translocation to the cell membrane. BLNK contributes to activation of BTK and PLC-γ. SYK also directly activates PLC-γ. Ligation of Fc receptors to soluble Ig and immune complexes also contributes to PLC-γ activation.

Src is responsible for the activation of PLC-γ in vascular smooth muscle cells and platelets. Phosphatidic acid is an immediate product of phosphatidylcholine hydrolysis by PLD, activation of which results in the activation of PLC-γ. Arachidonic acid stimulates PLC-γ activity independent of tyrosine phosphorylation in the presence of Tau. Activation PLC-γ is also activated by integrins via Src.

PLC-δ activation involves increases in intracellular Ca2+ concentrations. Ral, a small GTPase, promotes PLC-δ activity. Calmodulin binds and inhibits PLC-δ activity and Ral can reverse this inhibition. PLC-ε is an effector of Ras and Rap. These activated GTPases directly stimulate PLC-ε. The phospholipase activity of PLC-ε is also enhanced through direct interaction with GTP-RhoA. PLC-η has an important role postnatally in the brain. In neurons, PLC-η functions as a Ca2+ sensor that is activated by small increases in intracellular Ca2+ concentrations under physiological conditions.

Activation of PLC results in the hydrolysis of PIP2 to release the second messengers DAG and IP3. DAG is the physiological activator of PKC and IP3 stimulates release of stored Ca2+ from the ER. Ca2+ release activates Calm which further activates Calcineurin, CamKKs and CamKs. Calneurin facilitates NFAT translocation to the nucleus, a process that is essential for axonal growth.

PKC phosphorylates CPI17. Phosphorylation of CPI17 enhances its ability to bind to the catalytic subunit of MLCP causing inhibition of MLCP activity and MLC phosphorylation that leads to actomyosin assembly contraction. PKC phosphorylates transcription factors such as NF-κB, regulating the transcription of certain genes thus controlling cell proliferation or apoptosis. PKC also phosphorylates MARCKS in response to integrin signaling, which is involved in the reorganization of the actin cytoskeleton. PKCs also activate the ERK cascade, including direct phosphorylation of Raf1.

PI3K Signaling in B Lymphocytes

Phosphoinositide-3-Kinases (PI3K) regulate numerous biological processes including cell growth, differentiation, survival, proliferation, migration and metabolism. In the immune system, impaired PI3K signaling leads to immunodeficiency whereas unrestrained signaling contributes to autoimmunity and leukemia. The Class I and III PI3Ks facilitate B cell development through defined stages, resulting in at least three distinct lineages of mature B lymphocytes. In B cells, PI3K is activated within seconds of antigen-receptor triggering. Engagement of BCR-antigen complex activates intracellular protein tyrosine kinases such as SYK, BTK and Fyn which phosphorylate the co-receptors CD19 and BCAP at the YXXM motifs. This provides binding sites for PI3Ks. CD19 is one of the main regulators of PI3K activity in B cells. CD19 has an important, but not indispensable, role in PI3K activation as it is required for sustained PI3K activation after BCR stimulation. The co-receptor complex is also composed of CD21 and CD81. CD21 binds opsonized antigenic particles and activates complement component C3, a reaction central to complement function in the immune response and sustained BCR signaling.

For B cell development, the ability of CD19 to promote a thymus-dependent immune response is linked to its capacity to recruit and activate PI3K. CD19 phosphorylation activates Lyn which in turn recruits PI3K regulatory subunit (p85). Other molecules such as Vav contribute to PI3K activation in B cells by a mechanism that involves the activation of Rac1 which then binds to p85 through its RhoGAP domain. B-cell proliferation is also stimulated by IL-4 via IRS activation, LPS stimulated TLR4 activation and CD40 activated Cbl that engages p85α-associated p110Δ, thus enhancing PI3K signaling. Subsequently, PIP3 is produced at the inner leaflet of the plasma membrane which activates the Akt/PDK-1 Signaling pathway leading to the down regulation of transcription factors such as FoxO3A, thereby facilitating cell survival. Inhibitors such as PTEN and SHIP abrogate PI3K/PIP3 signaling. The PI3K signal is taken over by TAPP adaptor proteins, which have binding specificity for PIP2 and influence the process of cytoskeletal reorganization.

Generation of PIP3 and PIP2 also activates DAPP1, an adaptor protein with a high affinity PIP3-binding PH domain, which generates BCR-dependent calcium flux via IP3R release of stored calcium. One of the targets regulated by calcium elevation is the transcription factor NFAT, whose nuclear translocation is facilitated through its dephosphorylation by calcineurin. PKC-β which is activated by DAG and calcium ions phosphorylates IKK, eventually resulting in the translocation of NF-κB to the nucleus. PKC also activates BIMP1/Bcl10/MALT1 that forms a strong and specific complex within the cell to synergize with the activation of NF-κB. PI3K activates the MAPK cascade via the aPKC/Raf1/MEK route where ERK regulates cell proliferation through induction of transcription factors Elk1, ATF and CREB. Thus PI3K affects the concerted regulation of several transcription factors which mediate gene transcription in B cells.

PI3K/AKT Signaling

Phosphoinositide-3-Kinases (PI3K) regulate numerous biological processes including cell growth, differentiation, survival, proliferation, migration and metabolism. In the immune system, impaired PI3K signaling leads to immunodeficiency whereas unrestrained signaling contributes to autoimmunity and leukemia. The Class I and III PI3Ks facilitate B cell development through defined stages, resulting in at least three distinct lineages of mature B lymphocytes. In B cells, PI3K is activated within seconds of antigen-receptor triggering. Engagement of BCR-antigen complex activates intracellular protein tyrosine kinases such as SYK, BTK and Fyn which phosphorylate the co-receptors CD19 and BCAP at the YXXM motifs. This provides binding sites for PI3Ks. CD19 is one of the main regulators of PI3K activity in B cells. CD19 has an important, but not indispensable, role in PI3K activation as it is required for sustained PI3K activation after BCR stimulation. The co-receptor complex is also composed of CD21 and CD81. CD21 binds opsonized antigenic particles and activates complement component C3, a reaction central to complement function in the immune response and sustained BCR signaling.

For B cell development, the ability of CD19 to promote a thymus-dependent immune response is linked to its capacity to recruit and activate PI3K. CD19 phosphorylation activates Lyn which in turn recruits PI3K regulatory subunit (p85). Other molecules such as Vav contribute to PI3K activation in B cells by a mechanism that involves the activation of Rac1 which then binds to p85 through its RhoGAP domain. B-cell proliferation is also stimulated by IL-4 via IRS activation, LPS stimulated TLR4 activation and CD40 activated Cbl that engages p85α-associated p110Δ, thus enhancing PI3K signaling. Subsequently, PIP3 is produced at the inner leaflet of the plasma membrane which activates the Akt/PDK-1 Signaling pathway leading to the down regulation of transcription factors such as FoxO3A, thereby facilitating cell survival. Inhibitors such as PTEN and SHIP abrogate PI3K/PIP3 signaling. The PI3K signal is taken over by TAPP adaptor proteins, which have binding specificity for PIP2 and influence the process of cytoskeletal reorganization.

Generation of PIP3 and PIP2 also activates DAPP1, an adaptor protein with a high affinity PIP3-binding PH domain, which generates BCR-dependent calcium flux via IP3R release of stored calcium. One of the targets regulated by calcium elevation is the transcription factor NFAT, whose nuclear translocation is facilitated through its dephosphorylation by calcineurin. PKC-β which is activated by DAG and calcium ions phosphorylates IKK, eventually resulting in the translocation of NF-κB to the nucleus. PKC also activates BIMP1/Bcl10/MALT1 that forms a strong and specific complex within the cell to synergize with the activation of NF-κB. PI3K activates the MAPK cascade via the aPKC/Raf1/MEK route where ERK regulates cell proliferation through induction of transcription factors Elk1, ATF and CREB. Thus PI3K affects the concerted regulation of several transcription factors which mediate gene transcription in B cells.

Production of Nitric Oxide and Reactive Oxygen Species in Macrophages

Production of nitric oxide (NO) by activated macrophages is central to the control of infections. The inducible form of nitric oxide synthase (iNOS) is responsible for NO production in macrophages. Regulation of iNOS takes place at the level of transcription, with factors such as cytokines and bacterial products playing a prominent role.

Among the cytokines, IFNγ is a major inducer of iNOS. IFNγ induces the transcription of iNOS by activating interferon regulated factor-1 (IRF-1) as well as the JAK/STAT pathway. In addition to the transcriptional activation of iNOS, IFNγ also induces the transcription of TNF. The endogenously produced TNF activates NF-κB, which in turn triggers the transcription of iNOS. Thus TNF and IFNγ demonstrate transcriptional synergy toward the expression of iNOS. Several bacterial products trigger toll like receptor (TLR) signaling via ERK/MAPK and PI3K signaling cascades. The triggering of the latter pathways culminates in the activation of transcription factors such as NF-κB, CREB binding protein (CBP) and AP-1 complex, which in turn results in the transcription of the iNOS gene.

In addition to NO, the microbicidal and tumoricidal properties of macrophages are dependent on the production of reactive oxygen species (ROS). The respiratory burst, which is the production of ROS, is largely attributed to the activation of the nicotinamide adenine dinucleotide phosphate oxidase (NADPH oxidase). The latter enzyme complex is part of the electron transport chain, whose major membrane-bound components are gp-91 phox and p22 phox. The cytosolic components of NADPH oxidase include p47 phox and p67 phox. Factors such as bacterial products, hormones and chemicals can activate NADPH oxidase by enhancing the membrane translocation of its cytosolic subunits. In addition, several factors such as TNF, IFNγ and PPARα can enhance the expression of NADPH oxidase subunits, which in turn could lead to the activation of the enzyme.

This pathway highlights the important molecular events that lead to NO and ROS production in macrophages.

Protein Kinase A Signaling

Protein kinase A (PKA) regulates processes as diverse as growth, development, memory, and metabolism. It exists as a tetrameric complex of two catalytic subunits (PKA-C) and a regulatory (PKA-R) subunit dimer. Type-II PKA is anchored to specific locations within the cell by AKAPs. Extracellular stimuli such as neurotransmitters, hormones, inflammatory stimuli, stress, epinephrine and norepinephrine activate G-proteins through receptors such as GPCRs and ADR-α/β. These receptors along with others such as CRHR, GcgR and DCC are responsible for cAMP accumulation which leads to activation of PKA. The conversion of ATP to cAMP is mediated by the 9 transmembrane AC enzymes and one soluble AC. The transmembrane AC are regulated by heterotrimeric G-proteins, Gαs, Gαq and Gαi. Gαs and Gαq activate while Gαi inhibits AC. Gβ and Gγ subunits act synergistically with Gαs and Gαq to activate ACII, IV and VII. However the β and γ subunits along with Gαi inhibit the activity of ACI, V and VI.

G-proteins indirectly influence cAMP signaling by activating PLC, which generates DAG and IP3. DAG in turn activates PKC. IP3 modulates proteins upstream to cAMP signaling with the release of Ca2+ from the ER through IP3R. Ca2+ is also released by CaCn and CNG. Ca2+ release activates Calmodulin, CamKKs and CamKs, which take part in cAMP modulation by activating ACI. Gα13 activates MEKK1 and RhoA via two independent pathways which induce phosphorylation and degradation of IkBα and activation of PKA. High levels of cAMP under stress conditions like hypoxia, ischemia and heat shock also directly activate PKA. TGF-β activates PKA independent of cAMP through phosphorylation of SMAD proteins.

PKA phosphorylates Phospholamban which regulates the activity of SERCA2 leading to myocardial contraction, whereas phosphorylation of TnnI mediates relaxation. PKA also activates KDELR to promote protein retrieval thereby maintaining steady state of the cell. Increase in concentration of Ca2+ followed by PKA activation enhances eNOS activity which is essential for cardiovascular homeostasis. Activated PKA represses ERK activation by inhibition of Raf1. PKA inhibits the interaction of 14-3-3 proteins with BAD and NFAT to promote cell survival.

PKA phosphorylates endothelial MLCK leading to decreased basal MLC phosphorylation. It also phosphorylates filamin, adducin, paxillin and FAK and is involved in the disappearance of stress fibers and F-actin accumulation in membrane ruffles. PKA also controls phosphatase activity by phosphorylation of a specific PPtaseI inhibitor, DARPP32. Other substrates of PKA include histone H1, histone H2B and CREB.

PKA phosphorylates and inactivates GSK3, thus preventing oncogenesis and neurodegeneration. It also inactivates GYS, which prevents the futile cycling of glucose-1 phosphate back into glycogen via UDP-glucose. HSL, an important enzyme of lipolysis, is also phosphorylated by PKA. PKA phosphorylates GRK1 and GRK7 which reduces the phosphorylation of Rhodopsin. PKA also phosphorylates β-catenin and inhibits its ubiquitination in intact cells. Phosphorylation of p75(NTR) by PKA facilitates the efficiency of its signal transduction. PKA also regulates Gli3 under the influence of hedgehog signaling. Failure to regulate PKA may have disastrous consequences including diseases such as cancer.

Rac Signaling

To achieve strong adhesion to their neighbors and sustain stress and tension, epithelial cells develop many different specialized adhesive structures. Breakdown of these structures occurs during tumor progression with the development of a fibroblastic morphology characteristic of metastatic cells. Adhesion receptors of the cadherin family have been implicated in development and maintenance of the differentiated epithelial phenotype. Cadherin mediated cell adhesion requires the activity of the cytosolic proteins of the Rho subfamily Rho, Rac and Cdc42.

Rac is a small GTPase that is activated by GEF, in particular ARHGEF6. Rac mediates key cellular processes in response to upstream regulators such as growth factors, integrins and hyaluronic acid binding receptor CD44. Rac is a key downstream target of PI3K. Rac is also activated by integrin via FAK. Interaction between CD44 and TIAM1 can also activate Rac. TIAM1 is a known GDP/GTP exchange factor for Rac. TIAM1 and the cytoskeletal protein Ankyrin physically associate as a complex. Ankyrin binding to TIAM1 activates Rac. Upon activation, Rac interacts with and regulates a spectrum of functionally diverse downstream effectors, initiating a network of cytoplasmic and nuclear signaling cascades.

A number of proteins act as targets for Rac including PAKs, IQGAP1, CDC42, POR1 and POSH. Rac binds p67(Phox) to increase activation of the NADPH oxidase system and production of reactive oxygen species (ROS), which mediates activation of NF-κB-dependent gene expression. Rac binds the WAVE complex to release active WAVE which promotes actin polymerization in lamellipodia through activation of the ARP2/3 complex. Rac also binds to the actin binding protein IQGAP which is implicated in regulation of cell-cell adhesion and microtubule orientation. Recently, a novel Rac interacting protein, POR1, has been identified that plays a role in membrane ruffling. p140SRA1 is another novel target for Rac that is involved in membrane ruffling.

Rac is also implicated in the regulation of PLD which is critical in cell growth. Rac binds to and activates PIP5K, which increases the amount of PIP2. Rac coordinately activates p70S6K and JNK via MLK3 activation. Once activated, JNK enters the nucleus and phosphorylates transcription factors such as c-Jun, c-Fos, Elk1 and Elk4. Rac also activates DBS, which further activates RhoA and Cdc42. In neurons, Rac acts through CDK5 and p35 to phosphorylate and downregulate PAK1, increasing neuronal migration. PAK1 also phosphorylates and activates LIMK, which phosphorylates and inhibits cofilin. Cofilin stimulates actin depolymerization and changes in cell structure.

Rac controls the generation of ROS, both in leukocytes and non-hematopoietic cells, and is necessary for cadherin-dependent adhesion. Rac activation is required for the fully transformed phenotype induced by oncogenes such as TIAM1 and Ras. In addition, Rac activation perturbs cadherin contacts with a concomitant change in cell shape including formation of lamellae and conversion to a fibroblastic morphology.

RANK Signaling in Osteoclasts

To achieve strong adhesion to their neighbors and sustain stress and tension, epithelial cells develop many different specialized adhesive structures. Breakdown of these structures occurs during tumor progression with the development of a fibroblastic morphology characteristic of metastatic cells. Adhesion receptors of the cadherin family have been implicated in development and maintenance of the differentiated epithelial phenotype. Cadherin mediated cell adhesion requires the activity of the cytosolic proteins of the Rho subfamily Rho, Rac and Cdc42.

Rac is a small GTPase that is activated by GEF, in particular ARHGEF6. Rac mediates key cellular processes in response to upstream regulators such as growth factors, integrins and hyaluronic acid binding receptor CD44. Rac is a key downstream target of PI3K. Rac is also activated by integrin via FAK. Interaction between CD44 and TIAM1 can also activate Rac. TIAM1 is a known GDP/GTP exchange factor for Rac. TIAM1 and the cytoskeletal protein Ankyrin physically associate as a complex. Ankyrin binding to TIAM1 activates Rac. Upon activation, Rac interacts with and regulates a spectrum of functionally diverse downstream effectors, initiating a network of cytoplasmic and nuclear signaling cascades.

A number of proteins act as targets for Rac including PAKs, IQGAP1, CDC42, POR1 and POSH. Rac binds p67(Phox) to increase activation of the NADPH oxidase system and production of reactive oxygen species (ROS), which mediates activation of NF-κB-dependent gene expression. Rac binds the WAVE complex to release active WAVE which promotes actin polymerization in lamellipodia through activation of the ARP2/3 complex. Rac also binds to the actin binding protein IQGAP which is implicated in regulation of cell-cell adhesion and microtubule orientation. Recently, a novel Rac interacting protein, POR1, has been identified that plays a role in membrane ruffling. p140SRA1 is another novel target for Rac that is involved in membrane ruffling.

Rac is also implicated in the regulation of PLD which is critical in cell growth. Rac binds to and activates PIP5K, which increases the amount of PIP2. Rac coordinately activates p70S6K and JNK via MLK3 activation. Once activated, JNK enters the nucleus and phosphorylates transcription factors such as c-Jun, c-Fos, Elk1 and Elk4. Rac also activates DBS, which further activates RhoA and Cdc42. In neurons, Rac acts through CDK5 and p35 to phosphorylate and downregulate PAK1, increasing neuronal migration. PAK1 also phosphorylates and activates LIMK, which phosphorylates and inhibits cofilin. Cofilin stimulates actin depolymerization and changes in cell structure.

Rac controls the generation of ROS, both in leukocytes and non-hematopoietic cells, and is necessary for cadherin-dependent adhesion. Rac activation is required for the fully transformed phenotype induced by oncogenes such as TIAM1 and Ras. In addition, Rac activation perturbs cadherin contacts with a concomitant change in cell shape including formation of lamellae and conversion to a fibroblastic morphology.

Regulation of Actin-Based Motility By Rho

The actin filament network immediately under the plasma membrane in regions of rapid cellular protrusion consists of short, branched filaments while those deeper in the cortex, as well as at focal adhesions, stress fibers and in microvilli, are much longer and rarely branched. The dynamic organization of the actin cytoskeleton provides the force for cell motility and is regulated by small GTPases of the Rho family, in particular Rac1, RhoA and CDC42. The microtubule cytoskeleton is also polarized in a migrating cell, and in addition to organizing the actin cytoskeleton; Rho GTPases also influence the organization and dynamics of these microtubules.

Rho family proteins regulate a broad diversity of cellular functions including cytoskeletal organization, membrane trafficking, cytokinesis, cell proliferation, cell motility and transcriptional regulation. These G-Proteins function as molecular switches in signal transduction pathways by cycling between an active GTP-bound and an inactive GDP-bound state. GEFs (Guanine Nucleotide Exchange Factors) catalyze the exchange bound GDP for GTP, whereas GAPs (GTP Activating Proteins) increase their intrinsic GTPase activity and GDIs (GDP Dissociation Inhibitors) prevent release of bound GDP. In fibroblasts, these proteins regulate various cytoskeletal rearrangements: RhoA controls stress fiber formation and the attachment of contractile bundles of actin and myosin filaments to the cell membrane at points of focal adhesion, where integrin clusters are present. Rac regulates the polymerization to drive lamellipodial protrusion and the formation of membrane ruffles, whereas CDC42 generates polarity and induces formation of filopodia and microspikes. These GTPases function sequentially: CDC42 stimulates Rac activity, which then activates Rho. Activated CDC42, Rac and Rho bind to and specifically activate their downstream effectors, which are either kinases such as ROCK, PAK and PI5K or scaffolding proteins such as GDIA, WASP and IRSp53. GDIA mediates force-induced contact formation, even if the entire ROCK-activated pathway, including Myosin-II activation, is eliminated. Constitutively active GDIA lacking Rho-binding domains cooperate with activated ROCK to form stress fibers. PAK activates LIM-kinases (LIMK1 and LIMK2) to phosphorylate ADF/cofilins. This allows signals flowing through Rho family GTPases to coordinate the initiation of new filaments through WASP and ARP2/3 complex. Both LIMK1 and LIMK2 are downstream effectors of the Rho GTPases. GTP-bound Rho also activates an enzyme known as Rho-kinase, which phosphorylates the myosin-binding subunit of MLCP, inactivating it and thereby preventing MLC dephosphorylation. As a result, Rho activation leads to an accumulation of the phosphorylated MLC and, subsequently, to the stimulation of actomyosin ATPase activity. Activation by WAVE1, another member of the WASP family, also induces actin alterations in response to Rac1 signals upstream. Activated Rac, which is known to bind and activate PI5K, stimulate biosynthesis of PIP2, leading to promotion of actin assembly from profilin and gelsolin.

The Rho family of GTPases comprises some 21 genes in humans, encoding at least 23 signaling proteins. Although these proteins control an amazingly diverse range of cellular functions, one general role is in the establishment of polarity and of polarized structures through dynamic regulation of the actin cytoskeleton. Rho GTPases control the polymerization, branching and bundling of actin, allowing them to regulate the remodeling of the actin cytoskeleton into distinct architectural elements.

RhoA Signaling

RhoA is a member of the Ras superfamily of small GTPases that plays a central role in diverse biological processes such as actin cytoskeleton organization, microtubule dynamics, gene transcription, oncogenic transformation, cell cycle progression, adhesion and epithelial wound repair. The activation state of RhoA is controlled by regulatory proteins such as GEFs which catalyze the exchange of GDP for GTP thereby activating Rho, GDIs which inhibit the release of GDP to keep Rho inactive, and GAPs which increase the rate at which Rho hydrolyzes GTP and becomes inactivated.

RhoA is activated by a variety of growth factors, cytokines, adhesion molecules, hormones, integrins, G-proteins and other biologically active substances. The major activator of RhoA are GPCRs which use G$\alpha$11, G$\alpha$12 or G$\alpha$i for signal transduction. These GPCRs include receptors for LPA and certain hormones. EphA receptors also directly activate RhoA through Ephexin. IGF activates RhoA indirectly by binding IGF1 R which forms a complex with LARG.

A number of proteins have been identified as targets of RhoA, which include the PAK family kinases, ROCK family kinases, MBS of myosin PPtase, PKN/PRK-1, Rhophilin, Rhotekin, Citron, and GDIA. RhoA is important for the organization of stress fibers and also in the regulation of actinomyosin contractility through myosin PPtase and MLCP phosphorylation through ROCK. ROCK family kinases also activate LIMK which phosphorylates and inactivates cofilin and regulates actin cytoskeletal reorganization. ROCKs phosphorylate Ezrin/Villin, Radixin and Moesin (ERM) proteins in vitro. ROCKs can also phosphorylate the sodium-hydrogen exchanger, NHE1, which interacts with ERM proteins both directly and via EBP50. Both Rac and RhoA bind to and activate PIP5K which increases the amount of PIP2 and activation of ERM proteins.

Besides ROCK, other important targets of RhoA include FAK, PRK-1/PKN1, BORG, Citron, PLD and GDIA. The GTPase RhoA plays a prominent role in regulating the organization of the cytoskeleton by promoting the assembly of focal adhesions, actin stress fibers and activating FAK. PKN1/PRK-1 and PKN2 are Rho targets involved in endosomal trafficking. Citron is a ROCK related kinase that is critical for cytokinesis and is also implicated in other aspects of cell cycle progression. BORG proteins are Rho targets that connect to septins which polymerize to form filaments involved in cytokinesis in yeast and mammalian cells. RhoA and Rac are also implicated in the regulation of PLD. PLD catalyzes the hydrolysis of phosphatidylcholine to yield phosphatidic acid and choline. Phosphatidic acid is a second messenger involved in membrane remodeling events that are critical to cell growth, such as vesicle trafficking and regulated secretion. RhoA also activates scaffolding proteins such as GDIA, WASP and IRSp53. RhoA binds to Rhophilin and regulates the actin cytoskeleton. RhoA also interacts with a Rho target protein, Rhotekin through the RBD motif. RhoA-dependent signaling is recognized as an essential regulator of vascular function and seems to play an important role in major arterial diseases such as hypertension, atherosclerosis and pulmonary hypertension.

Role of NFAT in Cardiac Hypertrophy

RhoA is a member of the Ras superfamily of small GTPases that plays a central role in diverse biological processes such as actin cytoskeleton organization, microtubule dynamics, gene transcription, oncogenic transformation, cell cycle progression, adhesion and epithelial wound repair. The activation state of RhoA is controlled by regulatory proteins such as GEFs which catalyze the exchange of GDP for GTP thereby activating Rho, GDIs which inhibit the release of GDP to keep Rho inactive, and GAPs which increase the rate at which Rho hydrolyzes GTP and becomes inactivated.

RhoA is activated by a variety of growth factors, cytokines, adhesion molecules, hormones, integrins, G-proteins and other biologically active substances. The major activator of RhoA are GPCRs which use G$\alpha$11, G$\alpha$12 or G$\alpha$i for signal transduction. These GPCRs include receptors for LPA and certain hormones. EphA receptors also directly activate RhoA through Ephexin. IGF activates RhoA indirectly by binding IGF1 R which forms a complex with LARG.

A number of proteins have been identified as targets of RhoA, which include the PAK family kinases, ROCK family kinases, MBS of myosin PPtase, PKN/PRK-1, Rhophilin, Rhotekin, Citron, and GDIA. RhoA is important for the organization of stress fibers and also in the regulation of actinomyosin contractility through myosin PPtase and MLCP phosphorylation through ROCK. ROCK family kinases also activate LIMK which phosphorylates and inactivates cofilin and regulates actin cytoskeletal reorganization. ROCKs phosphorylate Ezrin/Villin, Radixin and Moesin (ERM) proteins in vitro. ROCKs can also phosphorylate the sodium-hydrogen exchanger, NHE1, which interacts with ERM proteins both directly and via EBP50. Both Rac and RhoA bind to and activate PIP5K which increases the amount of PIP2 and activation of ERM proteins.

Besides ROCK, other important targets of RhoA include FAK, PRK-1/PKN1, BORG, Citron, PLD and GDIA. The GTPase RhoA plays a prominent role in regulating the organization of the cytoskeleton by promoting the assembly of focal adhesions, actin stress fibers and activating FAK. PKN1/PRK-1 and PKN2 are Rho targets involved in endosomal trafficking. Citron is a ROCK related kinase that is critical for cytokinesis and is also implicated in other aspects of cell cycle progression. BORG proteins are Rho targets that connect to septins which polymerize to form filaments involved in cytokinesis in yeast and mammalian cells. RhoA and Rac are also implicated in the regulation of PLD. PLD catalyzes the hydrolysis of phosphatidylcholine to yield phosphatidic acid and choline. Phosphatidic acid is a second messenger involved in membrane remodeling events that are critical to cell growth, such as vesicle trafficking and regulated secretion. RhoA also activates scaffolding proteins such as GDIA, WASP and IRSp53. RhoA binds to Rhophilin and regulates the actin cytoskeleton. RhoA also interacts with a Rho target protein, Rhotekin through the RBD motif. RhoA-dependent signaling is recognized as an essential regulator of vascular function and seems to play an important role in major arterial diseases such as hypertension, atherosclerosis and pulmonary hypertension.

Role of NFAT in Regulation of the Immune Response

NFATs are a family of transcription factors expressed in a variety of cell types of the immune system, and play a pivotal role in the process. NFATs are basically Calcium-dependent transcription factors, activated by stimulation of receptors coupled to Calcium-Calcineurin signals. Balanced activation of NFAT and Fos-Jun complex is known to be required for productive immune responses. Concomitant induction of NFAT and Fos-Jun requires concerted activation of two different signaling pathways: Calcium-Calcineurin, which promotes NFAT dephosphorylation, nuclear translocation and activation; and MAPK pathway which promotes the synthesis, phosphorylation and activation of members of the Fos and Jun families of transcription factors, downstream of MAPK pathway.

Activation of antigen receptors of the immune cells and the subsequent stimulation of costimulatory receptors in response to antigen presentation leads to activation of a series of signal transduction events mediated by several cytosolic tyrosine kinases and adaptor proteins like LAT, SLP76, and GRB2, SLP65 etc. and various kinases like ITK, BTK and SYK. These receptors contain unique cytoplasmic domains essential for downstream signaling, called ITAMs. One critical protein that is recruited to the adaptor proteins upon immunoreceptor stimulation is PLC-γ whereas, PLC-β is activated by the GPCRs. PLC is responsible for the production of the second messengers DAG and IP3. This event triggers the opening of CRAC channels at the plasma membrane, allowing influx of extracellular Ca2+, activating Calcineurin. This leads to the dephosphorylation of NFAT, allowing it to enter the nucleus for the induction of NFAT-mediated gene transcription. Effective phosphate removal by NFATs remain in the nucleus while Ca2+ is in elevated concentration and are rapidly phosphorylated and exported to the cytoplasm upon termination of Calcium signaling. Nuclear import of dephosphorylated NFATs is facilitated by Importins. In stimulated cells, an increase of intracellular Calcium ions activates Ccalcineurin to bring about dephosphorylation of NFAT. On the other hand, several kinases phosphorylate NFAT proteins and control their nuclear shuttling, including GSK3, CK1, p38 and JNK. CK1 docks at a conserved motif that is near the N-terminus of NFAT proteins, and it functions as both maintenance and an export kinase for SRR1. GSK3 functions as an export kinase. In stimulated active cells, it is inhibited by the PI3K/Akt pathway activated by CD28 costimulation. MAPKs differentially phosphorylate the first serine of SRR1 in the different NFAT proteins: p38 phosphorylates NFAT1, whereas JNK phosphorylates NFAT2. Rephosphorylation of NFAT by protein kinases brings about exposure of its NES and can be exported to the cytoplasm by the exportin CRM1.

The novel PKC isoform, PKC-θ is selectively expressed by the integration of TCR and CD28 costimulatory signals. Productive engagement of T-Cells by Antigen Presenting Cells results in recruitment of PKC-θ to the T-Cell-Antigen-Presenting Cell contact area-the Immunological Synapse, where it interacts with several signaling molecules like Fyn, Lck and ZAP70 to induce activation signals essential for the activation of transcription factors NF-κB, c-Jun and c-Fos. PKC-θ also cooperates with Calcineurin, in transducing signals leading to activation of c-Fos, c-Jun and NFAT.

NFAT1 induces T-Cell anergy if prevented from interacting with its transcriptional partners: c-Fos and c-Jun. Thus, a single transcription factor, NFAT, regulates two contrasting aspects of T-Cell function, mediating non-overlapping genetic programs of productive activation or anergy depending on the availability of Ca2+ and the presence or absence of its transcriptional partners.

Signaling By Rho Family GTPases

The GTPase family of small GTP-binding proteins comprises a group of signaling molecules that are activated by growth factors, cytokines, adhesion molecules, hormones and integrins. They regulate a wide range of biological processes, including reorganization of the actin cytoskeleton, transcriptional regulation, vesicle trafficking, morphogenesis, neutrophil activation, phagocytosis, mitogenesis, apoptosis and tumorigenesis. The mammalian GTPase family currently consists of three subfamilies: Rho, Rac and Cdc42. Each controls the formation of a distinct cytoskeletal element in mammalian cells. Activation of Rac induces actin polymerization to form lamellipodia, whereas activation of Cdc42 stimulates the polymerization of actin to filopodia or microspikes. In contrast, Rho regulates bundling of actin filaments into stress fibers and the formation of focal adhesion complexes. The small GTPases act as molecular switches, cycling between an active GTP-bound state and an inactive GDP-bound state, a process that is regulated by Guanine nucleotide exchange factors (GEF) and GTPase activating proteins (GAP).

A number of proteins have been identified as targets of Rho with ROCK being a prominent target. ROCK phosphorylates MLC which plays an important role in actomyosin contractility. ROCK also activates LIMK, which results in Cofilin inactivation and leads to actin polymerization. Both Rac and Rho bind to and activate PIP5K which then activates ERM proteins. ROCK also phosphorylates intermediate filaments such as vimentin and desmin. These effects of ROCK have been linked to reorganization of intermediate filaments at cytokinesis.

Similar to Rho, Rac and Cdc42 also affect numerous downstream molecules that mediate effects on the cytoskeleton and gene expression. Rac releases active WAVE, which promotes actin polymerization in lamellipodia through activation of the ARP2/3 complex. Rac and Cdc42 bind and activate PAK family members. PAKs have multiple substrates, including LIMK and OP18/Stathmin. Rac and Cdc42 also bind to the actin-binding protein IQGAP, which is implicated in regulation of cell-cell adhesion and microtubule orientation. Rac and Cdc42 also bind to PI3K, thus activating the PI3K/AKT signaling pathway.

Signaling pathways that are regulated by GTPase family members play an important role in several pathological conditions, including cancer, inflammation, and bacterial infections. Although substantial evidence indicates that the balance between the two nucleotide-bound states of these proteins correlates well with their ability to promote biological responses, the precise mechanism by which this balance is regulated is still largely unknown. Moreover, although it is clear that a discrete 'on-off' switch is too simple a mechanism to account for the current experimental evidence, whether the regulated intracellular translocation of GTPases plays a role still needs to be elucidated.

Synaptic Long Term Potentiation

Long-term potentiation (LTP) is the increase of synaptic strength between two neurons following high frequency stimulation to the synapse. A majority of synapses that experience LTP (e.g. in the hippocampus) involve a postsynaptic increase in calcium which is mediated through activation of the ionotropic glutamate receptor N-methyl-D-aspartic acid (NMDA) receptor. Activation of NMDA receptors by glutamate released from the presynaptic neuron results in Ca2+ influx which coactivates the extracellular regulated signal kinase (ERK) and cyclic adenosine monophosphate (cAMP) signal transduction pathways. Activation of these two regulatory pathways increases the transcription of a family of genes via the cAMP responsive element binding (CREB) protein activation. CREB mediated transcriptional activation in the post synaptic neuron is believed to be an important event in LTP.

The NMDA receptor mediated Ca2+ flux activates Calmodulin dependent adenylyl cyclases which play a critical role in generating the cAMP, which in turn activates protein kinase A (PKA). The activation of PKA plays a major role in supporting the nuclear translocation of ERK. ERK activation leads to indirect activation of CREB by coupling to ribosomal protein S6 kinase (RSK), which then phosphorylates and activates CREB. The activation of PKA also results in the activation of I-1, an inhibitor of protein phosphatase 1 (PP1). In the absence of activated I-1, calmodulin kinase II (CaMKII) is dephosphorylated and inactivated by PP1. The NMDA receptor dependent PKA mediated phosphorylation of I-1 thus results in the activation of CaMKII, one of the most abundant proteins in neurons. Activated CaMKII plays a role in the activation and phosphorylation of the ionotropic glutamate receptor alpha-amino-3-hydroxy-5-methylisoxazole-4-propionic acid (AMPA) receptor. This covalent modification of AMPA receptors results in a modulation of receptor numbers and therefore to an increased response to glutamate—an important postsynaptic event in LTP. The NMDA mediated Ca2+ flux also activates CaMKIV which triggers CREB/CREB binding protein (CBP)-dependent transcription by phosphorylating CBP.

In addition to the ionotropic glutamate receptors, the metabotropic glutamate receptors mGluR also play a role in LTP. The mGluR via coupled G protein activates the phospholipase C (PLC)/protein kinase C (PKC) pathway which triggers the NMDA receptor, thus increasing Ca2+ influx. The inositol triphosphate (IP3) generated as a result of PLC activation increases Ca2+ release from intracellular sources, further activating calmodulin dependent pathways.

This pathway highlights the important components of Long term potentiation signaling.

Telomerase Signaling

The extended growth potential of cancer cells is critically dependent upon the maintenance of functional telomeres, which are sections of DNA occurring at the ends of each chromosome in a eukaryotic cell. Telomeres consist of highly repetitive sequences of DNA that do not code for proteins, but function as caps to keep chromosomes from fusing together. In order to divide, a normal cell has to replicate the entire DNA in its chromosomes. However, the last few bases on the telomere are not copied with each round of DNA replication as a cell ages, which results in telomere shortening with each round of cell division. At one point, cells stop going through cell division, and this halt in growth is triggered by genes that are activated in response to DNA damage such as p53. A telomere that becomes too short no longer protects the chromosome from DNA damage. Cell replication is stopped and the cell is forced into senescence.

Telomeric structural proteins fall into two general groups: those that bind telomeric DNA directly, and those that interact, directly or indirectly, with the telomeric DNA-binding proteins. Some telomeric DNA-binding proteins bind single-stranded telomeric DNA and others bind duplex telomeric DNA. The telomerase ribonucleoprotein enzyme complex binds the protruding single-stranded end of the G-rich telomeric DNA strand in order to extend it and make up for the loss of terminal sequences resulting from normal semi-conservative DNA replication. Telomerase synthesizes its species-specific telomeric repeat sequence by elongating a DNA primer. It has two essential components, the RNA component TERC and a catalytic subunit TERT. TERC acts in concert to elongate telomeres by reading from the RNA template sequence carried by the RNA subunit and synthesizing a complementary DNA strand.

The expression of the TERT catalytic subunit is upregulated by growth factors such as EGF via the Ras-Raf-MEK-ERK pathway, while it is downregulated by inhibiting factors that promote apoptosis or block cell division such as p53, p21CIP1, E2F and HDAC. Post-translational signaling events acting directly on TERT also play a role in regulation of telomerase activity, such as activation of TERT by AKT and HSP90 and inhibition of TERT by c-Abl, where the phosphorylation state of TERT modulates the catalytic activity of telomerase. Additional molecules that regulate the activity of hTERC-hTERT and the maintenance of telomere structure include TRF1,Tankyrase, TIN-2 and RAP1. These proteins interact with the telomere and regulate the opening and closing of the free telomere end and access to the telomere by other protein complexes including the telomerase components.

α-Adrenergic Signaling

The extended growth potential of cancer cells is critically dependent upon the maintenance of functional telomeres, which are sections of DNA occurring at the ends of each chromosome in a eukaryotic cell. Telomeres consist of highly repetitive sequences of DNA that do not code for proteins, but function as caps to keep chromosomes from fusing together. In order to divide, a normal cell has to replicate the entire DNA in its chromosomes. However, the last few bases on the telomere are not copied with each round of DNA replication as a cell ages, which results in telomere shortening with each round of cell division. At one point, cells stop going through cell division, and this halt in growth is triggered by genes that are activated in response to DNA damage such as p53. A telomere that becomes too short no longer protects the chromosome from DNA damage. Cell replication is stopped and the cell is forced into senescence.

Telomeric structural proteins fall into two general groups: those that bind telomeric DNA directly, and those that interact, directly or indirectly, with the telomeric DNA-binding proteins. Some telomeric DNA-binding proteins bind single-stranded telomeric DNA and others bind duplex telomeric DNA. The telomerase ribonucleoprotein enzyme complex binds the protruding single-stranded end of the G-rich telomeric DNA strand in order to extend it and make up for the loss of terminal sequences resulting from normal semi-conservative DNA replication. Telomerase synthesizes its species-specific telomeric repeat sequence by elongating a DNA primer. It has two essential components, the RNA component TERC and a catalytic subunit TERT. TERC acts in concert to elongate telomeres by reading from the RNA template sequence carried by the RNA subunit and synthesizing a complementary DNA strand.

The expression of the TERT catalytic subunit is upregulated by growth factors such as EGF via the Ras-Raf-MEK-ERK pathway, while it is downregulated by inhibiting factors that promote apoptosis or block cell division such as p53, p21CIP1, E2F and HDAC. Post-translational signaling events acting directly on TERT also play a role in regulation of telomerase activity, such as activation of TERT by AKT and HSP90 and inhibition of TERT by c-Abl, where the phosphorylation state of TERT modulates the catalytic activity of telomerase. Additional molecules that regulate the activity of hTERC-hTERT and the maintenance of telomere structure include TRF1,Tankyrase, TIN-2 and RAP1. These proteins interact with the telomere and regulate the opening and closing of the free telomere end and access to the telomere by other protein complexes including the telomerase components.

TABLE 9

Canonical Pathway and Effect of GEO 300 mg and GEO 600 mg

| Canonical Pathway | 300 mg | 600 mg | Action |
|---|---|---|---|
| Actin Cytoskeleton Signaling | 1 | 1 | Up Regulated |
| CD28 Signaling in T Helper Cells |  | 1 | Up Regulated |
| Chemokine Signaling |  | 1.632993162 | Up Regulated |
| CREB Signaling in Neurons | 1 |  | Up Regulated |
| CXCR4 Signaling | 0.846 |  | Up Regulated |
| Ephrin Receptor Signaling | 1.341640786 | 0.816496581 | Up Regulated |
| ERK/MAPK Signaling |  | 0.377964473 | Up Regulated |
| Fcγ Receptor-mediated Phagocytosis in Macrophages and Monocytes |  | 1 | Up Regulated |
| fMLP Signaling in Neutrophils | 2 | 1.632993162 | Up Regulated |
| GNRH Signaling |  | 0.447213595 | Up Regulated |
| GP6 Signaling Pathway | 2 |  | Up Regulated |
| Gα12/13 Signaling |  | 0.447213595 | Up Regulated |
| Gαq Signaling | 1 | 1.632993162 | Up Regulated |
| Gαs Signaling |  | 1 | Up Regulated |
| IL-6 Signaling |  | 1.341640786 | Up Regulated |
| IL-8 Signaling |  | 1.341640786 | Up Regulated |
| Insulin Receptor Signaling |  | 0.447213595 | Up Regulated |
| Integrin Signaling |  | 0.816496581 | Up Regulated |
| Melatonin Signaling |  | 1 | Up Regulated |
| Nitric Oxide Signaling in the Cardiovascular System |  | 1.341640786 | Up Regulated |
| Noradrenaline and Adrenaline Degradation |  | 1 | Up Regulated |
| NRF2-mediated Oxidative Stress Response | 1.633 | 1.633 | Up Regulated |
| Oncostatin M Signaling |  | 1 | Up Regulated |
| Oxidative Phosphorylation | 2 | 2.236067977 | Up Regulated |
| P2Y Purigenic Receptor Signaling Pathway |  | 1 | Up Regulated |
| p70S6K Signaling |  | 1 | Up Regulated |
| PAK Signaling |  | 0.447213595 | Up Regulated |
| Phospholipase C Signaling | 1.341640786 | 2.121320344 | Up Regulated |
| PI3K Signaling in B Lymphocytes |  | 1 | Up Regulated |
| PI3K/AKT Signaling |  | 1 | Up Regulated |
| Production of Nitric Oxide and Reactive Oxygen Species in Macrophages |  | 0.816496581 | Up Regulated |
| Protein Kinase A Signaling | 0.816496581 | 0.707106781 | Up Regulated |
| Rac Signaling |  | 1.341640786 | Up Regulated |
| RANK Signaling in Osteoclasts |  | 1.341640786 | Up Regulated |
| Regulation of Actin-based Motility by Rho |  | 2 | Up Regulated |
| RhoA Signaling |  | 2.236067977 | Up Regulated |
| Signaling by Rho Family GTPases | 1 | 1.889822365 | Up Regulated |
| Synaptic Long Term Potentiation |  | 0.816496581 | Up Regulated |
| Telomerase Signaling |  | 1 | Up Regulated |
| α-Adrenergic Signaling |  | 1 | Up Regulated |

REFERENCES

Forstermann U, Sessa W C. Nitric oxide synthases: regulation and function. European Heart Journal. 2012; 33(7): 829-837. doi:10.1093/eurheari/ehr304.

Stamler J S, Meissner G. Physiology of Nitric Oxide in Skeletal Muscle. Physiol. Rev. 2001; 81(1):209-237. doi: 10.1152/physrev.2001.81.1.209.

F. Suhr, S. Gehlert, M. Grau, W. Bloch, Skeletal muscle function during exercise-fine tuning of diverse subsystems by nitric oxide, Int J Mol Sci. 14 (2013) 7109-7139.

S. Moncada, E. A. Higgs, Endogenous nitric oxide: physiology, pathology and clinical relevance, Eur J Cin Invest. 21 (1991) 361-374.

Tengan C H, Rodrigues G S, Godinho R O. Nitric Oxide in Skeletal Muscle: Role on Mitochondrial Biogenesis and Function. International Journal of Molecular Sciences. 2012; 13(12):17160-17184. doi:10.3390/ijms131217160.

Marechal G, Gailly P. Effects of nitric oxide on the contraction of skeletal muscle. Cell Mol Life Sci. 1999; 55(8-9):1088-1102.

Besco R, Sureda A Tur J A, Pons A. The Effects of Nitric-Oxide-Related Supplements on Human Performance. Sport Med. 2012; 42(2):99-117. doi:10.2165/11596860-000000000-00000.

Parthasarathy S, Raghavamenon A, Garelnabi M O, Santanam N. Oxidized Low-Density Lipoprotein. Methods in Molecular Biology (Clifton, N.J.). 2010; 610:403-417. doi:10.1007/978-1-60327-029-8_24.

Steinberg, D. (1997). Low Density Lipoprotein Oxidation and Its Pathobiological Significance. Journal of Biological Chemistry. 272(34), 20963-20966. http://doi.org/10.1074/jbc.272.34.20963.

Karas D, Ulrichova J, Valentova K. Gallovlation of polyphenols alters their biological activity. Food Chem Toxicol. 2017; 105:223-240. doi:https://doi.org/10.1016/j.fct.2017.04.021.

Fitzpatrick, D. F., Fleming, R. C., Bing, B., Maggi, D. A., & Malley, R. M. O. (2000). Isolation and Characterization of Endothelium-Dependent Vasorelaxating Compounds from Grape Seeds, 204, 6384-6390.

Byun, E., Ishikawa, T., Suyama, A., Kono, M., & Nakashima, S. (2012). Cardiovascular pharmacology A procyanidin trimer, C1, promotes NO production in rat aortic endothelial cells via both hyperpolarization and PI3K/Akt pathways. European Journal of Pharmacology, 692(1-3), 52-60. http://doi.org/10.1016/j.ejphar.2012.07.011.

Jang, H., Ridgeway, S. D., & Kim, J. (2013). Effects of the green tea polyphenol epigallocatechin-3-gallate on high-fat diet-induced insulin resistance and endothelial dysfunction, 1444-1451. http://doi.org/10.1152/ajpendo.00434.2013.

Ramirez-sanchez, I., Nogueira, L., Moreno, A., Taub, P., Perkins, G., Hogan, M. (2012). Stimulatory Effects of the Flavanol (−)-Epicatechin on Cardiac Angiogenesis: Additive Effects With Exercise, 60(5), 429-438.

Nogueira, L., Ramirez-sanchez, I., Perkins, G. A., Murphy, A., Taub, P. R., Ceballos, G. Malek, M. H. (2011). (−)-Epicatechin enhances fatigue resistance and oxidative capacity in mouse muscle, 18, 4615-4631. http://doi.org/10.1113/jphysiol.2011.209924.

Reiter C E (2010). Green tea polyphenol epigallocatechin gallate reduces endothelin-1 expression and secretion in vascular endothelial cells: roles for AMP-activated protein kinase, Akt, and FOXO1. https://www.ncbi.nlm.nih.gov/pubmed/19887561

Bahadi B. (2015). Gallic acid. A versatile antioxidant with promising therapeutic and industrial applications. http://pubs.rsc.org/en/content/articlelanding/2015/ra/c5ra01911g#!divAbstract Casas M, Buvinic S and Jaimovich E. ATP signaling in skeletal muscle: from fiber plasticity to regulation of metabolism. Exerc Sport Sci Rev 2014; 42, 110-116.

Osorio-Fuentealba C, Contreras-Ferrat A E, et al. Electrical stimuli release ATP to increase GLUT4 translocation and glucose uptake via PI3Kgamma-Akt-AS160 in skeletal muscle cells. Diabetes 2009; 62, 1519-1526.

Jorquera G, Altamirano F, et al. Cav1.1 controls frequency-dependent events regulating adult skeletal muscle plasticity. J Cell Sci 2013; 126, 1189-1198.

Jordan A N, Jurca R, et al. Effects of oral ATP supplementation on anaerobic power and muscular strength. Med Sci Sports Exerc 2004; 36, 983-990.

Wilson J M, Joy J M, et al. Effects of oral adenosine-5'-triphosphate supplementation on athletic performance, skeletal muscle hypertrophy and recovery in resistance-trained men. Nutr Metab (Lond) 2013; 10, 57.

Charest R., Blackmore P F, and Exton J H. Characterization of responses of isolated rat hepatocytes to ATP and ADP. J Biol Chem 1985; 260, 15789-15794.

Boynton A L, Cooney R V, et al. Extracellular ATP mobilizes intracellular Ca2+ in T51 B rat liver epithelial cells: a study involving single cell measurements. Exp Cell Res 1989; 181, 245-255.

Parker J C. Metabolism of external adenine nucleotides by human red blood cells. Am J Physiol 1970; 218, 1568-1574.

Schrader J, Berne R M and Rubio R. Uptake and metabolism of adenosine by human erythrocyte ghosts. Am J Physiol 1972; 223, 159-166.

Rathmacher J A, Fuller J C Jr., et al. Adenosine-5'-triphosphate (ATP) supplementation improves low peak muscle torque and torque fatigue during repeated high-intensity exercise sets. J Int Soc Sports Nutr 2012; 9, 48.

Agteresch H J, Dagnelie P C, et al. Adenosine triphosphate: established and potential clinical applications. Drugs 1999; 58, 211-232.

Khakh B S and North R A. P2X receptors as cell-surface ATP sensors in health and disease. Nature 2006; 442, 527-532.

Gomaa A A. Characteristics of analgesia induced by adenosine triphosphate. Pharmacol Toxicol 1987; 61, 199-202.

The advantages set forth above, and those made apparent from the foregoing description, are efficiently attained. While the disclosure is susceptible to various modifications and implementation in alternative forms, specific embodiments have been shown by way of non-limiting example in the drawings and have been described in detail herein. Since certain changes may be made in the above construction without departing from the scope of the instant application, it is intended that all matters contained in the foregoing description or shown in the accompanying drawings shall be interpreted as illustrative and not in a limiting sense.

The disclosure is not intended to be limited to the particular forms disclosed. Rather, the disclosure is to cover all modifications, equivalents, and alternatives falling within the scope of the disclosure as defined by the following appended claims and their legal equivalents.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

It is also to be understood that the following claims are intended to cover all of the generic and specific features of the invention herein described, and all statements of the scope of the invention that, as a matter of language, might be said to fall therebetween.

We claim:

1. A method of increasing blood flow in a subject, comprising:
    administering a composition to a subject, wherein the composition comprises:
    a therapeutically effective amount of an epigallocatechin gallate dimer and an epicatechin gallate dimer; and
    a pharmaceutically acceptable excipient or carrier.

2. The method of claim 1, wherein the therapeutically effective amount is equal to or greater than about 0.4 µM.

3. The method of claim 1, wherein a concentration of the therapeutically effective amount is about 5%-45% by weight.

4. The method of claim 1, wherein the method further comprises upregulating a canonical pathway in the subject selected from the group consisting of: Actin Cytoskeleton Signaling; Cluster of Differentiation 28 (CD28) Signaling in T Helper Cells; Chemokine Signaling; cAMP response element-binding (CREB) Signaling in Neurons; chemokine receptor type 4 (CXCR4) Signaling; Ephrin Receptor Signaling; extracellular signal regulated kinase/mitogen activated protein kinase (ERK/MAPK) Signaling; Fcγ Receptor-mediated Phagocytosis in Macrophages and Monocytes; N-formyl-Met-Leu-Phe (fMLP) Signaling in Neutrophils; Gonadotropin-releasing hormone (GNRH) Signaling; Glycoprotein VI (GP6) Signaling Pathway; Gα12/13 Signaling; Gaq Signaling; Gas Signaling; IL-6 Signaling; IL-8 Signaling; Insulin Receptor Signaling; Integrin Signaling; Melatonin Signaling; Nitric Oxide Signaling in the Cardiovascular System; Noradrenaline and Adrenaline Degradation; Nuclear factor erythroid 2 (NRF2)-mediated Oxidative Stress Response; Oncostatin M Signaling; Oxidative Phosphorylation; P2Y Purigenic Receptor Signaling Pathway; p70S6K Signaling; p21 activated protein kinases (PAK) Signaling; Phospholipase C Signaling; Phosphoinositide-3-Kinases (PI3K) Signaling in B Lymphocytes; PI3K/protein kinase B (AKT) Signaling; Production of Nitric Oxide and Reactive Oxygen Species in Macrophages; Protein Kinase A Signaling; Rac Signaling; Receptor activator of nuclear factor κ B (RANK) Signaling in Osteoclasts; Regulation of Actin-based Motility by Rho; RhoA Signaling; Signaling by Rho Family guanosine triphosphate (GTP)ases; Synaptic Long Term Potentiation; Telomerase Signaling; and α-Adrenergic Signaling.

5. The method of claim 4, wherein administration to the subject causes an increase in intracellular nitric oxide production.

6. The method of claim 4, wherein administration to the subject causes an increase in endothelium NO synthase (eNOS).

7. The method of claim 4, wherein administration to the subject causes an increase in inducible NO synthase (iNOS).

8. The method of claim 4, wherein administration to the subject causes increased skeletal muscle pump, increased blood oxygenation, lower blood pressure, increased cognizance, dose-specific increase in nitric oxide production, dose-specific increase in vasodilation, reduced fat, increased muscle stamina, increased blood flow to muscles, increased blood flow to brain, decreased exercise/workout recovery time, increased exercise efficiency, increased alertness, pre-performance/workout treatment for stimulation of workout vigor (mental and physical) and enhanced performance, post-performance/workout supplement for muscle recovery, male/female virility enhancement, increased metabolic rate, increased workout volume, reduced feeling of effort during exercise, increased motivation to exercise, as drug or supplement delivery mechanism, as a nutrient delivery mechanism, oxygenated blood delivery, as a prevention and/or treatment of endothelial dysfunction, reduced stress and anxiety, as a sleep aid, reduced hangover after alcohol consumption, increased energy, enhanced heart health, enhanced respiratory efficiency, increased angiogenesis, as treatment for wound closure, enhanced food and beverage flavoring, improved skin and hair/coat in non-humans, improved skin and hair in humans, and enhanced matrix metalloproteinases proliferation.

9. The method of claim 1, wherein the composition is an energy drink.

10. The method of claim 1, wherein the composition further comprises Catechin Dimer Gallate, Catechin Trimer, Catechin Tetramer, catechin dimer digallate, and Catechin Dimer.

11. The method of claim 1, wherein the epigallocatechin gallate dimer is a first epigallocatechin gallate dimer and the composition further comprises a second epigallocatechin gallate dimer.

12. The method of claim 1, wherein the composition is prepared by a process comprising the steps of:
  extracting the polyphenols, catechins, epicatechins, and galloylated epicatechins from a raw material using hot water at a temperature of about 80° C. to about 85° C. to provide an unrefined material;
  passing the unrefined material through a mesh filter to provide a filtered material;
  absorbing the filtered material with a macro-porous absorption resin;
  eluting impurities from the filtered material absorbed to the resin using pure water;
  eluting the material from the resin in ethanol and collecting an ethanol eluent fraction therefrom;
  concentrating the ethanol eluent fraction and recovering a solvent using a vacuum system to provide a resulting material;
  pasteurizing, sterilizing, and cooling the resulting material;
  spray drying the material into a powder; and
  sifting and v-blending the powder.

13. The method of claim 12, wherein the raw material is green tea leaves.

14. The method of claim 1, wherein the composition is prepared by a process comprising the steps of:
  initially extracting polyphenols, catechins, epicatechins, and galloylated epicatechins from a sample using ethyl acetate;
  further extracting the polyphenols, catechins, epicatechins, and galloylated epicatechins from the sample using water to provide a resulting material;
  eluting the resulting material using resin and diluting the material with ethanol;
  filtering the material using activated carbon;
  concentrating the material;
  spray drying the material into a powder; and
  v-blending, sieving, and de-ironing the powder.

15. The method of claim 14, wherein the raw material is green tea leaves.

* * * * *

UNITED STATES PATENT AND TRADEMARK OFFICE
CERTIFICATE OF CORRECTION

PATENT NO. : 11,766,422 B2
APPLICATION NO. : 16/980519
DATED : September 26, 2023
INVENTOR(S) : Michael Louis Sperduti et al.

It is certified that error appears in the above-identified patent and that said Letters Patent is hereby corrected as shown below:

In the Claims

Column 67:
Line 1, "claim 4" should read --claim 1--;
Line 4, "claim 4" should read --claim 1--;
Line 7, "claim 4" should read --claim 1--;
Line 9, "claim 4" should read --claim 1--.

Signed and Sealed this
Sixteenth Day of April, 2024

Katherine Kelly Vidal
*Director of the United States Patent and Trademark Office*